United States Patent
Jimenez et al.

(10) Patent No.: US 10,028,741 B2
(45) Date of Patent: Jul. 24, 2018

(54) SYSTEMS AND METHODS FOR PERCUTANEOUS ACCESS, STABILIZATION AND CLOSURE OF ORGANS

(71) Applicant: Apica Cardiovascular Limited, Galway (IE)

(72) Inventors: Jorge Hernan Jimenez, Atlanta, GA (US); Dustin Seth West, Calhoun, GA (US); Brendan Cunniffe, Galway (IE); Thomas Feeney, Galway (IE); James L. Greene, Galway (IE); Robin Stephens, Sussex (GB)

(73) Assignee: Apica Cardiovascular Limited, Galway (IE)

( * ) Notice: Subject to any disclaimer, the term of this patent is extended or adjusted under 35 U.S.C. 154(b) by 285 days.

(21) Appl. No.: 14/808,037

(22) Filed: Jul. 24, 2015

(65) Prior Publication Data
US 2015/0342602 A1    Dec. 3, 2015

Related U.S. Application Data

(63) Continuation of application No. PCT/US2014/013195, filed on Jan. 27, 2014.
(Continued)

(51) Int. Cl.
*A61B 17/08* (2006.01)
*A61B 17/064* (2006.01)
(Continued)

(52) U.S. Cl.
CPC ...... *A61B 17/0644* (2013.01); *A61B 17/0057* (2013.01); *A61B 17/0401* (2013.01);
(Continued)

(58) Field of Classification Search
CPC ............... A61M 39/06; A61B 17/0644; A61B 17/0057; A61B 17/3421; A61B 17/0401; A61B 17/0643
See application file for complete search history.

(56) References Cited

U.S. PATENT DOCUMENTS 3,512,519 A    5/1970  Hall
3,540,451 A    11/1970  Zeman
(Continued)

FOREIGN PATENT DOCUMENTS

CA    2526920    2/2009
CN    1842354    10/2006
(Continued)

OTHER PUBLICATIONS

PCT International Search Report for PCT Application No. PCT/US2014/013195 dated May 1, 2014 (5 pages).
(Continued)

*Primary Examiner* — Richard Louis
(74) *Attorney, Agent, or Firm* — Eversheds Sutherland (US) LLP

(57) ABSTRACT

Systems and methods for accessing, stabilizing and sealing a device attached to a tissue surface comprising a tissue attaching device having an outer base ring defining an opening therethrough and a distally projecting tissue attachment element. The systems variously utilize annular sealing flanges distally attached to the outer base ring outside or inside the tissue attachment element to create a fluid tight seal. The systems variously utilize coils with regions of differing pitch to create sealing tissue pressure. Methods for installing an apical attaching device with a transapical port into a patient, comprising assessing the patient's viability for installation of the apical attaching device by determining an Index of Tissue Elasticity (ITE).

18 Claims, 50 Drawing Sheets

Related U.S. Application Data

(60) Provisional application No. 61/756,885, filed on Jan. 25, 2013, provisional application No. 61/777,796, filed on Mar. 12, 2013, provisional application No. 61/819,237, filed on May 3, 2013, provisional application No. 61/835,712, filed on Jun. 17, 2013.

(51) Int. Cl.
  *A61B 17/00* (2006.01)
  *A61M 39/06* (2006.01)
  *A61B 17/04* (2006.01)
  *A61B 17/34* (2006.01)
  *A61B 17/30* (2006.01)
  *A61B 90/00* (2016.01)

(52) U.S. Cl.
  CPC ...... *A61B 17/0643* (2013.01); *A61B 17/3421* (2013.01); *A61M 39/06* (2013.01); *A61B 2017/00247* (2013.01); *A61B 2017/00252* (2013.01); *A61B 2017/00305* (2013.01); *A61B 2017/00318* (2013.01); *A61B 2017/00336* (2013.01); *A61B 2017/00349* (2013.01); *A61B 2017/00575* (2013.01); *A61B 2017/00588* (2013.01); *A61B 2017/00615* (2013.01); *A61B 2017/00623* (2013.01); *A61B 2017/00703* (2013.01); *A61B 2017/00867* (2013.01); *A61B 2017/00902* (2013.01); *A61B 2017/0406* (2013.01); *A61B 2017/0464* (2013.01); *A61B 2017/0498* (2013.01); *A61B 2017/0649* (2013.01); *A61B 2017/306* (2013.01); *A61B 2017/3419* (2013.01); *A61B 2017/3425* (2013.01); *A61B 2017/3466* (2013.01); *A61B 2017/3488* (2013.01); *A61B 2090/0801* (2016.02)

(56) References Cited

U.S. PATENT DOCUMENTS

| | | |
|---|---|---|
| 3,856,021 A | 12/1974 | McIntosh |
| 4,204,541 A | 5/1980 | Kapitanov |
| 4,366,819 A | 1/1983 | Kaster |
| 4,769,031 A | 9/1988 | McGough et al. |
| 4,904,264 A | 2/1990 | Scheunemann |
| 4,955,856 A | 9/1990 | Phillips |
| 5,098,369 A | 3/1992 | Heilman et al. |
| 5,129,913 A | 7/1992 | Ruppert |
| 5,139,517 A | 8/1992 | Corral |
| 5,158,563 A | 10/1992 | Cosman |
| 5,222,980 A | 6/1993 | Gealow |
| 5,256,160 A | 10/1993 | Clement |
| 5,291,179 A | 3/1994 | Ooe et al. |
| 5,387,193 A | 2/1995 | Miracki |
| 5,447,533 A | 9/1995 | Vachon et al. |
| 5,456,714 A | 10/1995 | Owen |
| 5,562,729 A | 10/1996 | Purdy et al. |
| 5,577,993 A | 11/1996 | Zhu et al. |
| 5,582,616 A | 12/1996 | Bolduc et al. |
| 5,695,504 A | 12/1997 | Gifford et al. |
| 5,728,116 A | 3/1998 | Rosenman |
| 5,738,680 A * | 4/1998 | Mueller ............... A61B 18/24 606/15 |
| 5,755,697 A | 5/1998 | Jones et al. |
| 5,782,844 A | 7/1998 | Yoon et al. |
| 5,797,933 A | 8/1998 | Snow et al. |
| 5,810,836 A | 9/1998 | Hussein et al. |
| 5,810,851 A | 9/1998 | Yoon |
| 5,814,005 A | 9/1998 | Barra et al. |
| 5,824,070 A | 10/1998 | Jarvik |
| 5,824,071 A | 10/1998 | Nelson et al. |
| 5,827,316 A | 10/1998 | Young et al. |
| 5,833,698 A | 11/1998 | Hinchliffe et al. |
| 5,843,088 A | 12/1998 | Barra et al. |
| 5,865,791 A | 2/1999 | Whyane et al. |
| 5,893,369 A | 4/1999 | LeMole |
| 5,910,153 A | 6/1999 | Mayenberger |
| 5,924,424 A | 7/1999 | Stevens et al. |
| 5,944,730 A | 8/1999 | Nobles et al. |
| 5,976,174 A | 11/1999 | Ruiz |
| 5,984,956 A | 11/1999 | Tweden et al. |
| 5,989,278 A | 11/1999 | Mueller |
| 6,001,056 A | 12/1999 | Jassawalla et al. |
| 6,007,576 A | 12/1999 | McClellan |
| 6,022,324 A | 2/2000 | Skinner |
| 6,022,367 A | 2/2000 | Sherts |
| 6,024,755 A | 2/2000 | Addis |
| 6,039,748 A | 3/2000 | Savage et al. |
| 6,066,085 A | 5/2000 | Heilman et al. |
| 6,079,414 A | 6/2000 | Roth |
| 6,080,173 A | 6/2000 | Williamson, IV et al. |
| 6,080,176 A | 6/2000 | Young |
| 6,113,611 A | 9/2000 | Allen et al. |
| 6,146,325 A | 11/2000 | Lewis et al. |
| 6,241,743 B1 | 6/2001 | Levin et al. |
| 6,254,564 B1 | 7/2001 | Wilk et al. |
| 6,267,732 B1 | 7/2001 | Heneveld et al. |
| 6,273,862 B1 | 8/2001 | Privitera et al. |
| 6,290,639 B1 | 9/2001 | Mussivand et al. |
| 6,290,728 B1 | 9/2001 | Phelps et al. |
| 6,346,071 B1 | 2/2002 | Mussivand |
| 6,390,976 B1 | 5/2002 | Spence et al. |
| 6,401,720 B1 | 6/2002 | Stevens et al. |
| 6,409,739 B1 | 6/2002 | Nobles et al. |
| 6,443,957 B1 | 9/2002 | Addis |
| 6,458,140 B2 | 10/2002 | Akin et al. |
| 6,506,197 B1 | 1/2003 | Rollero et al. |
| 6,537,300 B2 | 3/2003 | Girton |
| 6,551,319 B2 | 4/2003 | Lieberman |
| 6,551,322 B1 | 4/2003 | Lieberman |
| 6,551,332 B1 | 4/2003 | Nguyen et al. |
| 6,589,277 B1 | 7/2003 | Fabiani et al. |
| 6,607,541 B1 | 8/2003 | Gardiner et al. |
| 6,638,237 B1 | 10/2003 | Guiles et al. |
| 6,651,670 B2 | 11/2003 | Rapacki et al. |
| 6,663,633 B1 | 12/2003 | Pierson, III |
| 6,669,708 B1 | 12/2003 | Nissenbaum et al. |
| 6,673,043 B1 | 1/2004 | Landesberg |
| 6,676,678 B2 | 1/2004 | Gifford, III et al. |
| 6,689,147 B1 | 2/2004 | Koster, Jr. |
| 6,695,859 B1 | 2/2004 | Golden et al. |
| 6,699,256 B1 | 3/2004 | Logan et al. |
| 6,705,988 B2 | 3/2004 | Spence et al. |
| 6,726,648 B2 | 4/2004 | Kaplon et al. |
| 6,732,501 B2 | 5/2004 | Yu et al. |
| 6,740,101 B2 | 5/2004 | Houser et al. |
| 6,776,787 B2 | 8/2004 | Phung et al. |
| 6,802,806 B2 | 10/2004 | McCarthy et al. |
| 6,808,498 B2 | 10/2004 | Laroya et al. |
| 6,824,071 B1 | 11/2004 | McMichael |
| 6,827,683 B2 | 12/2004 | Otawara |
| 6,863,677 B2 | 3/2005 | Breznock |
| 6,869,437 B1 | 3/2005 | Hausen et al. |
| 6,942,672 B2 | 9/2005 | Heilman et al. |
| 6,978,176 B2 | 12/2005 | Lattouf |
| 6,984,241 B2 | 1/2006 | Lubbers et al. |
| 6,994,666 B2 | 2/2006 | Shannon et al. |
| 7,018,384 B2 | 3/2006 | Skakoon |
| 7,033,372 B1 | 4/2006 | Cahalan |
| 7,048,681 B2 | 5/2006 | Tsubouchi et al. |
| 7,056,286 B2 | 6/2006 | Ravenscroft et al. |
| 7,077,801 B2 | 7/2006 | Haverich |
| 7,083,631 B2 | 8/2006 | Houser et al. |
| 7,163,525 B2 | 1/2007 | Franer |
| 7,182,771 B1 | 2/2007 | Houser et al. |
| 7,214,234 B2 | 5/2007 | Rapacki et al. |
| 7,232,421 B1 | 6/2007 | Gambale et al. |
| 7,258,694 B1 | 8/2007 | Choi et al. |
| 7,309,343 B2 | 12/2007 | Vargas et al. |
| 7,331,956 B2 | 2/2008 | Hovda et al. |
| 7,404,792 B2 | 7/2008 | Spence et al. |
| 7,510,561 B2 | 3/2009 | Beane et al. |

(56) References Cited

U.S. PATENT DOCUMENTS

| | | |
|---|---|---|
| 7,637,919 B2 | 12/2009 | Ishikawa et al. |
| 7,717,844 B2 | 5/2010 | Cohn |
| 7,744,527 B2 | 6/2010 | Cohn |
| 7,766,811 B2 | 8/2010 | Haverich |
| 7,799,041 B2 | 9/2010 | Beane et al. |
| 7,842,068 B2 | 11/2010 | Ginn |
| 7,846,123 B2 | 12/2010 | Vassiliades et al. |
| 7,846,179 B2 | 12/2010 | Belef et al. |
| 7,931,581 B2 | 4/2011 | Cohn |
| 7,942,805 B2 | 5/2011 | Shambaugh, Jr. |
| 7,993,392 B2 | 8/2011 | Righini et al. |
| 8,226,670 B2 | 7/2012 | Beane et al. |
| 8,430,836 B2 | 4/2013 | Vassiliades et al. |
| 8,556,930 B2 | 10/2013 | Ellingwood |
| 8,579,790 B2 | 11/2013 | Jeffery et al. |
| 8,764,795 B2 | 7/2014 | Whitman et al. |
| 8,840,538 B2 | 9/2014 | Jeffery et al. |
| 8,858,489 B2 | 10/2014 | Vassiliades et al. |
| 2001/0051809 A1 | 12/2001 | Houser et al. |
| 2002/0019623 A1 | 2/2002 | Altman et al. |
| 2002/0019643 A1 | 2/2002 | Gifford et al. |
| 2002/0032462 A1 | 3/2002 | Houser et al. |
| 2002/0038127 A1 | 3/2002 | Blatter et al. |
| 2002/0045846 A1 | 4/2002 | Kaplon et al. |
| 2002/0055737 A1 | 5/2002 | Lieberman |
| 2002/0055738 A1 | 5/2002 | Lieberman |
| 2002/0055739 A1 | 5/2002 | Lieberman |
| 2002/0055740 A1 | 5/2002 | Lieberman |
| 2002/0055742 A1 | 5/2002 | Lieberman |
| 2002/0058958 A1 | 5/2002 | Walen |
| 2002/0095210 A1 | 7/2002 | Finnegan et al. |
| 2002/0099394 A1 | 7/2002 | Houser et al. |
| 2002/0116018 A1 | 8/2002 | Stevens et al. |
| 2002/0177865 A1 | 11/2002 | McIntosh |
| 2002/0183786 A1 | 12/2002 | Girton |
| 2002/0193806 A1 | 12/2002 | Moenning et al. |
| 2003/0014064 A1 | 1/2003 | Blatter |
| 2003/0023255 A1 | 1/2003 | Miles et al. |
| 2003/0032979 A1 | 2/2003 | Mortier et al. |
| 2003/0040765 A1 | 2/2003 | Breznock |
| 2003/0045834 A1 | 3/2003 | Wing et al. |
| 2003/0078592 A1 | 4/2003 | Heilman et al. |
| 2003/0130668 A1 | 7/2003 | Nieman |
| 2003/0181843 A1 | 9/2003 | Bibber et al. |
| 2003/0181913 A1 | 9/2003 | Lieberman |
| 2004/0002624 A1 | 1/2004 | Yu et al. |
| 2004/0050393 A1 | 3/2004 | Golden et al. |
| 2004/0068299 A1 | 4/2004 | Laske et al. |
| 2004/0073216 A1 | 4/2004 | Lieberman |
| 2004/0077989 A1 | 4/2004 | Goode et al. |
| 2004/0092858 A1 | 5/2004 | Wilson et al. |
| 2004/0097973 A1 | 5/2004 | Loshakove et al. |
| 2004/0097993 A1 | 5/2004 | Whayne |
| 2004/0098011 A1 | 5/2004 | Vargas et al. |
| 2004/0133155 A1 | 7/2004 | Varner et al. |
| 2004/0138702 A1* | 7/2004 | Peartree ............. A61B 17/3421 606/213 |
| 2004/0153112 A1 | 8/2004 | Nissenbaum et al. |
| 2004/0158308 A1* | 8/2004 | Hogendijk ................ A61F 2/88 623/1.11 |
| 2004/0162608 A1 | 8/2004 | Haverich |
| 2004/0167547 A1 | 8/2004 | Beane et al. |
| 2004/0167551 A1 | 8/2004 | Gifford, III et al. |
| 2004/0171905 A1 | 9/2004 | Yu et al. |
| 2004/0186490 A1 | 9/2004 | Houser et al. |
| 2004/0225306 A1 | 11/2004 | Blatter et al. |
| 2004/0236170 A1 | 11/2004 | Kim |
| 2005/0033107 A1 | 2/2005 | Tsubouchi |
| 2005/0043781 A1 | 2/2005 | Foley |
| 2005/0075656 A1 | 4/2005 | Beaupre |
| 2005/0101982 A1 | 5/2005 | Ravenscroft et al. |
| 2005/0101983 A1 | 5/2005 | Loshakove et al. |
| 2005/0131451 A1 | 6/2005 | Kleshinski et al. |
| 2005/0137609 A1 | 6/2005 | Guiraudon |
| 2005/0149093 A1 | 7/2005 | Pokorney |
| 2005/0154411 A1 | 7/2005 | Breznock et al. |
| 2005/0171479 A1 | 8/2005 | Hruska et al. |
| 2005/0187568 A1 | 8/2005 | Klenk et al. |
| 2005/0192604 A1 | 9/2005 | Carson et al. |
| 2005/0209502 A1 | 9/2005 | Schmid et al. |
| 2005/0222582 A1 | 10/2005 | Wenchell |
| 2005/0251162 A1* | 11/2005 | Rothe .................. A61B 1/0014 606/153 |
| 2005/0251187 A1 | 11/2005 | Beane et al. |
| 2005/0256368 A1 | 11/2005 | Klenk et al. |
| 2005/0267495 A1 | 12/2005 | Ginn et al. |
| 2006/0020326 A9 | 1/2006 | Bolduc et al. |
| 2006/0036313 A1 | 2/2006 | Vassiliades et al. |
| 2006/0074484 A1 | 4/2006 | Huber |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2006/0167333 A1 | 7/2006 | Moore et al. |
| 2006/0178675 A1 | 8/2006 | Hamman |
| 2006/0241659 A1 | 10/2006 | Tulleken et al. |
| 2006/0259050 A1 | 11/2006 | DeWinter |
| 2007/0055357 A1 | 3/2007 | Pokorney et al. |
| 2007/0060952 A1 | 3/2007 | Roby et al. |
| 2007/0066943 A1 | 3/2007 | Prasad et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0106328 A1 | 5/2007 | Wardle et al. |
| 2007/0112361 A1 | 5/2007 | Schonholz et al. |
| 2007/0167968 A1 | 7/2007 | Pandey |
| 2007/0167969 A1 | 7/2007 | Pandey |
| 2007/0173879 A1 | 7/2007 | Pandey |
| 2007/0197856 A1 | 8/2007 | Gellman et al. |
| 2007/0208214 A1 | 9/2007 | Hjelle et al. |
| 2007/0265643 A1 | 11/2007 | Beane et al. |
| 2008/0004640 A1* | 1/2008 | Ellingwood ....... A61B 17/0057 606/151 |
| 2008/0009668 A1 | 1/2008 | Cohn |
| 2008/0009887 A1 | 1/2008 | Cohn |
| 2008/0009891 A1 | 1/2008 | Cohn |
| 2008/0039883 A1 | 2/2008 | Nohilly |
| 2008/0058846 A1 | 3/2008 | Vosough |
| 2008/0076959 A1 | 3/2008 | Farnan et al. |
| 2008/0161826 A1 | 7/2008 | Guiraudon |
| 2008/0177301 A1 | 7/2008 | Svensson |
| 2008/0255597 A1 | 10/2008 | Pravong et al. |
| 2009/0012552 A1 | 1/2009 | Pandey et al. |
| 2009/0082778 A1 | 3/2009 | Beane et al. |
| 2009/0112062 A1 | 4/2009 | Bakos |
| 2009/0203957 A1 | 8/2009 | LaRose et al. |
| 2009/0204206 A1 | 8/2009 | Parquet et al. |
| 2009/0240264 A1* | 9/2009 | Tuval ................ A61B 17/0469 606/148 |
| 2010/0004739 A1 | 1/2010 | Vesely |
| 2010/0010500 A1 | 1/2010 | Beane et al. |
| 2010/0010616 A1 | 1/2010 | Drews et al. |
| 2010/0049225 A1 | 2/2010 | To et al. |
| 2010/0087907 A1 | 4/2010 | Lattouf |
| 2010/0160847 A1 | 6/2010 | Braido et al. |
| 2010/0161040 A1 | 6/2010 | Braido et al. |
| 2010/0168778 A1 | 7/2010 | Braido |
| 2011/0092761 A1 | 4/2011 | Almog et al. |
| 2011/0106116 A1 | 5/2011 | Ducharme et al. |
| 2011/0118766 A1 | 5/2011 | Reichenbach et al. |
| 2011/0118770 A1 | 5/2011 | Pokorney et al. |
| 2011/0118833 A1 | 5/2011 | Reichenbach et al. |
| 2011/0144680 A1 | 6/2011 | Nguyen et al. |
| 2011/0160850 A1 | 6/2011 | Bourque |
| 2011/0190811 A1 | 8/2011 | Shanley |
| 2011/0196190 A1 | 8/2011 | Farnan et al. |
| 2011/0224785 A1 | 9/2011 | Hacohen |
| 2011/0251450 A1 | 10/2011 | Pagani et al. |
| 2012/0059212 A1 | 3/2012 | LaRose et al. |
| 2012/0059457 A1 | 3/2012 | Leinsing et al. |
| 2012/0089181 A1 | 4/2012 | Shanley et al. |
| 2012/0123452 A1 | 5/2012 | Asfora et al. |
| 2012/0123461 A1 | 5/2012 | Gillies et al. |
| 2012/0226096 A1 | 9/2012 | Callaway et al. |

(56) References Cited

U.S. PATENT DOCUMENTS

| | | |
|---|---|---|
| 2012/0253386 A1 | 10/2012 | Rowe et al. |
| 2012/0296151 A1 | 11/2012 | Curtis et al. |
| 2012/0296358 A1 | 11/2012 | Nguyen et al. |
| 2013/0012761 A1 | 1/2013 | Gregorio et al. |
| 2013/0110228 A1 | 5/2013 | Braido |
| 2013/0116728 A1 | 5/2013 | Litvack et al. |
| 2013/0150654 A1 | 6/2013 | Stanfield et al. |
| 2013/0218169 A1 | 8/2013 | Vassiliades et al. |
| 2013/0253641 A1 | 9/2013 | Lattouf |
| 2014/0039375 A1 | 2/2014 | Jimenez et al. |
| 2014/0067057 A1 | 3/2014 | Callaway et al. |
| 2014/0100430 A1 | 4/2014 | Beane et al. |
| 2014/0148786 A1 | 5/2014 | Milo |
| 2014/0194833 A1 | 7/2014 | Andrus |
| 2014/0214159 A1 | 7/2014 | Vidlund et al. |
| 2014/0378772 A1 | 12/2014 | Sundt, III et al. |
| 2014/0379074 A1 | 12/2014 | Spence et al. |
| 2015/0032153 A1 | 1/2015 | Quadri et al. |
| 2015/0038770 A1 | 2/2015 | Colella |
| 2015/0112120 A1 | 4/2015 | Andrus |
| 2015/0196321 A1 | 7/2015 | Gregory et al. |
| 2016/0095705 A1 | 4/2016 | Keranen et al. |

FOREIGN PATENT DOCUMENTS

| | | |
|---|---|---|
| EP | 1 669 042 | 6/2006 |
| EP | 1 706 168 | 10/2006 |
| EP | 1 691 884 | 3/2011 |
| EP | 1 628 702 | 5/2013 |
| JP | 09-47457 | 2/1997 |
| JP | 11-500642 | 1/1999 |
| JP | 2002-518082 | 6/2002 |
| JP | 2006-518624 | 8/2006 |
| JP | 2007-510522 | 4/2007 |
| WO | 93/25148 | 12/1993 |
| WO | 96/25886 | 8/1996 |
| WO | 97/13463 | 4/1997 |
| WO | 99/65409 | 12/1999 |
| WO | 00/00193 | 1/2000 |
| WO | 00/15147 | 3/2000 |
| WO | 00/15149 | 3/2000 |
| WO | 00/41759 | 7/2000 |
| WO | 2000/074747 | 12/2000 |
| WO | 2003/001980 | 1/2003 |
| WO | 2004/026147 | 4/2004 |
| WO | 2004/096059 | 11/2004 |
| WO | 2005/046783 | 5/2005 |
| WO | 2006/019755 | 2/2006 |
| WO | 2006/020651 | 2/2006 |
| WO | 2006/093970 | 9/2006 |
| WO | 2007/038109 | 4/2007 |
| WO | 2007/047212 | 4/2007 |
| WO | 2007/047933 A2 | 4/2007 |
| WO | 2007/117612 | 10/2007 |
| WO | 2008/131453 | 10/2008 |
| WO | 2008/153872 | 12/2008 |
| WO | 2009/100198 | 8/2009 |
| WO | 2009/117435 | 9/2009 |
| WO | 2012/025927 A2 | 3/2012 |
| WO | 2012/040233 | 3/2012 |
| WO | 2012/103546 | 8/2012 |
| WO | 2012/103546 A2 | 8/2012 |
| WO | 2012/106422 | 8/2012 |
| WO | 2012/106422 A2 | 8/2012 |
| WO | 2013/064529 | 5/2013 |
| WO | 2013/189620 | 12/2013 |
| WO | 2015/109328 | 7/2015 |

OTHER PUBLICATIONS

Partial EP Search Report for EP Application No. EP 14743520.0 dated Nov. 14, 2016 (7 pages).

* cited by examiner

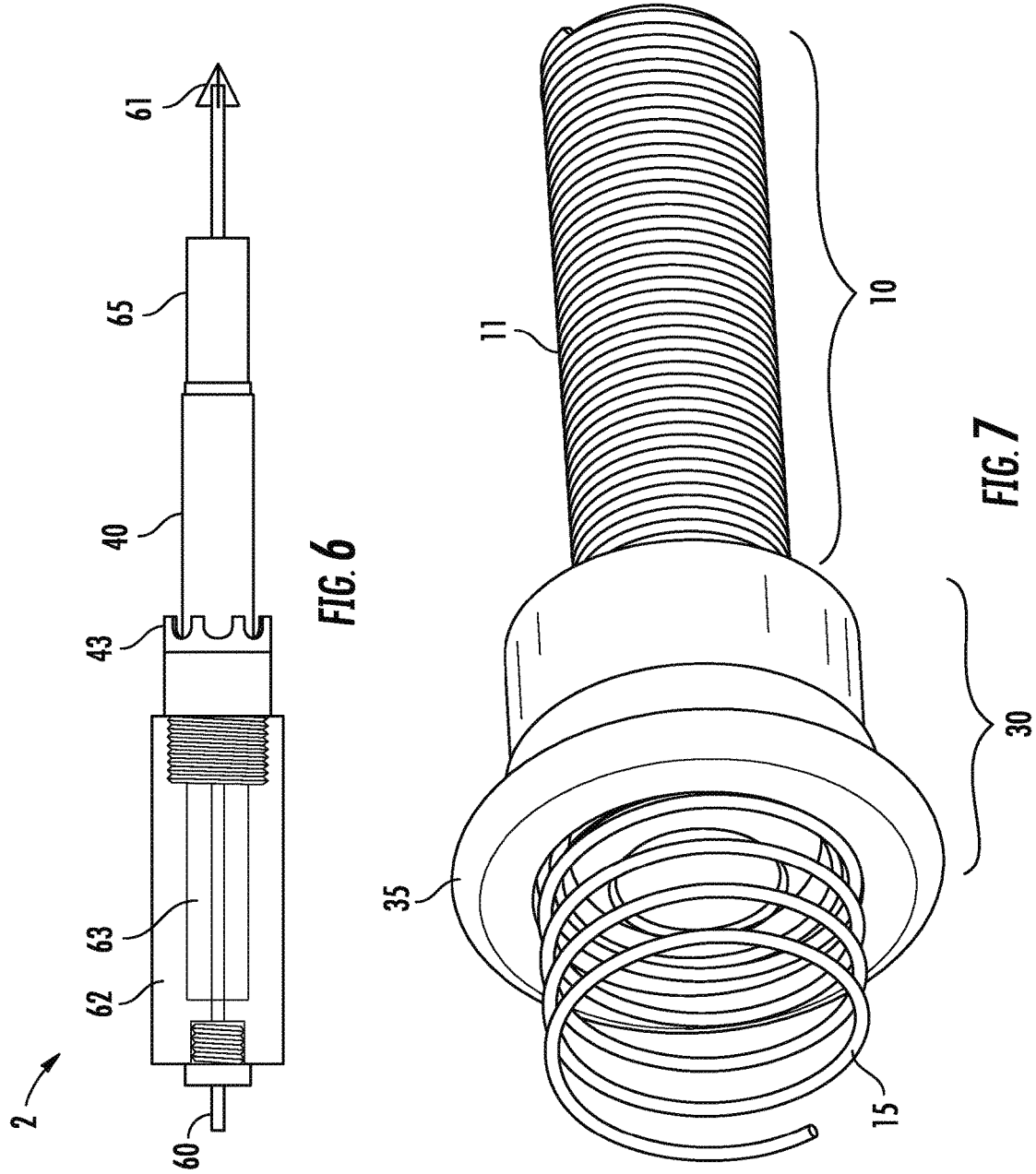

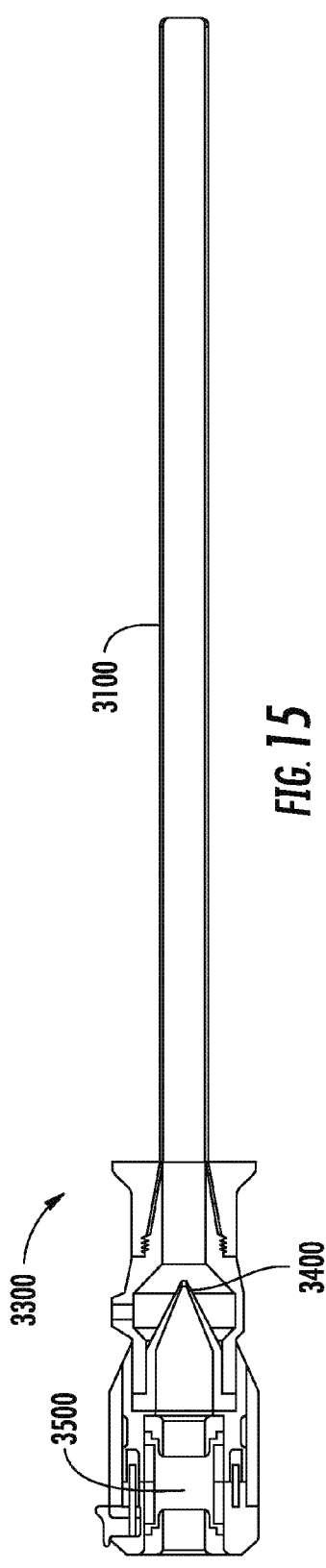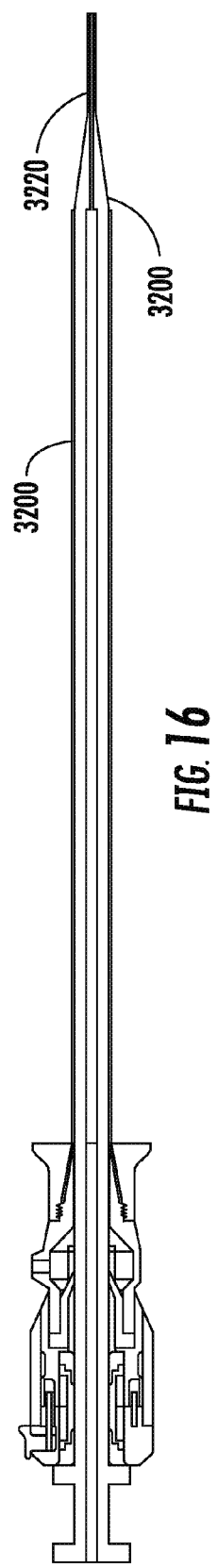

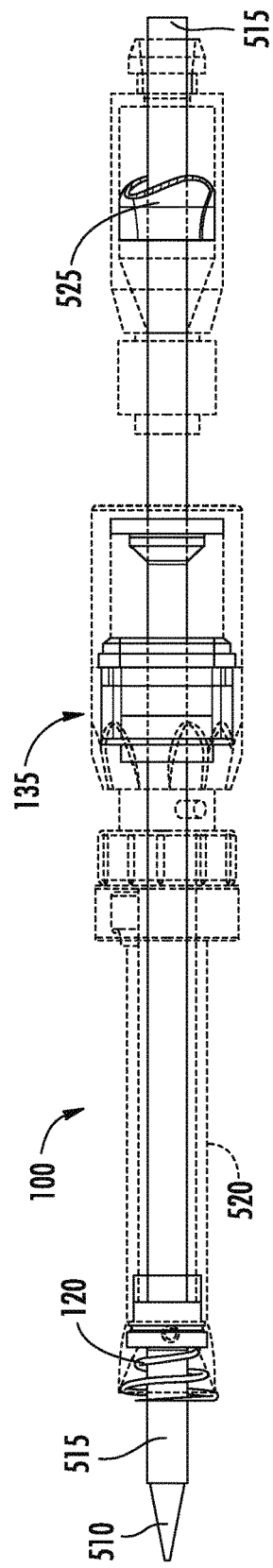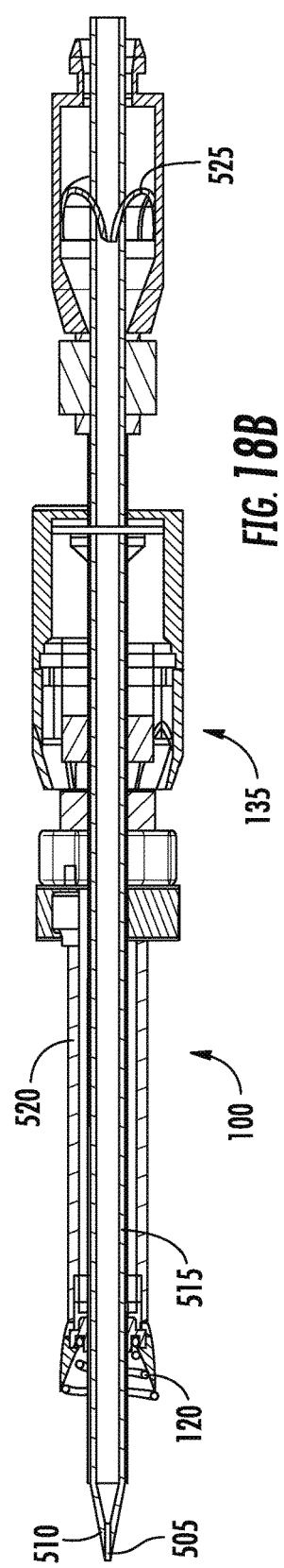

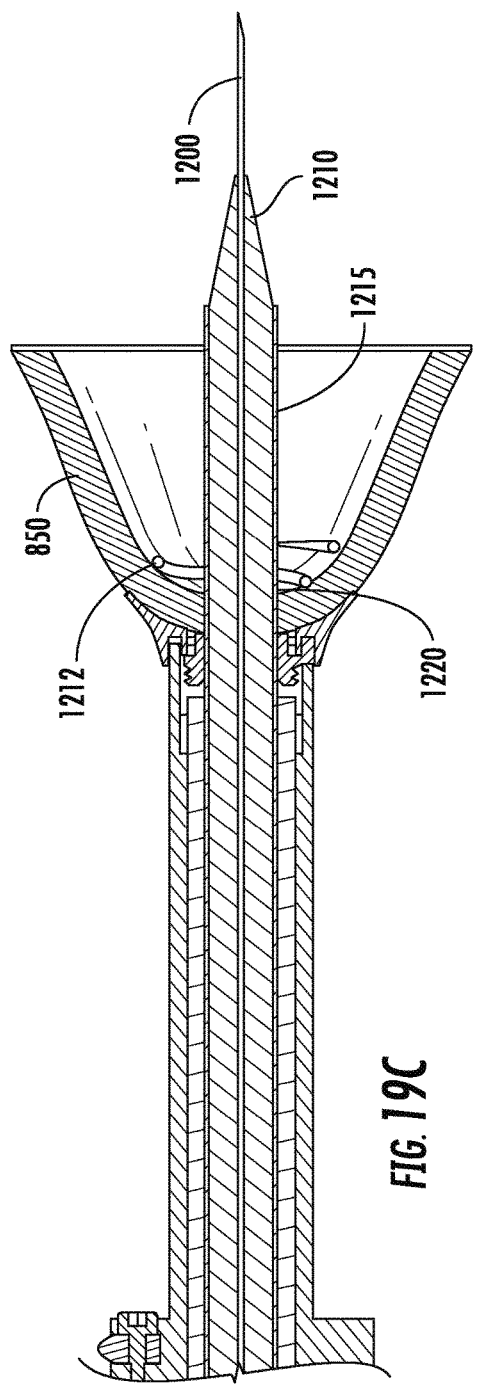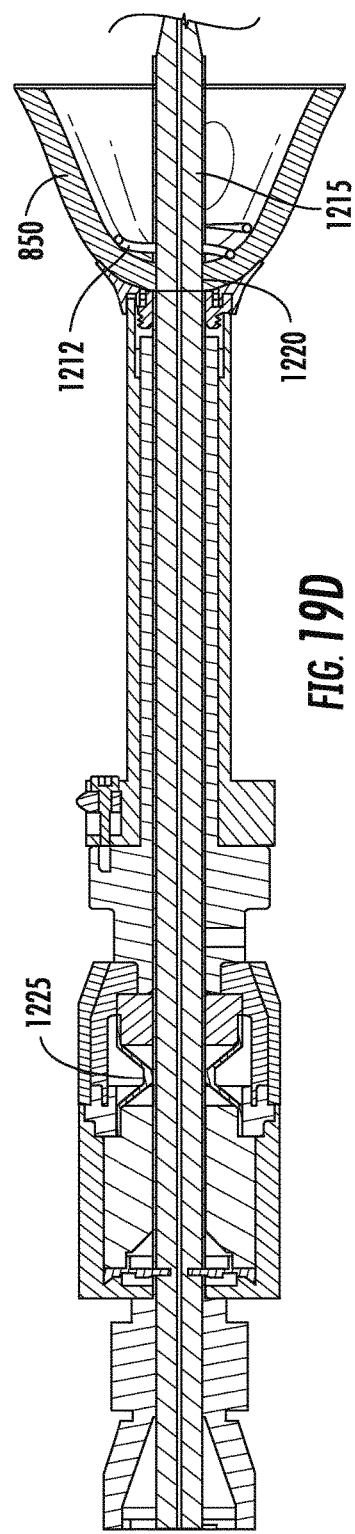

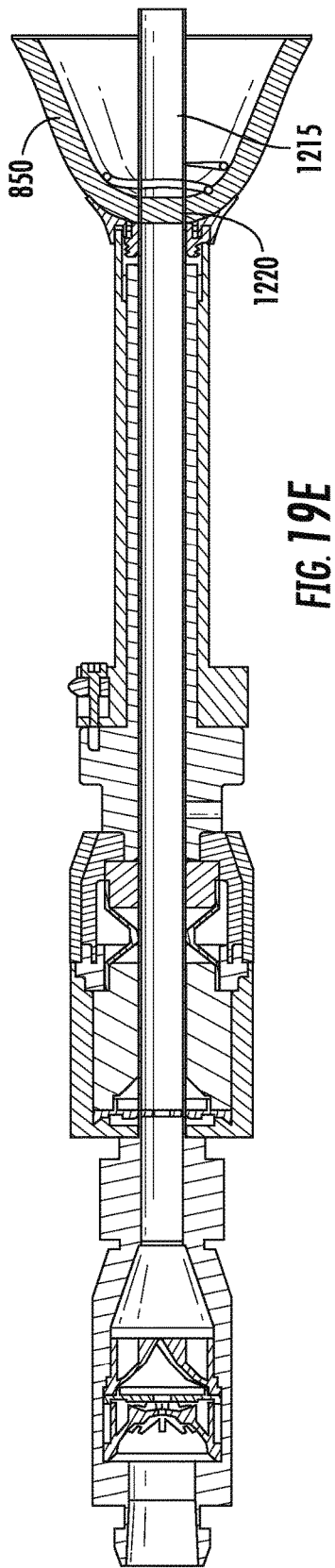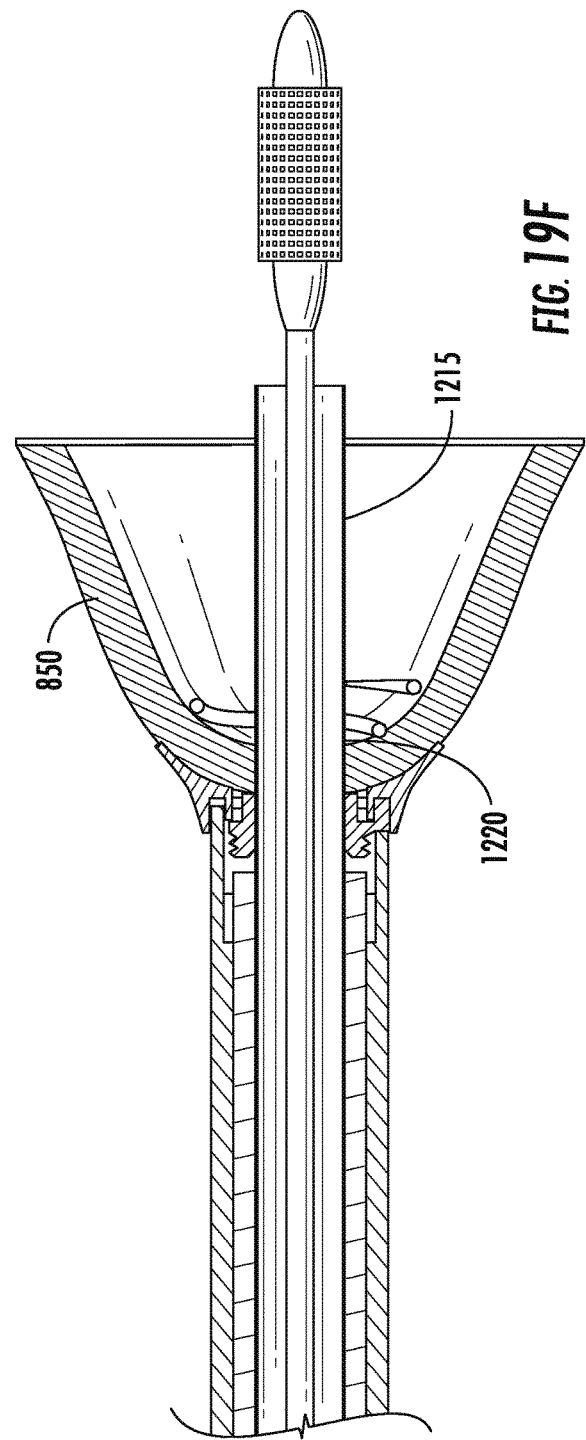

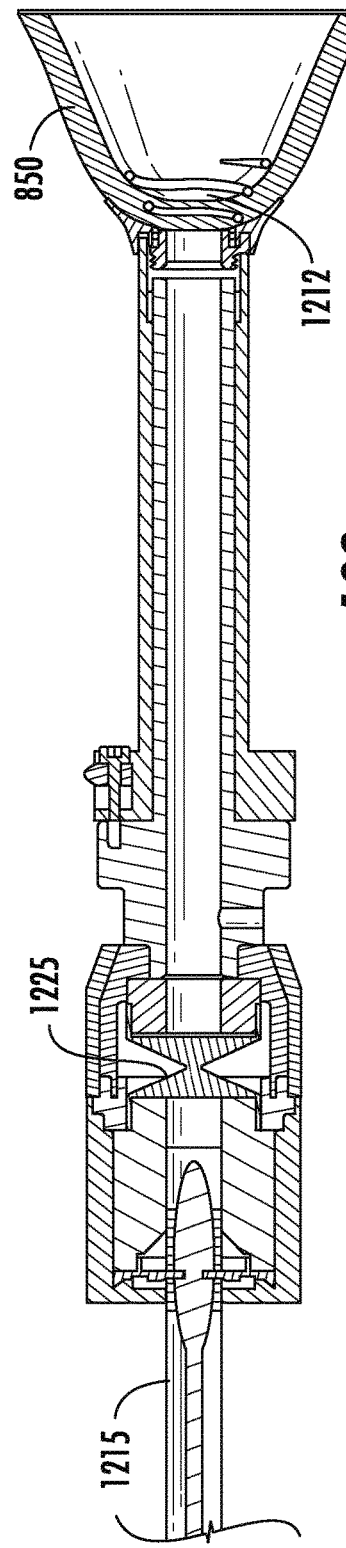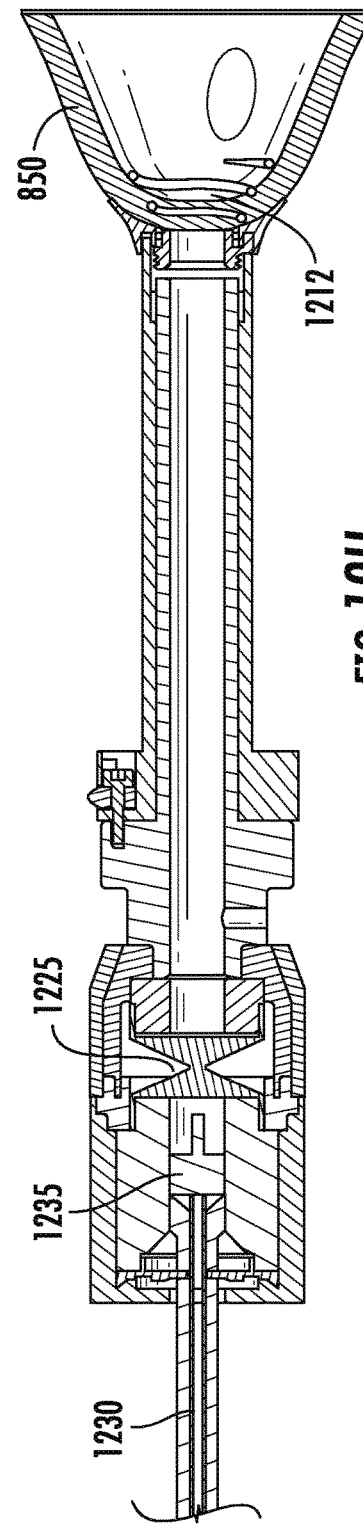

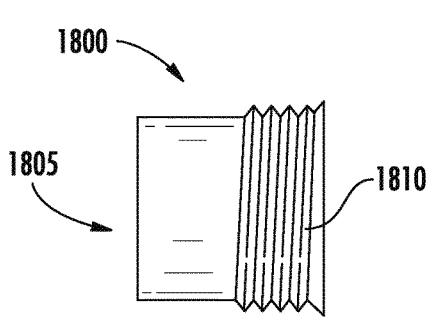
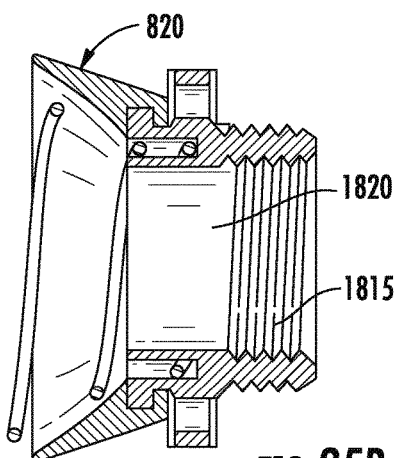
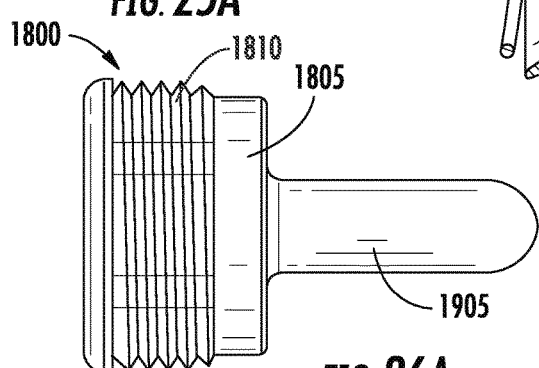
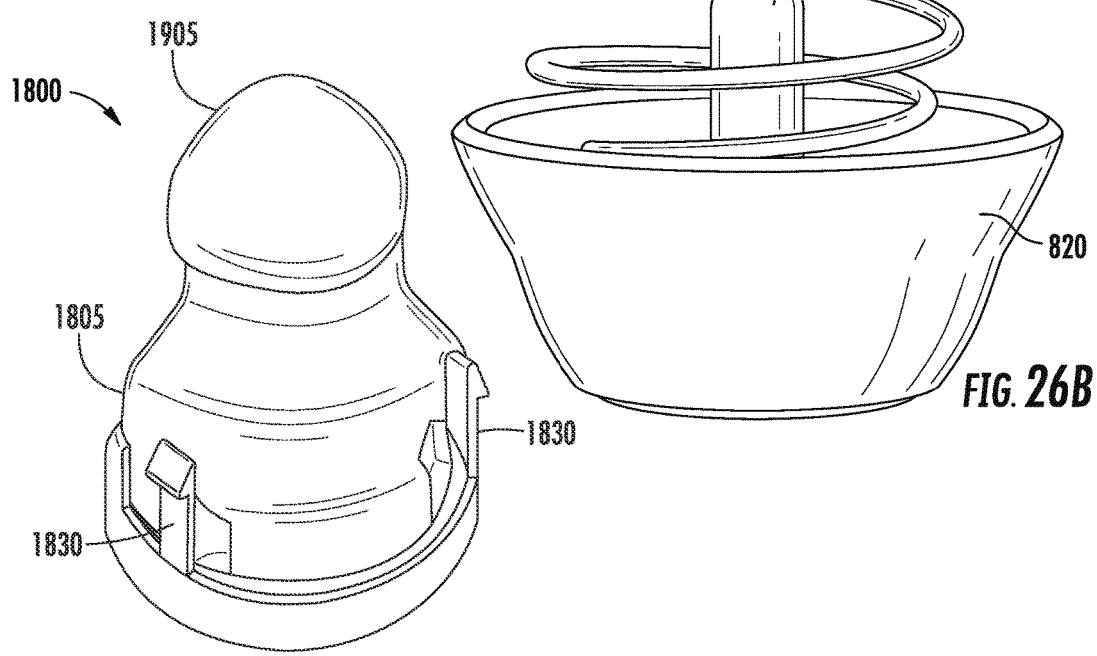
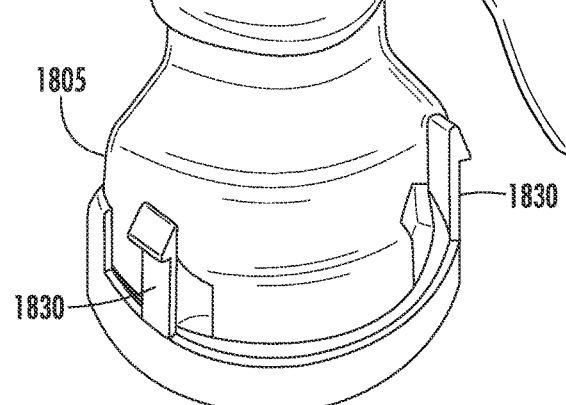
FIG. 25A
FIG. 25B
FIG. 26A
FIG. 26B
FIG. 26C

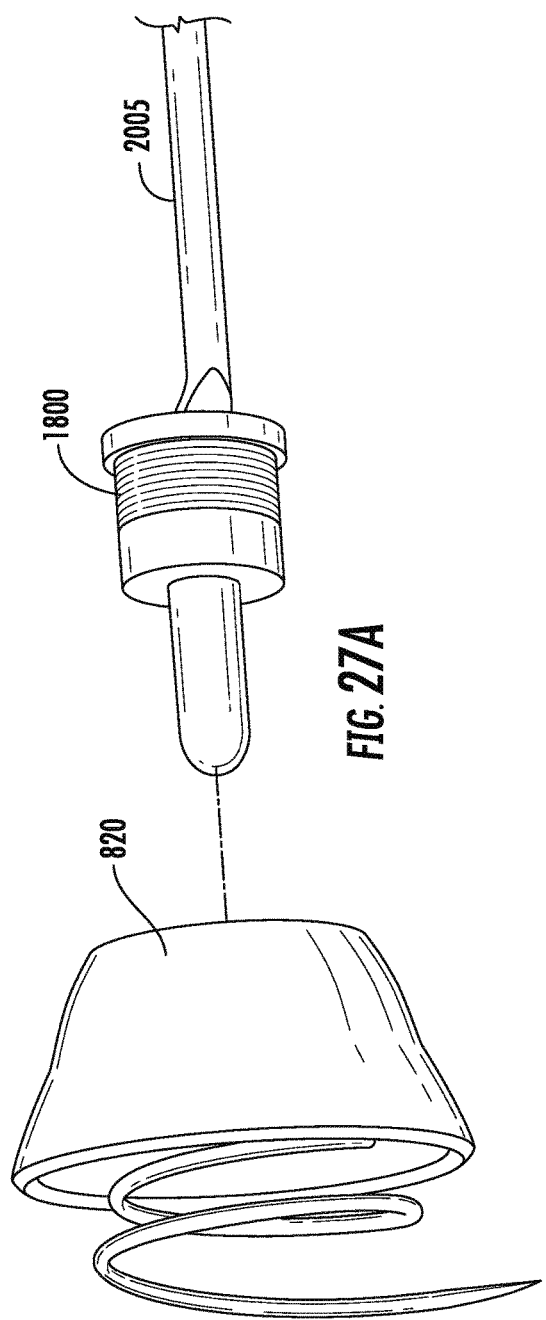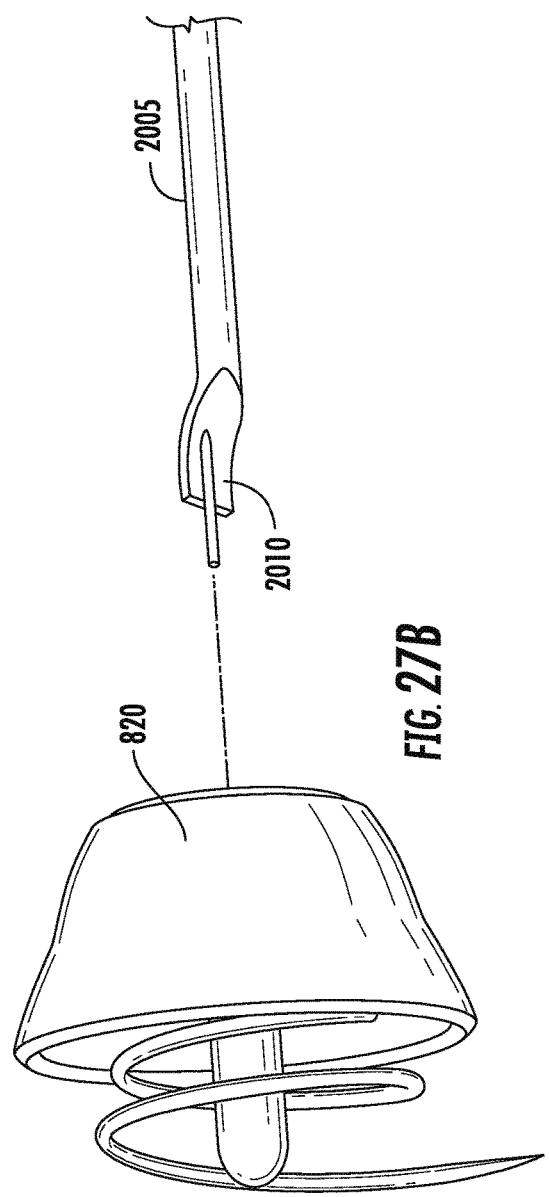

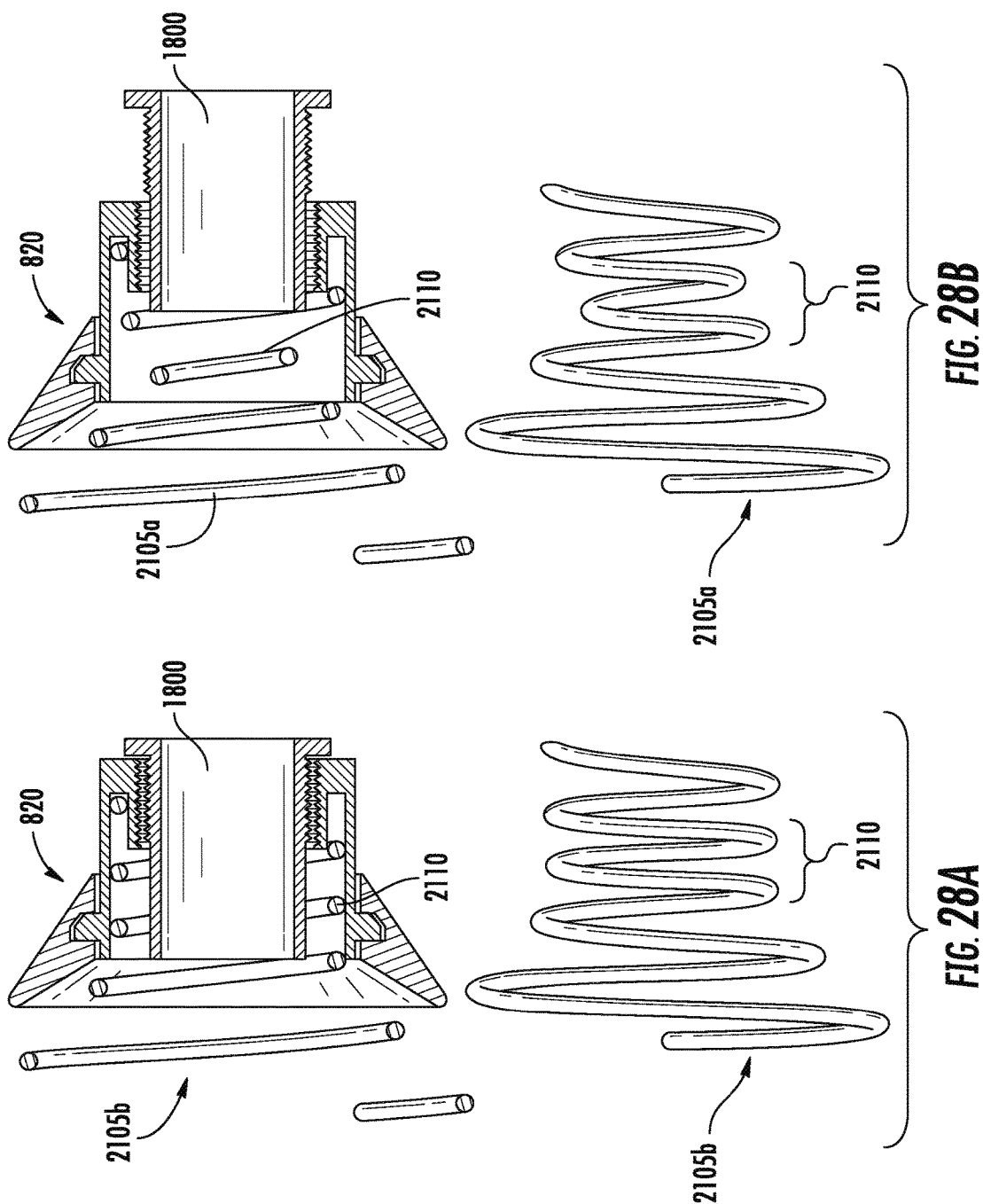

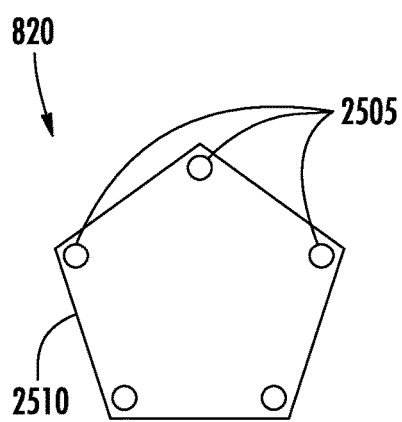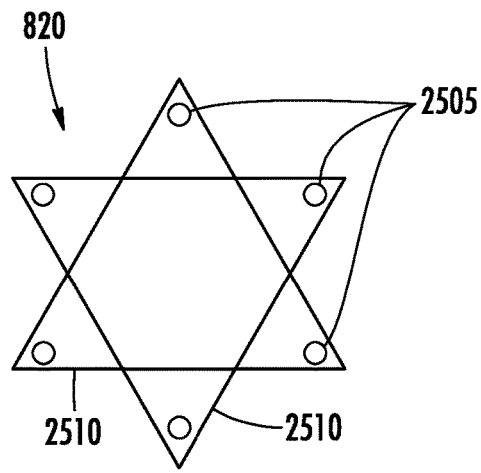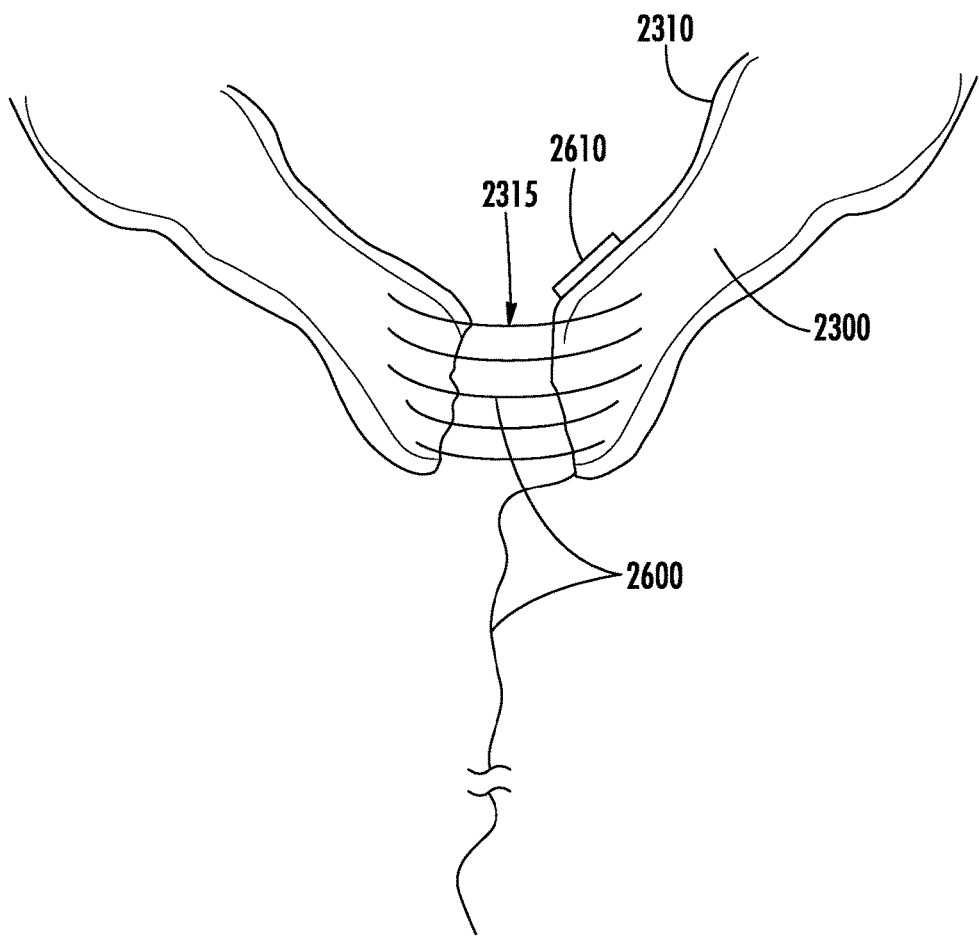

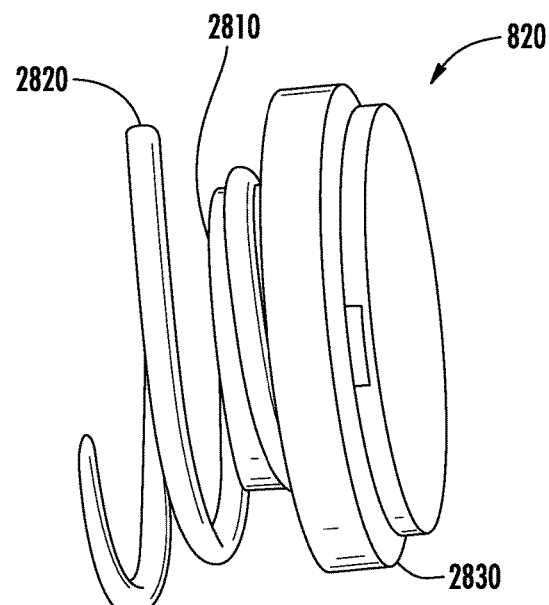
FIG. 35A
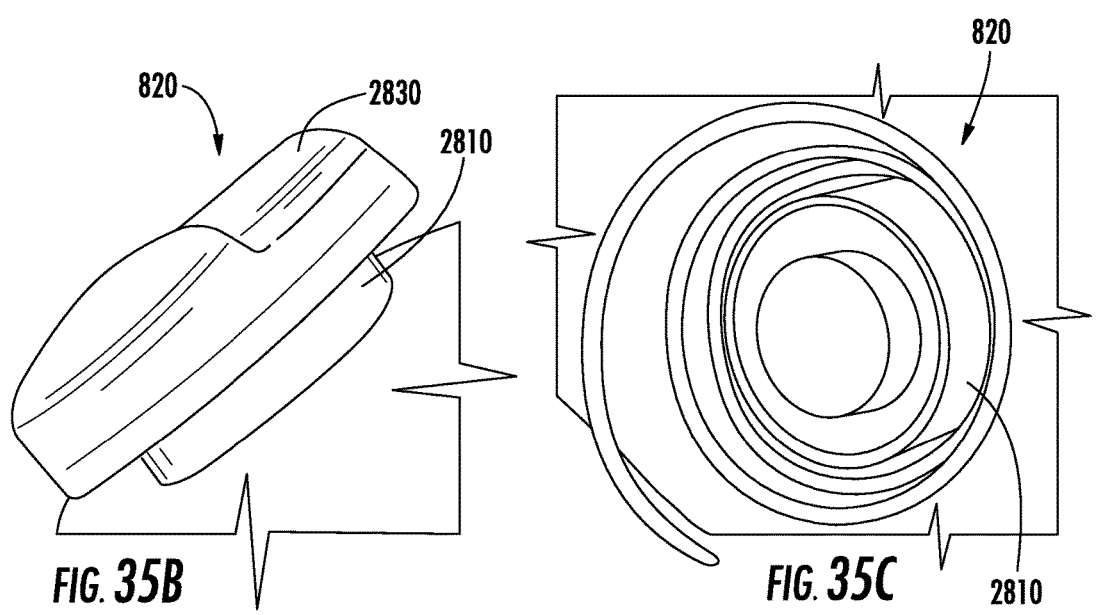
FIG. 35B
FIG. 35C

SYSTEMS AND METHODS FOR PERCUTANEOUS ACCESS, STABILIZATION AND CLOSURE OF ORGANS

CROSS REFERENCE TO RELATED APPLICATIONS

This application is a continuation of PCT Application No. PCT/US2014/013195 filed Jan. 27, 2014 which claims priority to U.S. Provisional Application Ser. No. 61/756,885 filed Jan. 25, 2013, 61/777,796 filed Mar. 12, 2013, 61/819,237 filed May 3, 2013, and 61/835,712 filed Jun. 17, 2013, the entire contents of which are incorporated by reference herewith.

FIELD OF THE INVENTION

This invention relates to devices and methods for creating, maintaining, controlling, and closing a fluid communication between opposing surfaces of a tissue wall.

BACKGROUND OF THE INVENTION

In the human body, various organs contain fluids both in liquids and gaseous forms within tissue layers or cavities formed by tissue. These liquids may or may not be under pressure. The tissue walls around these cavities are normally designed to confine these liquids to specific areas of the body. Blood as in the heart and vasculature in order to preserve its volume and transport oxygen to tissue, gastric and intestinal fluids as in the stomach and intestines in order to transport remains of digestion out of the body after nutrients are absorbed, urine in the bladder in order to expel liquid waste from the body, fluid within the eye to maintain its shape and passage of light, are examples of such tissue fluid confining systems. During medical procedures within these cavities it is of extreme importance to control the fluid within. The most common example is cardiopulmonary bypass during open hearts surgery, although, in all procedures associated with the system above emphasis is placed on control of the fluid within the organ. For this control, sometimes extra space is required to conduct these interventions; therefore, highly invasive procedures may be required for surgery within these cavities, especially while maintaining organ function. The most complex example of these being beating heart surgery. For less invasive procedures, especially those within the vascular system, access ports or conduits which allow for fluid communication, control and tissue closure within the organ being repaired are therefore required.

The various conduit and port devices and systems described herein may be utilized as an accompaniment with any number of surgical procedures to gain access through a variety of possible tissues. For example, the conduit devices and systems may be utilized to provide fluid access across a tissue wall, such as, but not limited to, upon establishing an AAC, upon establishing a port for inter-ventricular repairs (e.g., valve repair, valve replacement, or ablation procedures, etc.), upon establishing valved and/or open conduits (including bypass conduits) to augment native blood vessels in order to treat a variety of vascular conditions (e.g., aortic valvular disease, congestive heart failure, left ventricle outflow tract obstructions ("LVOTO"), peripheral arterial obstructions, small vessel obstructions, etc.), upon providing a conduit across a urinary bladder wall, upon providing a conduit across a gall bladder wall, upon providing a conduit into a thoracic cavity, upon providing a conduit into an abdominal cavity, upon providing a conduit into a cecal cavity, upon providing access into the cornea or eye walls, or upon providing access across or into any other tissue wall structures. Accordingly, the conduit devices and systems described herein may be utilized with any of the aforementioned procedures and/or to gain access through any of the aforementioned tissue walls.

Because of the importance of heart function and the complexities associated to this pressurized system, some of the most complex procedures associated with bodily fluids are performed on this organ. Several of these procedures would benefit from a conduit or port which can maintain a fluid tight seal with tissue surfaces.

Heart valve replacement is the most common open heart cardiovascular surgery procedure, currently most heart valve repair or replacement surgeries are conducted on a heart at rest under cardiopulmonary bypass through a large median sternotomy. This surgery is highly invasive, and therefore, the population that may survive such a procedure is limited to those who are strong surgical candidates. In recent years valves for minimally invasive deployment through the femoral artery or apex of the heart have been developed. These valves may be used in patients that would under other conditions be deemed non-candidates. The use of these valves may also in the future reduce complications associated with cardiopulmonary bypass and large incisions in surgical candidates. For those procedures through the apex of the heart it has been shown that bleeding complications are directly associated with 50% increased mortality, therefore, and access conduit or port which would reduce bleeding complications, decrease incision size and simplify closure would be of great benefit.

Another procedure that would benefit from a fluid tight conduit or port into the heart would be the construction of an alternative conduit between the left ventricle and the aorta (an apicoaortic conduit, or AAC). This procedure creates a double-outlet left ventricle (LV) to treat a variety of complex congenital LV outflow obstruction (fibrous tunnel obstruction, aortic annular hypoplasia, tubular hypoplasia of the ascending aorta, and patients with diffuse septal thickening, severe LV hypertrophy and a small LV cavity) as well as adult-onset aortic stenosis in patients with complicating preoperative conditions (previous failed annular augmentation procedures, previous infection, previous CABG with patent anterior internal mammary artery grafts, and a porcelain ascending aorta). However, the AAC insertion procedure has been poorly accepted, with or without cardiopulmonary bypass, has not been as technically straightforward as direct aortic valve replacement. Nonetheless, several studies have demonstrated that AAC insertion successfully lessens the LV-aortic pressure gradient, preserves or improves ventricular function and maintains normally distributed blood flow through the systemic and coronary circulation.

While there have been several techniques described, the most commonly employed method is the lateral thoracotomy approach with placement of the AAC to the descending aorta or a median sternotomy. The current techniques and technology available to perform AAC insertion were originally designed to be performed on-pump; either with an arrested or fibrillating heart, therefore, highly invasive. While off-pump cases have been described, they can be technically difficult due to the shortcomings of presently available conduits and systems for installing such conduits. For example, because existing conduits require the use of sutures to reliably secure the connector in place, it is often difficult for surgeons or other clinicians to insert such sutures reliably in active cardiac and/or vascular tissue.

Some devices and methods have been devised to install an AAC conduit, such as those described generally in U.S. Patent Publication No. 2006/0089707 which is hereby incorporated by reference herein in its entirety. However, these AAC conduit devices and installation systems rely on the use of a flexible flange that is inserted through a pre-defined aperture in the ventricular apex. Thus, such methods require the use of a haemostatic device (such as an occlusion balloon and/or "umbrella" device) to prevent blood loss from the aperture during installation of the AAC conduit. Other apical conduit devices are described in U.S. Pat. No. 7,846,123, which is also hereby incorporated by reference in its entirety.

Accordingly, improved beating heart fluid tight conduits for heart surgery as such described herein, are desirable.

SUMMARY OF THE INVENTION

Various embodiments of the present invention provide an improved system and method for the insertion of a conduit connector or port (such as an AAC conduit) that will significantly simplify the in vivo beating heart treatment of cardiac patients. The connector, port or conduit may be inserted into the beating cardiac apex or other tissue walls (such as other areas of the heart including the anterior, lateral, posterior walls of the left or right ventricle, the left or right atrium, the aortic wall, ascending, transverse, or descending, or other blood vessel walls), such that it may effectively reduce and/or negate the detrimental effects of both cardio-pulmonary by-pass (CPB) and global cardiac ischemia. Additionally, embodiments of such conduits that may be capped as ports and may be used as an access site for intravascular and intracardiac procedures such as valve repair or replacement. Various embodiments of the present invention may also provide general conduit devices (and systems for implanting) suitable for establishing fluid communication between opposing surfaces of tissue walls in a variety of applications, including the establishment of a fluid conduit through the tissue wall of a mammalian stomach or urinary bladder.

In one exemplary embodiment, a system is provided for implanting a conduit device in a tissue wall having a first surface and an opposing second surface. According to some embodiments, the system comprises an outer tube defining a guide aperture extending axially through the outer tube and an attaching device extending from a distal end of said outer tube. The attaching device is configured for advancing along a helical path at least partially through the tissue wall such that at least a portion of the attaching device becomes disposed substantially between the first surface and the opposing second surface of the tissue wall when the outer tube is rotated relative to the first surface of the tissue wall. The attaching device, in some system embodiments, comprises at least one of a helical static coil and a helical elastic spring having a sharpened distal end adapted for piercing the tissue wall as the outer tube is rotated relative to the first surface of the tissue wall. According to some such embodiments, the attaching device may define a radially-expanding helix as the attaching device extends away from the distal end of the outer tube. In such configuration the insertion of the radially expanding helix within the tissue will create inward pressure or contraction of said tissue within the circumference of the coil.

In some embodiments, the system also comprises a ring or flange operably engaged about an outer surface of the outer tube and configured for cooperating with the attaching device such that at least a portion of the tissue wall is secured between the attaching device and the ring so as to operably engage said outer tube with the tissue wall. In some embodiments, various system components, such as the outer tube and the ring, may be configured to conform to and/or establish a substantially fluid-tight seal with at least a portion a surface of the tissue wall. In some embodiments, the system may be configured to cooperate and/or operably engage a tissue wall comprising a substantially curved tissue wall. According to some such embodiments, the ring may comprise a frusto-conical assembly or flange configured for receiving at least a portion of the substantially curved tissue wall so as to form a substantially fluid-tight seal between the frusto-conical assembly and the tissue wall.

In certain embodiments, the invention provides a system for sealing a device attached to a tissue surface comprising: a tissue attaching device having an outer base ring defining an opening therethrough and a distally projecting tissue attachment element; and an annular sealing flange distally attached to the outer base ring outside the tissue attachment element defining a first circumference and distally projecting at an inward angle to define a second circumference for interfacing with the tissue surface surrounding the attachment element, wherein the second circumference is smaller than the first circumference to create a fluid tight seal that is strengthened when fluid pressure is increased inside the base ring. In certain embodiments, the tissue attachment element is a coil, and the tissue is a heart.

In certain embodiments, the invention provides a system for sealing a device attached to a tissue surface comprising: a tissue attaching device having an outer base ring defining an opening therethrough and a distally projecting tissue attachment element; and an annular sealing flange distally attached to the outer base ring inside the tissue attachment element defining a first circumference and distally projecting for interfacing with the tissue surface to create a fluid tight seal. In certain embodiments, the tissue attachment element is a coil, and the tissue is a heart.

In certain embodiments, the invention provides a tissue sealing device comprising a tissue attaching device having an outer base ring defining an opening therethrough and a distally projecting tissue attachment coil defining a first pitch region and distally projecting to define a second pitch region, wherein the second pitch is larger than the first pitch to create increased inward pressure on the tissue as the coil is rotatingly inserted into the tissue.

In certain embodiments, the outer base ring further comprises an annular sealing flange distally attached to the outer base ring outside the tissue attachment element defining a first circumference and distally projecting at an inward angle to define a second circumference for interfacing with the tissue surface surrounding the attachment element, wherein the second circumference is smaller than the first circumference to create a fluid tight seal that is strengthened when fluid pressure is increased inside the base ring.

In certain embodiments, the invention provides a method for installing an apical attaching device with a transapical port into a patient, comprising:

a. assessing the patient's viability for installation of the apical attaching device by determining an Index of Tissue Elasticity (ITE) of the cardiac tissue, by using measured local tissue curvature radius (r), tissue thickness (t) and ventricular pressure (p) to calculate local stress ($\sigma$) with formula:

$$\sigma_\theta = \frac{pr}{t}; \tag{I}$$

and using measured strain field value ($\in_o$) and calculated local stress ($\sigma$) to calculate the elasticity (E) with formula:

$$\in_{\sigma} = \frac{1}{E}\left(\left(r\frac{d\sigma_y}{dr} + \sigma_y\right) - v\sigma_y\right) \quad (III)$$

to derive an ITE of the apex of the patient's heart to assess; and b. installing the transapical port in the patient when the ITE is within a clinically acceptable deviation from an average ITE observed in a healthy population.

In certain embodiments, the invention provides a system for accessing a tissue wall comprising: a tube with an inner and outer lumen; a dilator with an expandable balloon on its distal end; wherein the system is configured to be delivered over a guide wire, wherein the balloon is configured to access the tissue in a compressed state and to be inflated to increase orifice size and allow for access of the tube. In certain embodiments, the system further comprises a coiled implant. In certain embodiments, the coiled implant is compressed axially. In certain embodiments, the tube is expandable, and/or steerable.

In some embodiments, the system further comprises an inner tube configured for insertion into the guide aperture defined by the outer tube. According to such embodiments, the inner tube defines a conduit aperture extending axially therethrough. Furthermore, in some such embodiments, the outer tube may comprise a first securing device operably engaged with a proximal end of the outer tube and the inner tube may comprise a complementary second securing device operably engaged with a proximal end of said inner tube. Thus, according to such embodiments, the second securing device may be configured for selectively operably engaging the first securing device so as to operably engage the inner tube with the outer tube to install and maintain the conduit.

In some embodiments, the system may also comprise a coring or piercing device configured for advancing through the conduit aperture defined by the inner tube and through the tissue wall to define an aperture therein. The coring or piercing device may be further configured for carrying the inner tube through the aperture such that the inner tube extends at least partially through the aperture so as to establish fluid communication between the first and second surfaces of the tissue wall. In the embodiments associated with attaching devices including radially expanding helices, inward compression of the tissue will form a sealing surface against the outer surface in the inner tube.

Various other embodiments of the present invention provide a conduit system including an outer lumen, an inner lumen, and an attaching device. In other embodiments, a multiple access port device adapted for communication with at least one of an outer lumen, an inner lumen, or an attaching device of a conduit system is provided. In yet other embodiments, a system including an inner lumen that is collapsible is provided. Means for closing a conduit system are also provided, including a plug for insertion through an attaching device and a variable radius coiled member associated with an attaching device.

Various other embodiments of the present invention include an outer lumen configured for extension and contraction, as well as universal motion absorption. Further embodiments include an outer lumen comprising a collapsible diaphragm. Still further embodiments comprise expandable delivery systems for endovascular and percutaneous applications.

The various embodiments of the present invention may thus be configured for implanting a conduit device that is adapted for providing a conduit for a medical procedure. Such procedures may include, but are not limited to: bypass; cardiac valve repair or replacement; attachment of a ventricular assist device; establishment of an apicoaortic conduit (AAC) and combinations of such procedures.

Use of this conduit device, system, and method will significantly improve the ease and safety of conduit insertion (such as the implantation of AAC devices, for example). For example, various embodiments of the present invention may allow the outer tube to be securely operably engaged with the tissue wall (due at least in part to the cooperation of the attaching device and the ring) prior to the removal of a tissue core to define an aperture in the tissue wall. Thus, portions of the system disclosed herein may define a guide aperture extending axially through the outer tube for receiving a coring device that may be configured to be capable of efficiently removing and retrieving a tissue core while substantially simultaneously operably engaging an inner tube in the guide aperture so as to establish fluid communication between first and second opposing surfaces of the tissue wall. As persons of ordinary skill in the art will readily appreciate, the various embodiments of the present invention may also be used in a minimally invasive, endoscopically assisted approach.

BRIEF DESCRIPTION OF THE DRAWINGS

Figure 1:
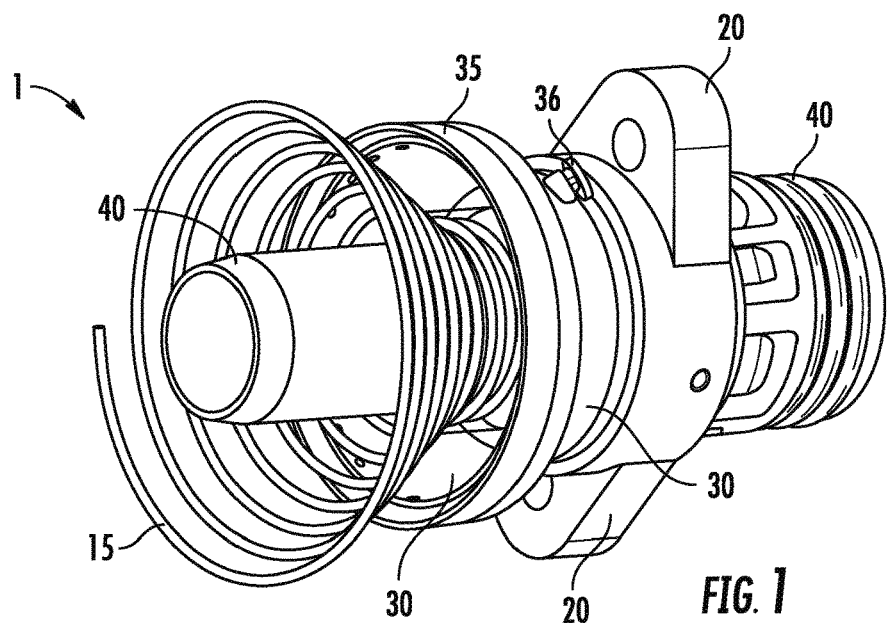

Having thus described various embodiments of the invention in general terms, reference will now be made to the accompanying drawings, which are not necessarily drawn to scale, and wherein:

FIG. 1 shows a non-limiting perspective view of an exemplary system for implanting a conduit device, according to one embodiment of the present invention.

Figure 2:
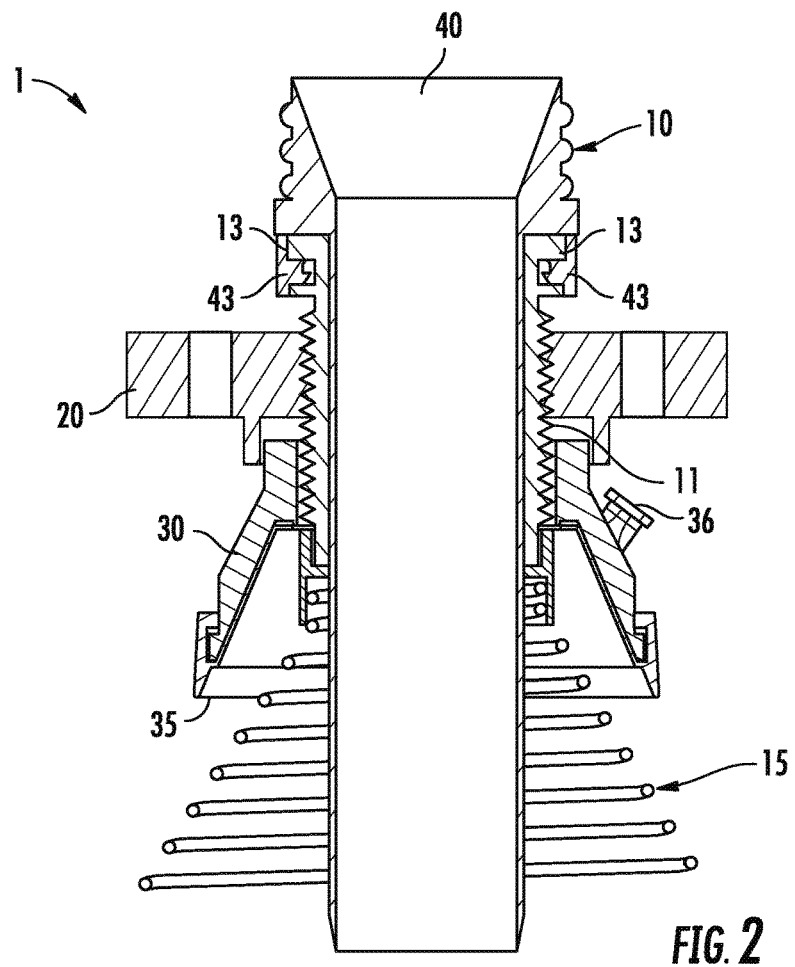

FIG. 2 shows a non-limiting side cross-sectional view of an exemplary system for implanting a conduit device, according to one embodiment of the present invention.

Figure 3:
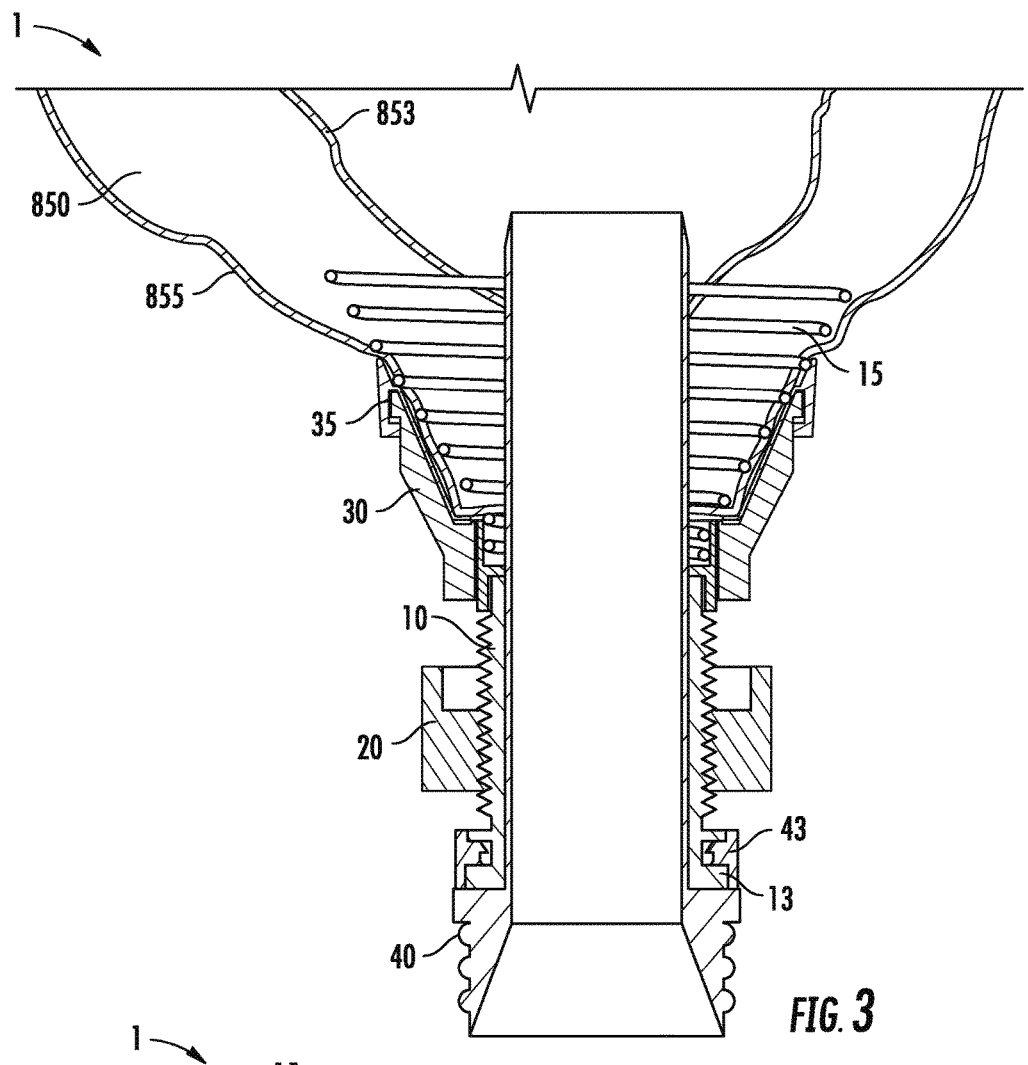

FIG. 3 shows a non-limiting side cross-sectional view of an exemplary conduit device implanted in a tissue wall, according to one embodiment of the present invention.

Figure 4:
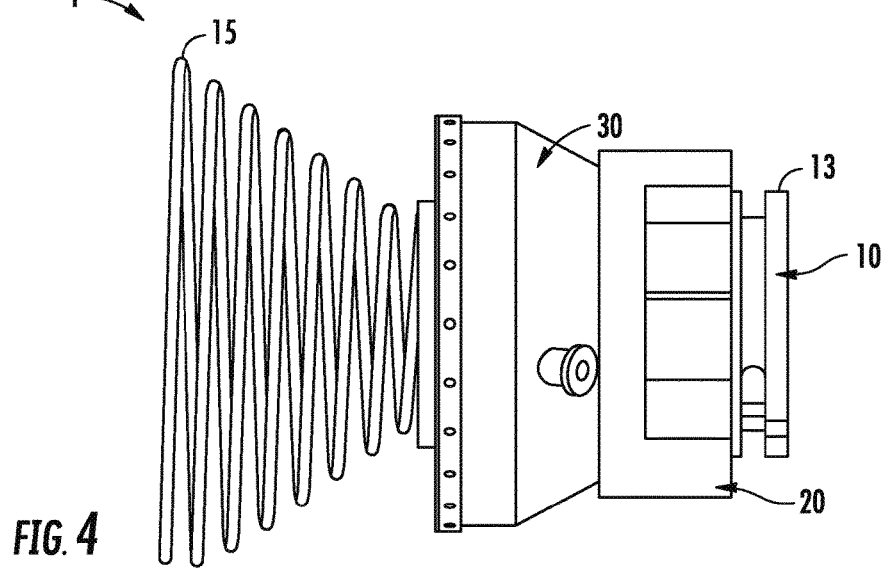

FIG. 4 shows a non-limiting side view of an exemplary system for implanting a conduit device, according to one embodiment of the present invention.

FIGS. 5A-5G show an exemplary set of views of the installation of a conduit device using an exemplary system, according to one embodiment of the present invention.

Figure 5A:
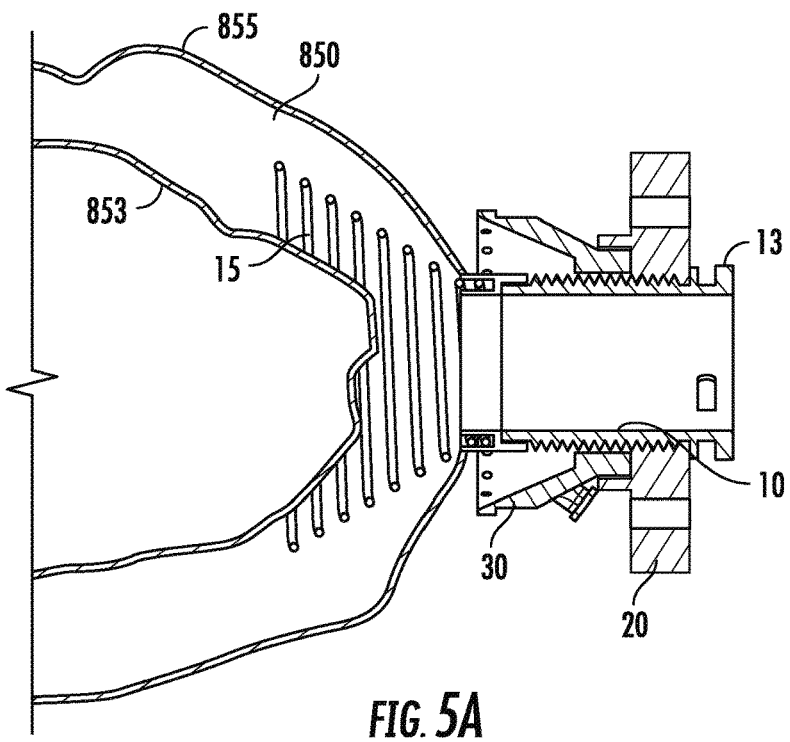

FIG. 5A shows a non-limiting side cross-sectional view of an exemplary system for implanting a conduit device comprising an attaching device at least partially implanted in a tissue wall, according to one embodiment of the present invention.

Figure 5B:
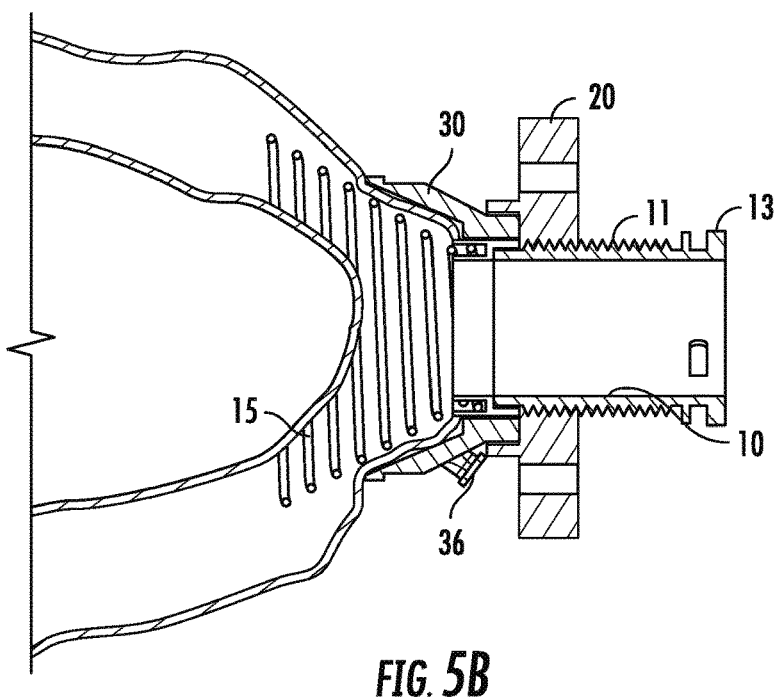

FIG. 5B shows a non-limiting side cross-sectional view of an exemplary system for implanting a conduit device comprising an attaching device and a ring cooperating to secure at least a portion of the tissue wall between the attaching device and the ring so as to operably engage said outer tube with the tissue wall, according to one embodiment of the present invention.

Figure 5C:
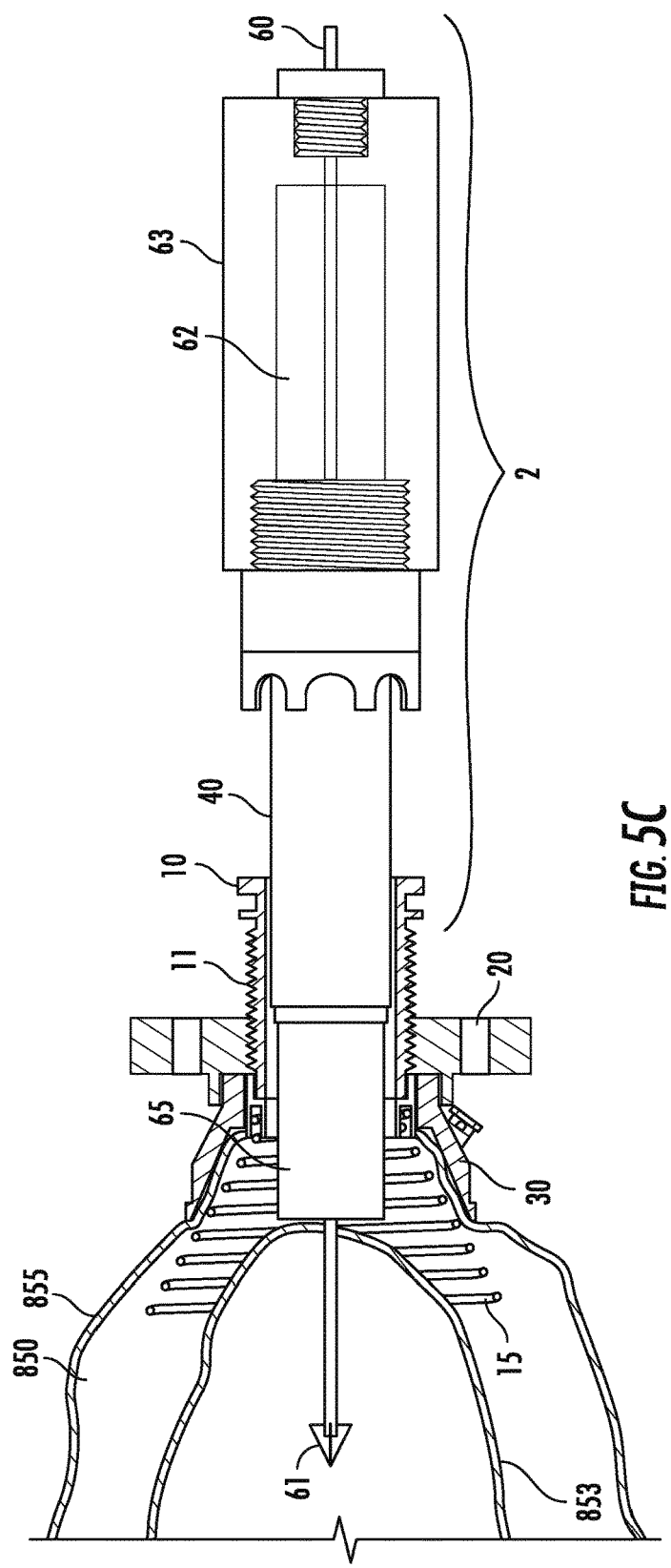

FIG. 5C shows a non-limiting side cross-sectional view of an exemplary system for implanting a conduit device comprising a coring device carrying an inner tube configured for insertion into a guide aperture defined by the outer tube, wherein the coring device is advanced at least partially through the tissue wall so as to remove a tissue core thereof, according to one embodiment of the present invention.

Figure 5D:
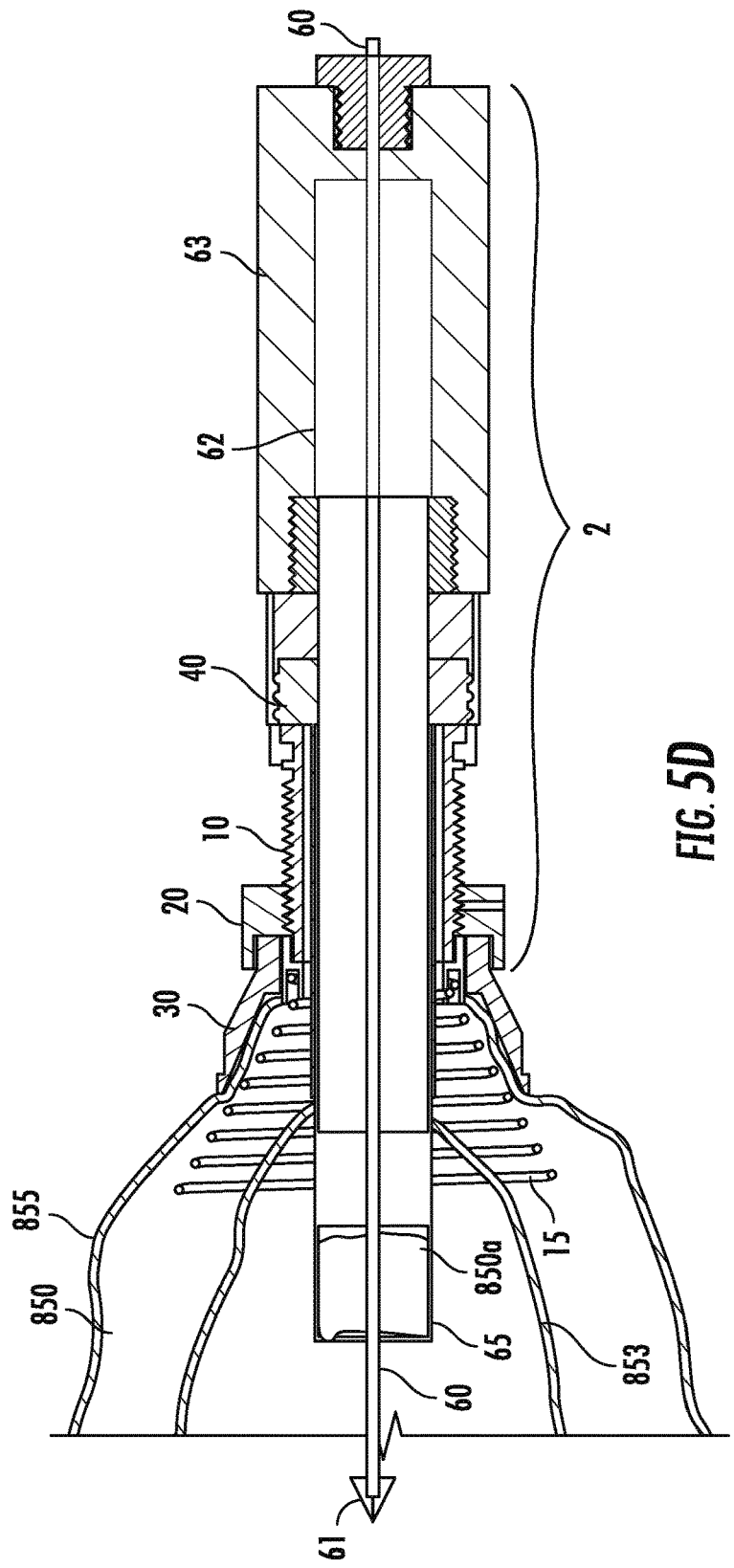

FIG. 5D shows a non-limiting side cross-sectional view of an exemplary system for implanting a conduit device comprising a coring device carrying an inner tube configured for insertion into a guide aperture defined by the outer tube, wherein the coring bore defined by the coring device contains a tissue core removed from the tissue wall, according to one embodiment of the present invention.

Figure 5E:
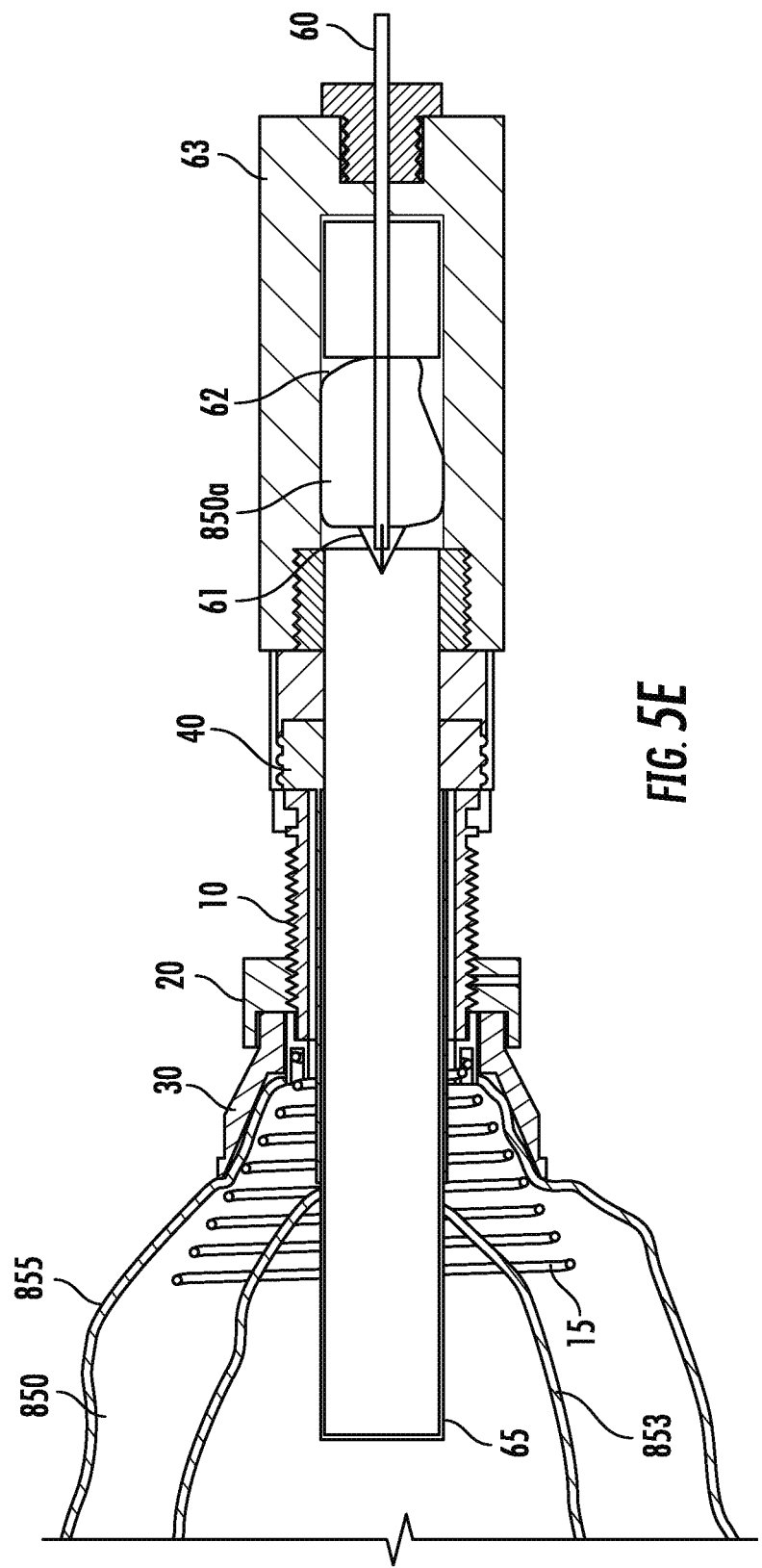

FIG. 5E shows a non-limiting side cross-sectional view of an exemplary system for implanting a conduit device comprising a coring device carrying an inner tube configured for insertion into a guide aperture defined by the outer tube, wherein a piercing rod is retracted through the coring bore after removal of the tissue core such that the tissue core is retrievable via a proximal end of the coring device, according to one embodiment of the present invention.

Figure 5F:
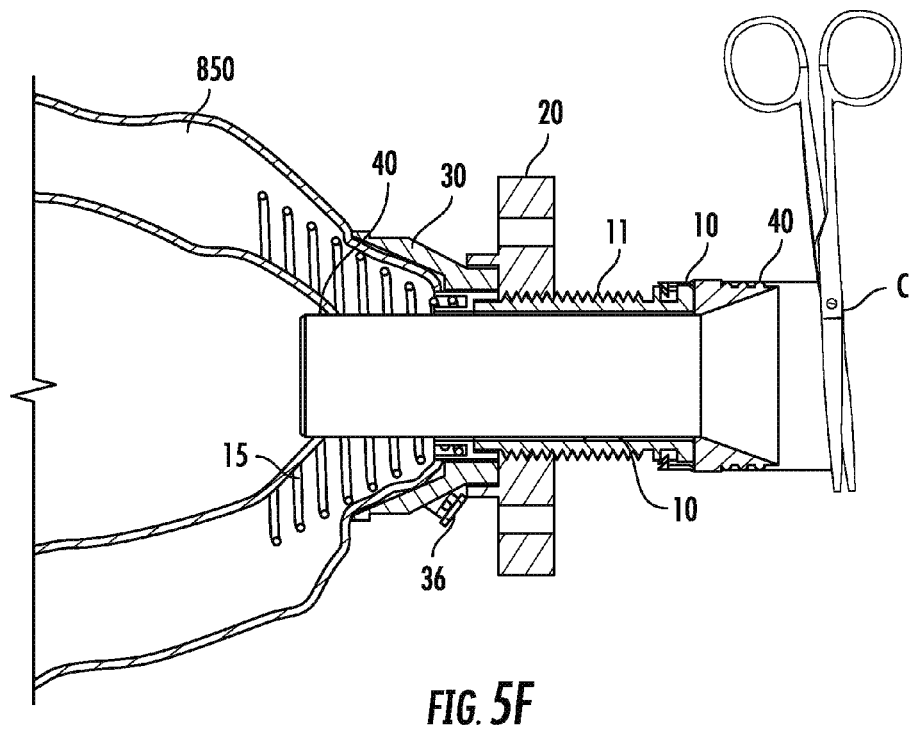

FIG. 5F shows a non-limiting side cross-sectional view of an exemplary system for implanting a conduit device, wherein the outer tube and inner tube are installed in the tissue wall so as to establish fluid communication between the first and second surfaces of the tissue wall, according to one embodiment of the present invention.

Figure 5G:
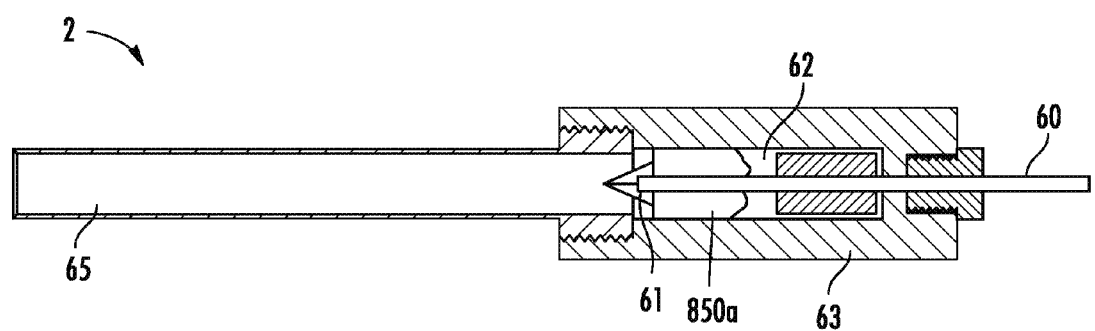

FIG. 5G shows a non-limiting side cross-sectional view of an exemplary coring device, wherein a handle operably engaged with a proximal end of the coring device contains a tissue core removed from the tissue wall by the coring device, according to one embodiment of the present invention.

FIG. 6 shows a non-limiting side view of an exemplary coring device carrying an inner tube configured for insertion into a guide aperture defined by the outer tube, according to one embodiment of the present invention.

FIG. 7 shows a non-limiting perspective view of an exemplary conduit device comprising an attaching device comprising a helical spring, according to one embodiment of the present invention.

Figure 8:
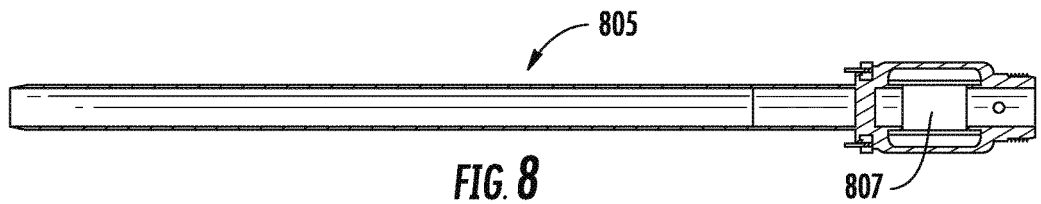

FIG. 8 shows a non-limiting cross-sectional view of an exemplary inner lumen for use with conduit systems described herein, according to one embodiment of the present invention.

Figure 9:
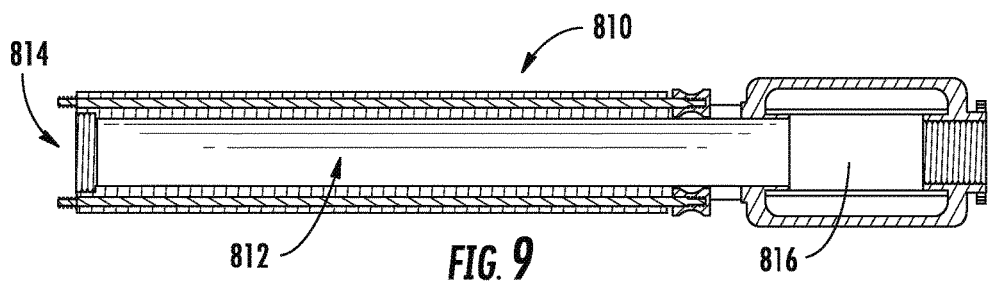

FIG. 9 shows a non-limiting cross-sectional view of an exemplary outer lumen for use with conduit systems described herein, according to one embodiment of the present invention.

Figure 10:
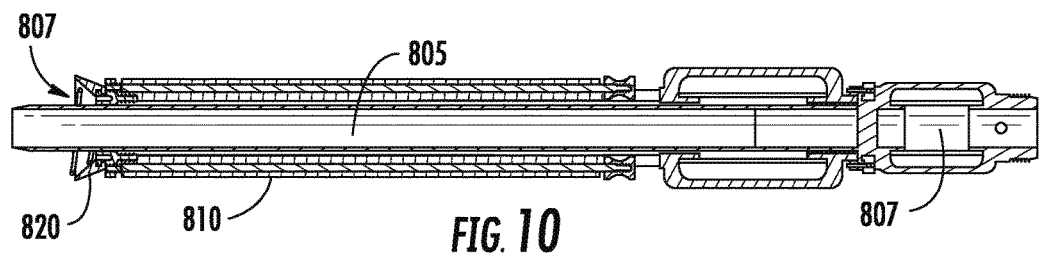

FIG. 10 shows a non-limiting cross-sectional view of an exemplary inner lumen inserted within an outer lumen for use with conduit systems described herein, according to one embodiment of the present invention.

Figure 11:
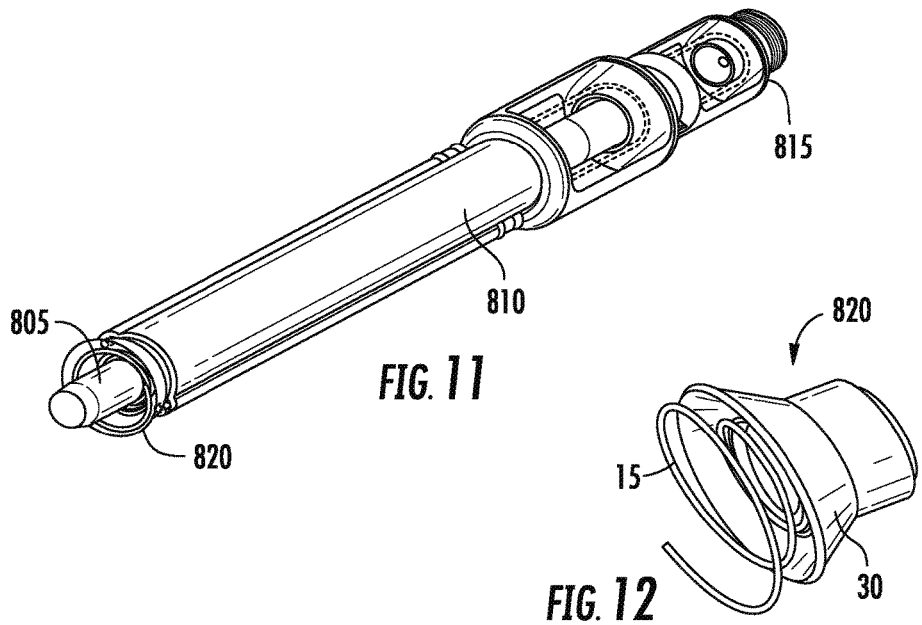

FIG. 11 shows a non-limiting perspective view of an exemplary inner lumen inserted within an outer lumen for use with conduit systems described herein, according to one embodiment of the present invention.

Figure 12:
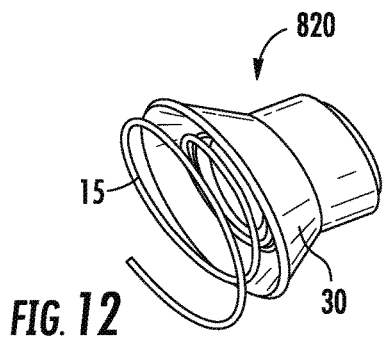

FIG. 12 shows a non-limiting perspective view of an exemplary attaching device for use with conduit systems described herein, according to one embodiment of the present invention.

Figure 13A:
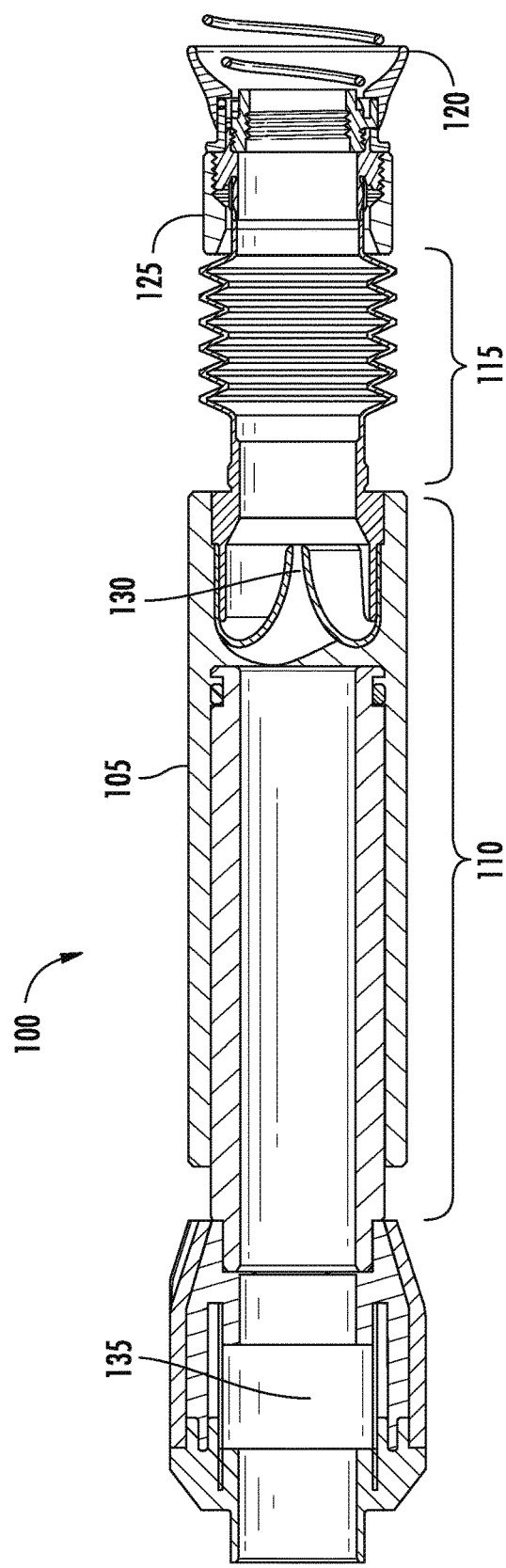
Figure 13B:
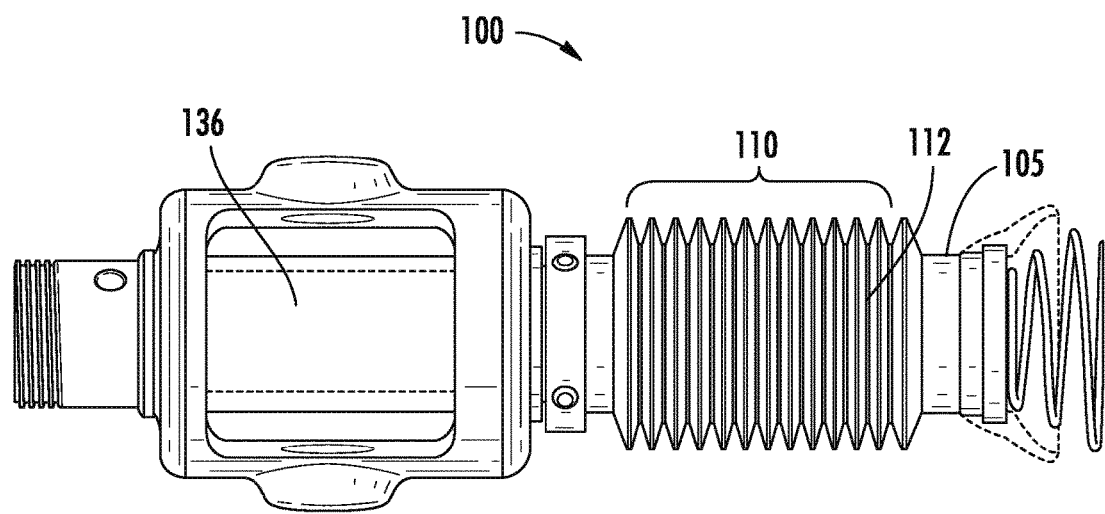
Figure 13C:
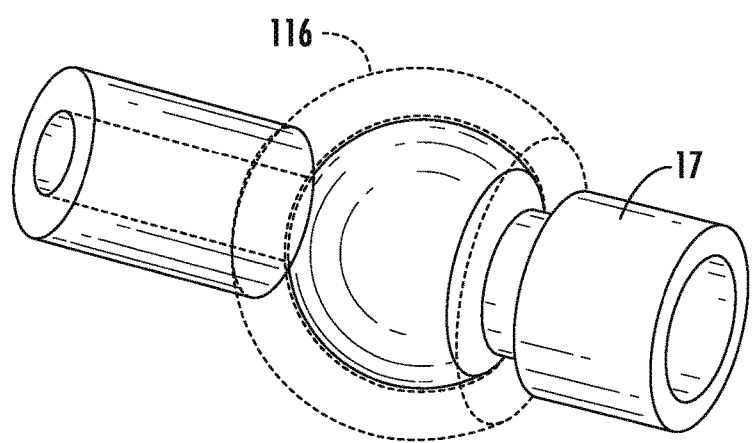

FIGS. 13A-13C show non-limiting cross-sectional, side, and perspective views of an example delivery system, in accordance with one embodiment of the invention with a motion absorption element.

Figure 14A:
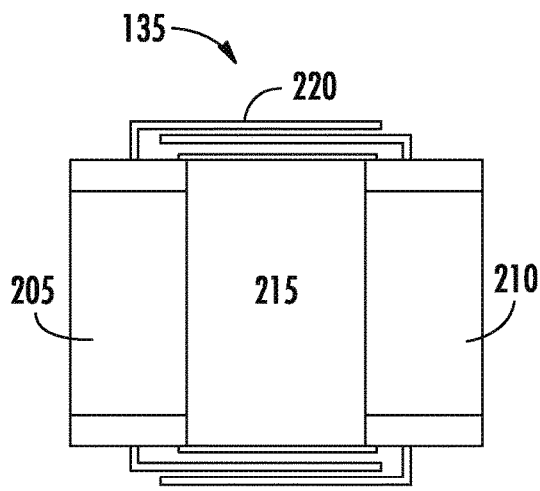
Figure 14B:
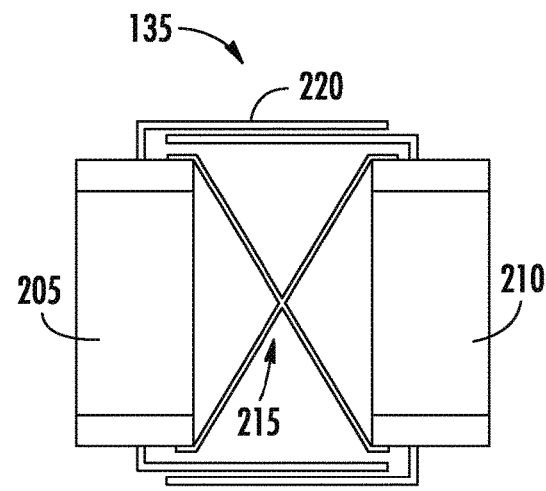
Figure 14C:
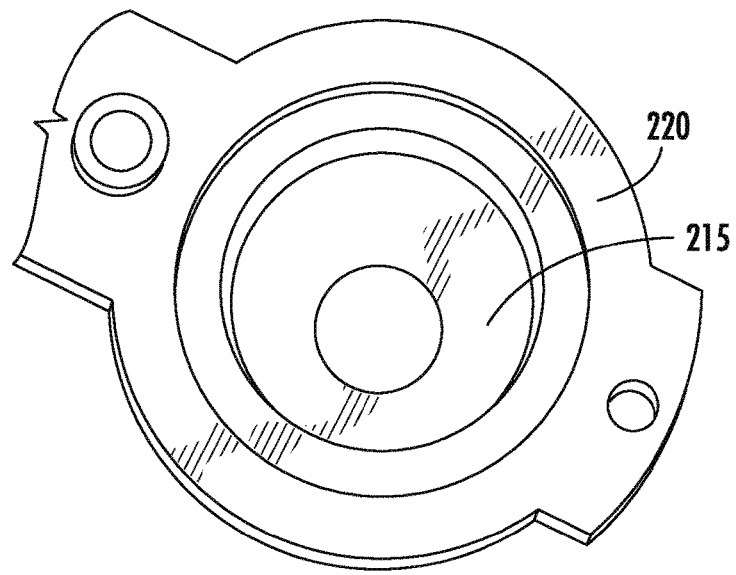

FIGS. 14A-14B show non-limiting cross-sectional views and FIG. 14C shows a non-limiting end view of a type of valve that is a rotation collapsible diaphragm valve, consisting of two or more conduits connected by a flexible conduit, in accordance with one embodiment of the invention.

FIG. 15 shows a non-limiting cross-sectional view of an exemplary embodiment of an inner tube constituted by a sheath with a duckbilled valve and a collapsible valve in its proximal end.

FIG. 16 shows a non-limiting cross-sectional view of an exemplary embodiment of an inner tube constituted by a sheath with a duckbilled valve and a collapsible valve in its proximal end. A dilator is placed within the lumen of the sheath in order to facilitate access into the tissue.

FIGS. 17A-17F show non-limiting cross-sectional views of an exemplary method for using a conduit system described herein, according to one embodiment of the present invention.

FIGS. 18A-18B show non-limiting side and cross-sectional views of a delivery system in accordance with one embodiment of the invention.

FIGS. 19A-19L show non-limiting cross-sectional and perspective views of the primary steps of an over-wire procedure that can benefit from using the various components described herein.

Figure 20:
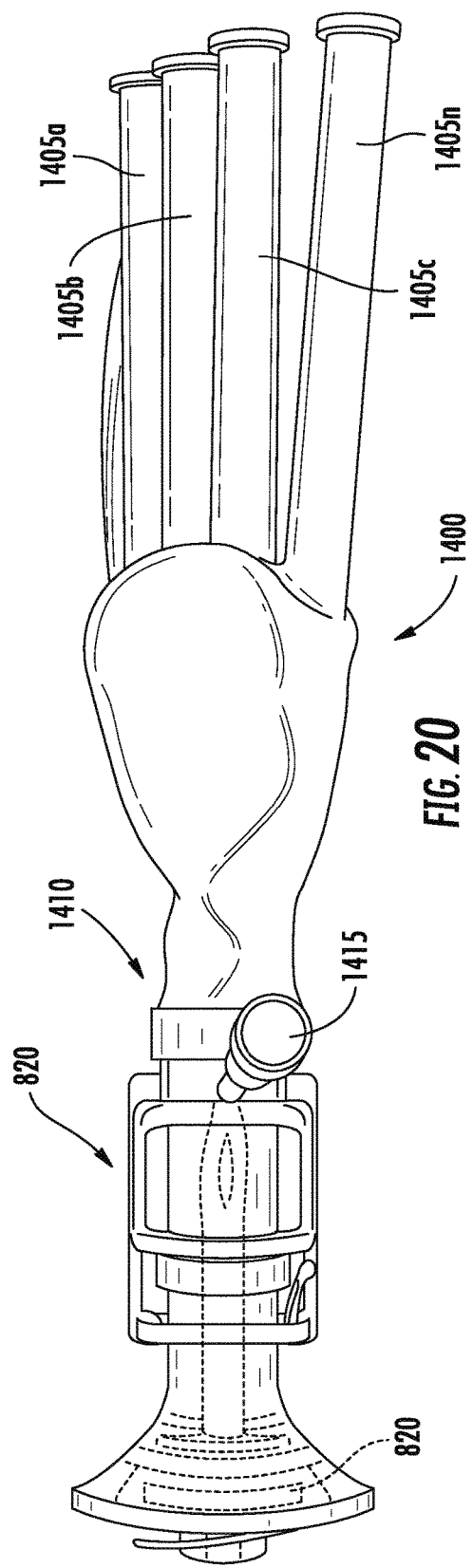

FIG. 20 shows a non-limiting perspective view of an exemplary multiple access port device for use with conduit systems described herein, according to one embodiment of the present invention.

Figure 21A:
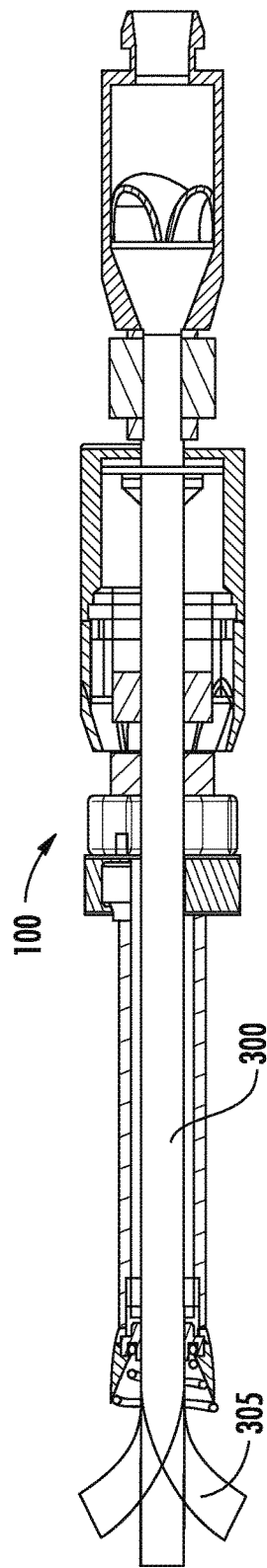
Figure 21B:
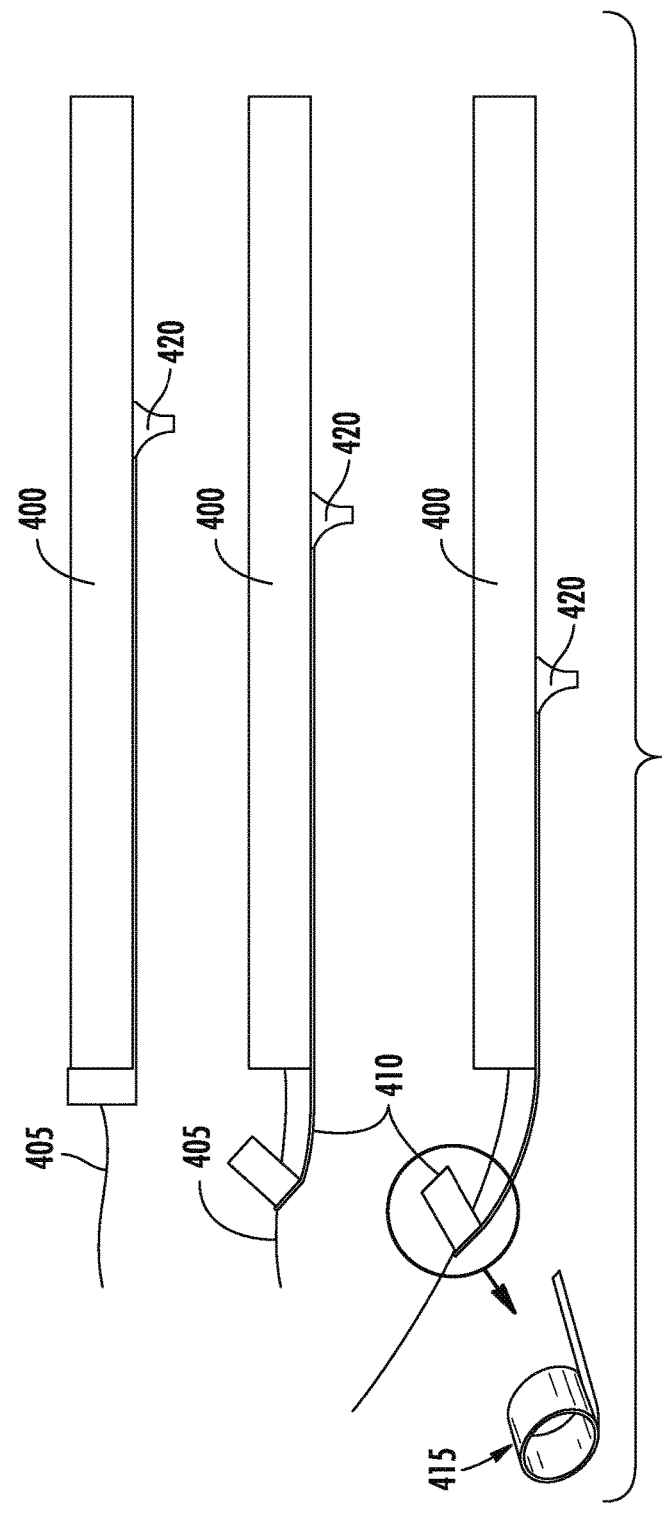

FIG. 21A shows a non-limiting cross-sectional view of an example delivery system having a lumen with a steerable tip, in accordance with one embodiment of the invention. FIG. 21B shows non-limiting diagrams of an example lumen with a steerable tip, according to one embodiment of the invention.

FIGS. 22A-22D show non-limiting perspective and side views of an exemplary collapsible inner lumen for use with conduit systems described herein, according to one embodiment of the present invention.

Figure 23A:
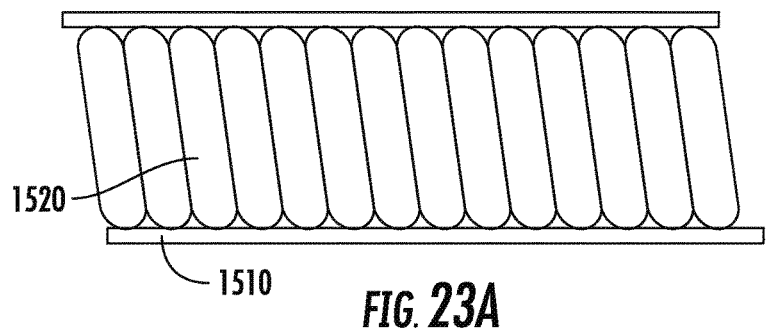
Figure 23B:
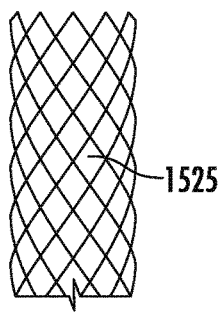
Figure 23C:
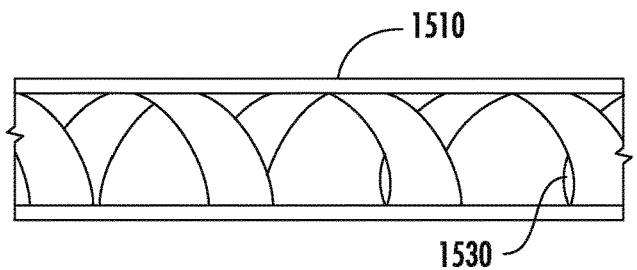

FIGS. 23A-23C show non-limiting side views of exemplary collapsible inner lumens for use with conduit systems described herein, according to embodiments of the present invention.

Figure 24B:
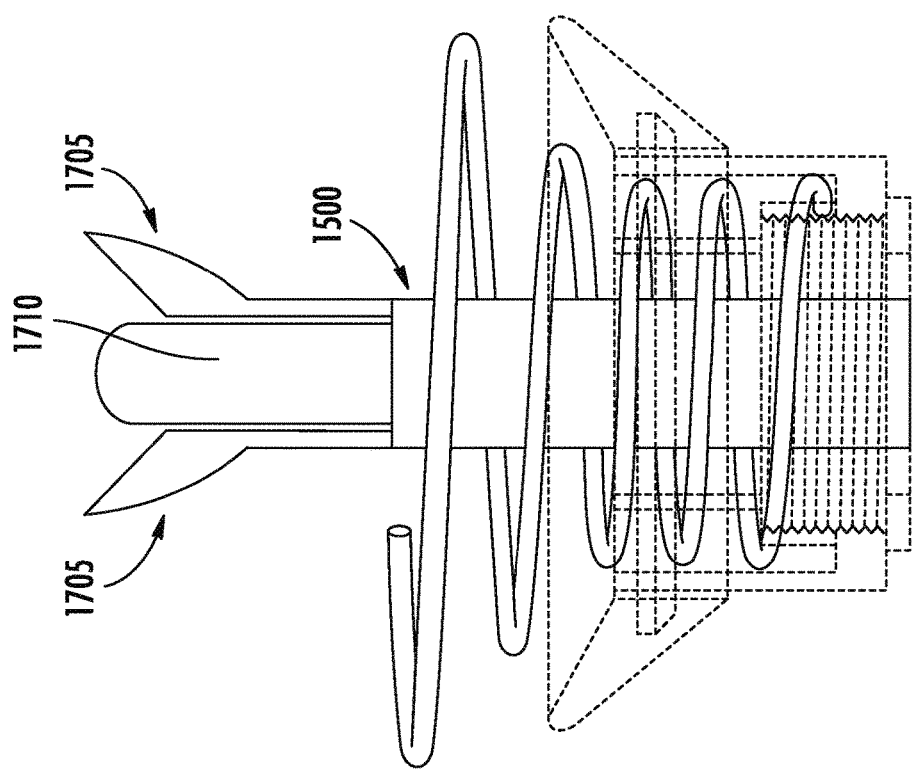
Figure 24A:
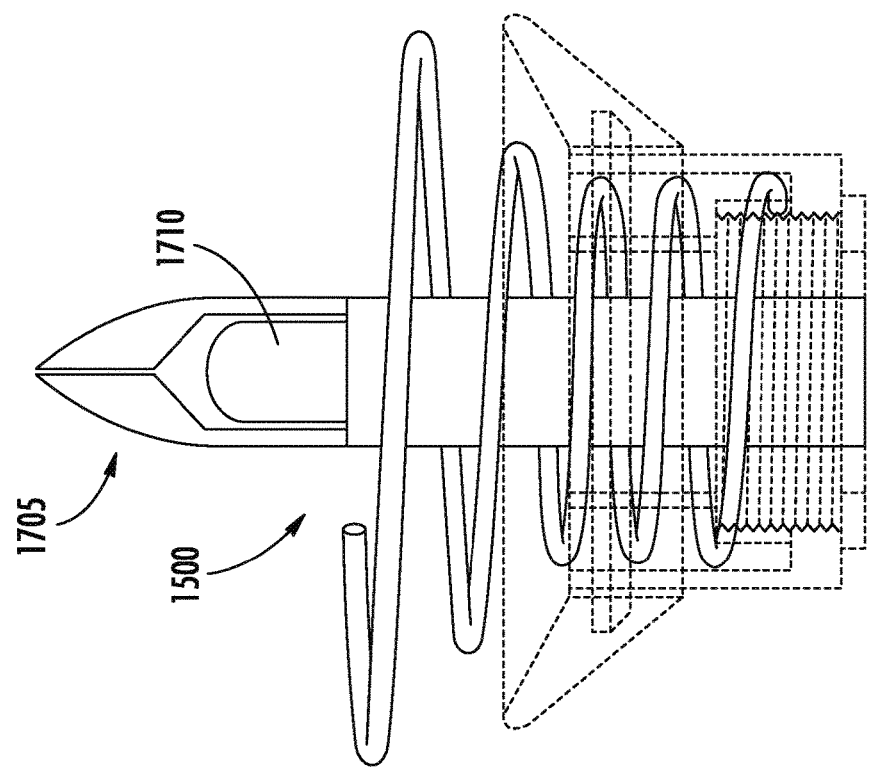

FIGS. 24A-24B show non-limiting side views of an exemplary collapsible inner lumen having a flexible tip for use with conduit systems described herein, according to one embodiment of the present invention.

FIGS. 25A-25B show non-limiting side views of an exemplary plug for use with an attaching device described herein, according to one embodiment of the present invention.

FIGS. 26A-26C show non-limiting side and perspective views of exemplary plugs for use with an attaching device described herein, according to embodiments of the present invention.

FIGS. 27A-27B show non-limiting perspective views of an exemplary delivery instrument for securing a plug to an attaching device described herein, according to one embodiment of the present invention.

FIGS. 28A-28B show non-limiting cross-sectional and side views of exemplary variable radius coiled members for use with an attaching device described herein, according to embodiments of the present invention.

Figure 29A:
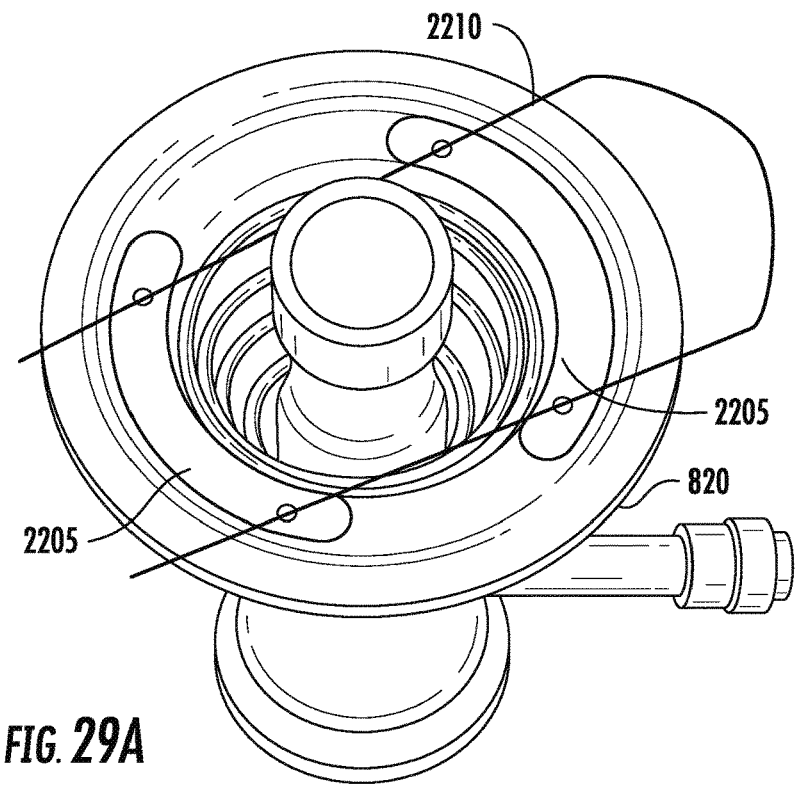
Figure 29B:
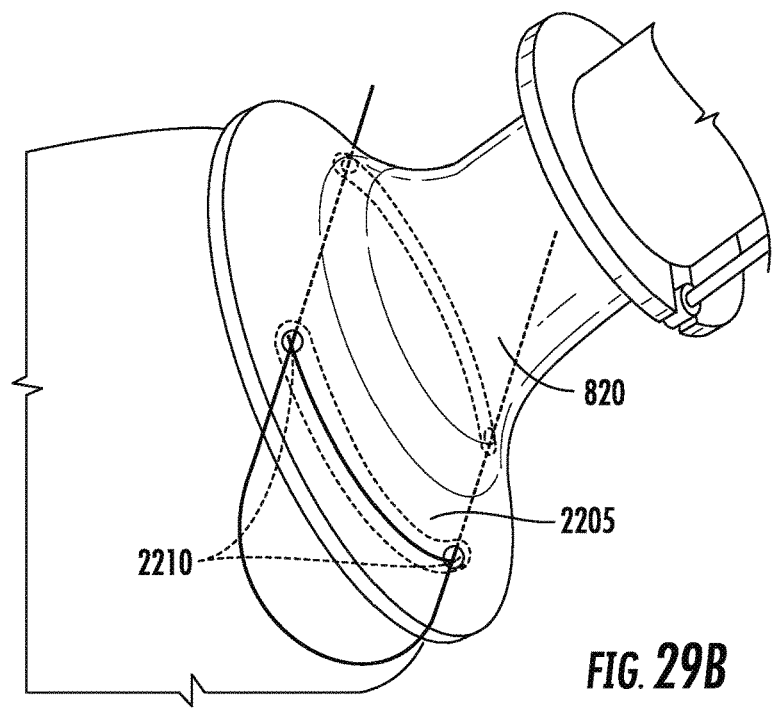

FIGS. 29A-29B show non-limiting perspective views of an exemplary attaching device including pledgets and sutures for use with conduit systems described herein, according to one embodiment of the present invention.

Figure 30A:
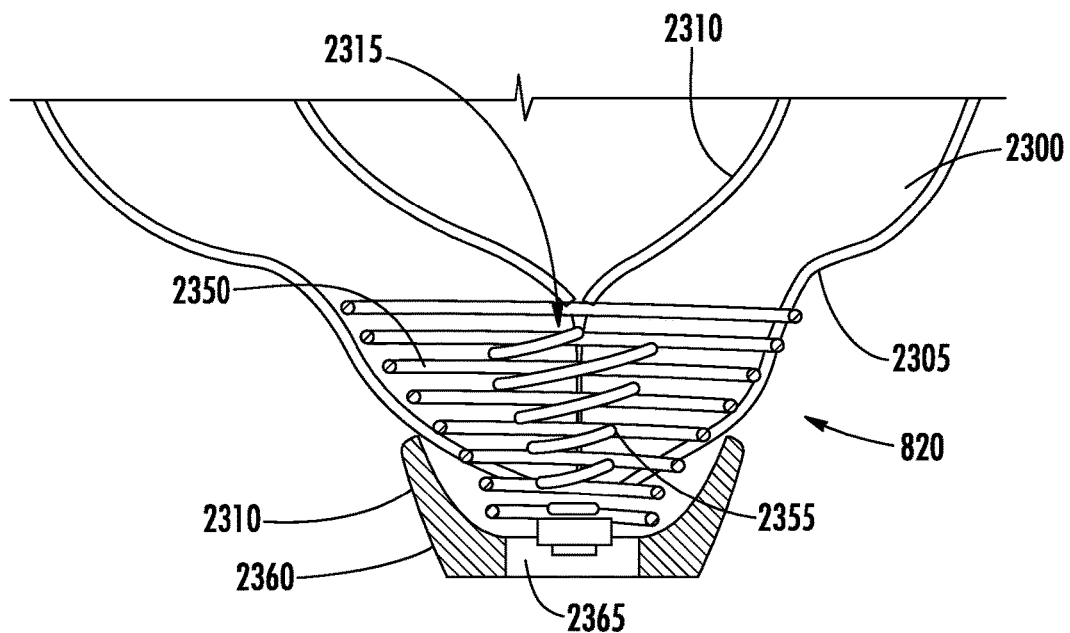
Figure 30B:
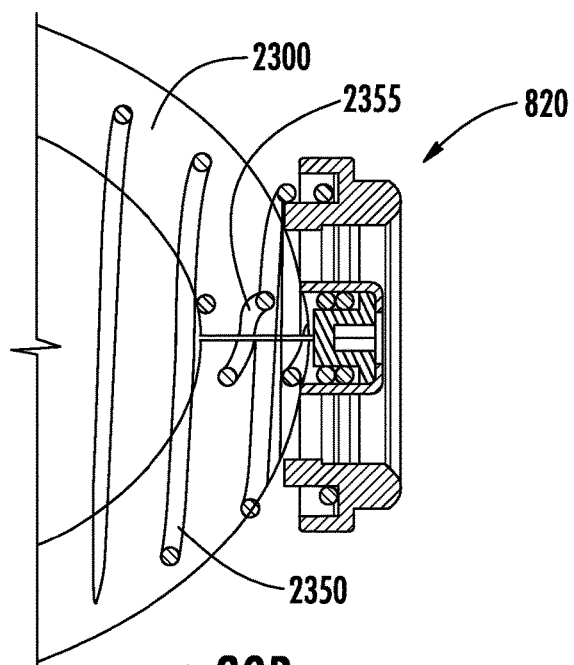

FIGS. 30A-30B show non-limiting cross-sectional views of exemplary attaching devices including an outer coil and an inner coil for use with conduit systems described herein, according to embodiments of the present invention.

Figure 31A:
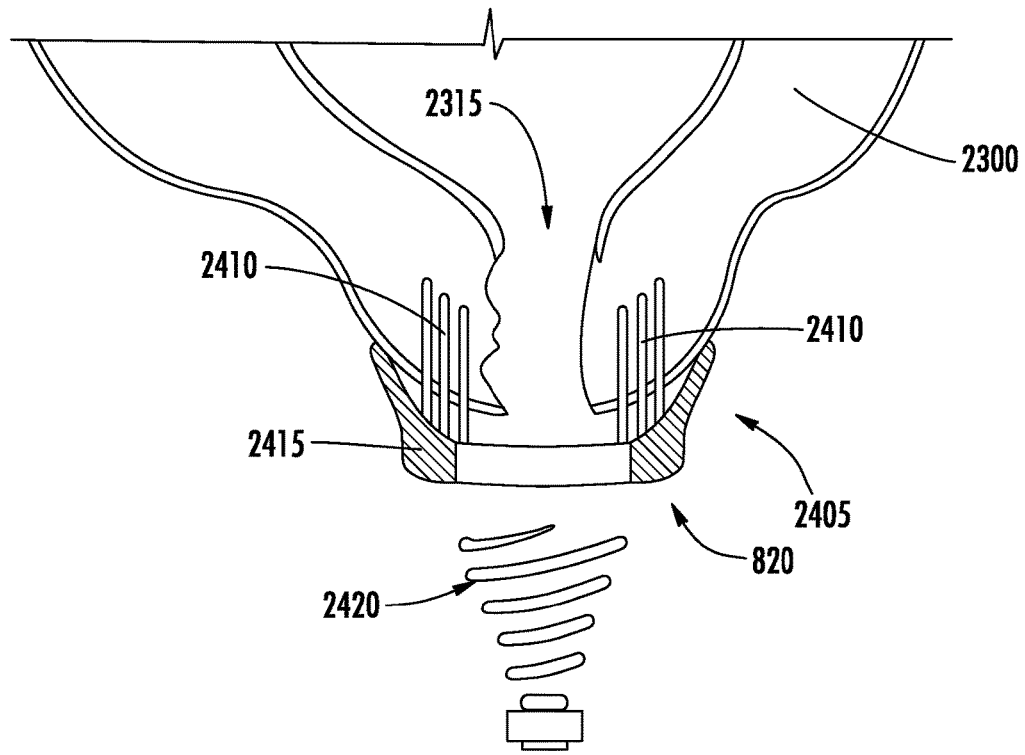
Figure 31B:
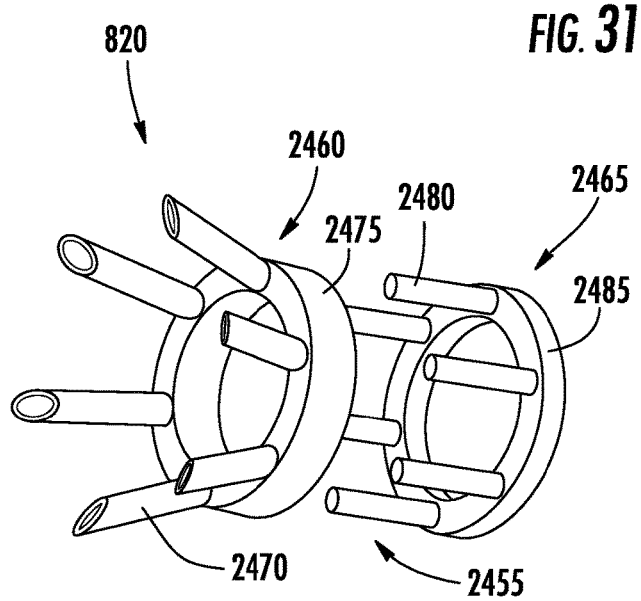
Figure 31C:
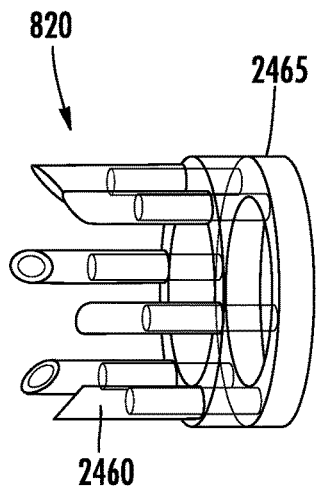

FIGS. 31A-31C show non-limiting cross-sectional and perspective views of exemplary attaching devices including a pinned supporting element for use with conduit systems described herein, according to embodiments of the present invention.

FIGS. 32A-32B show non-limiting top views of exemplary attaching devices including pins and one or more elastic bands for use with conduit systems described herein, according to embodiments of the present invention.

FIG. 33 shows a non-limiting cross-sectional view of an exemplary suturing method for use with conduit systems described herein, according to one embodiment of the present invention.

FIGS. 34A-34G show non-limiting perspective and side views of exemplary delivery systems for use with conduit systems described herein, according to embodiments of the present invention.

FIGS. 35A-35C show non-limiting perspective views of an exemplary attaching device including a skirt for use with conduit systems described herein, according to one embodiment of the present invention.

Figure 36A:
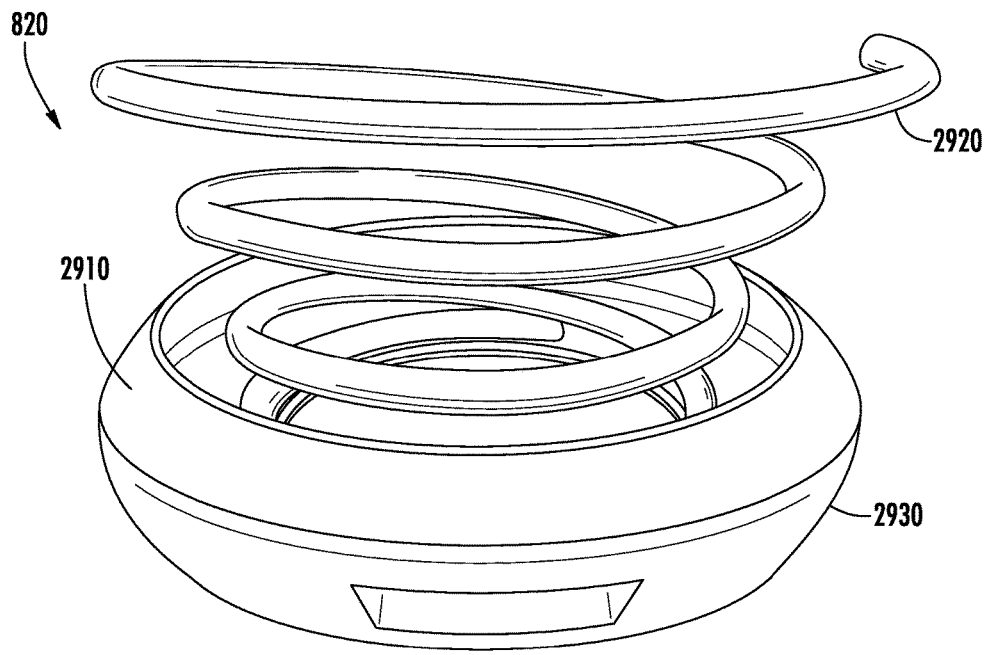
Figure 36B:
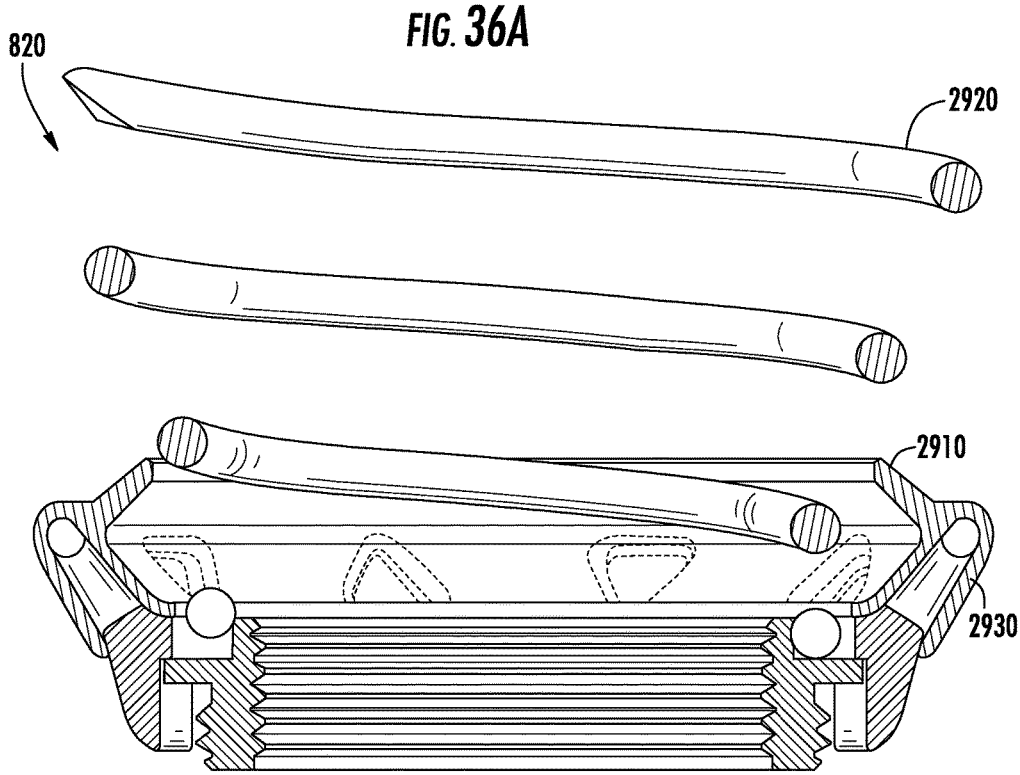

FIGS. 36A-36B show non-limiting perspective and cross-sectional views of an exemplary attaching device including an inward facing flange for use with conduit systems described herein, according to one embodiment of the present invention.

Figure 37A:
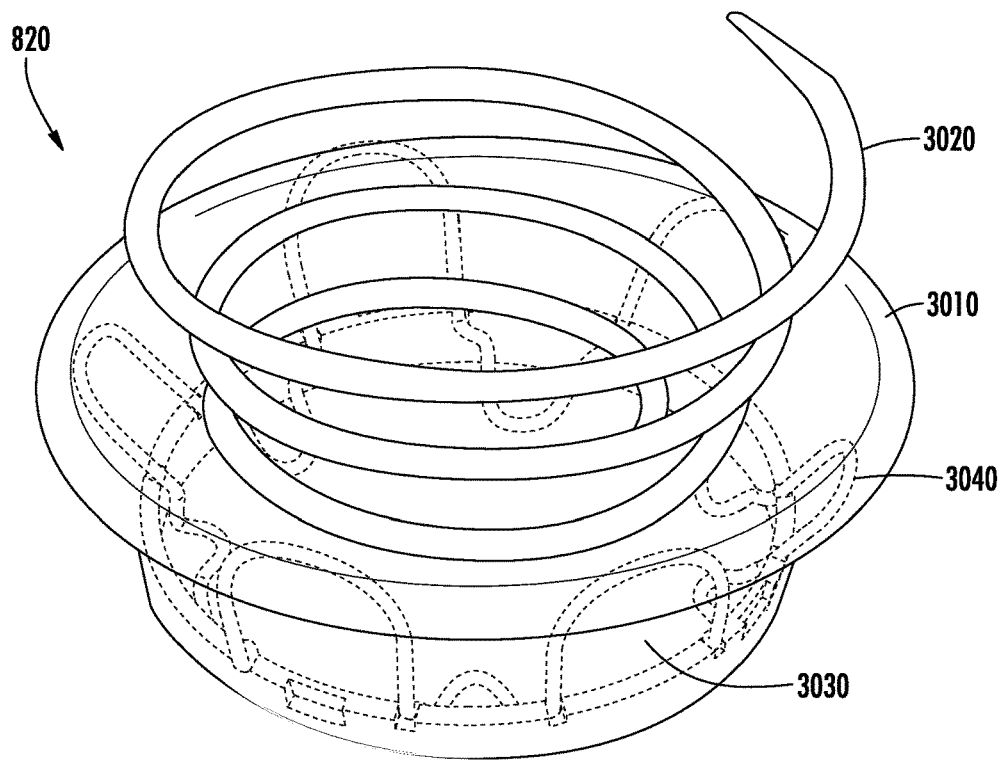
Figure 37B:
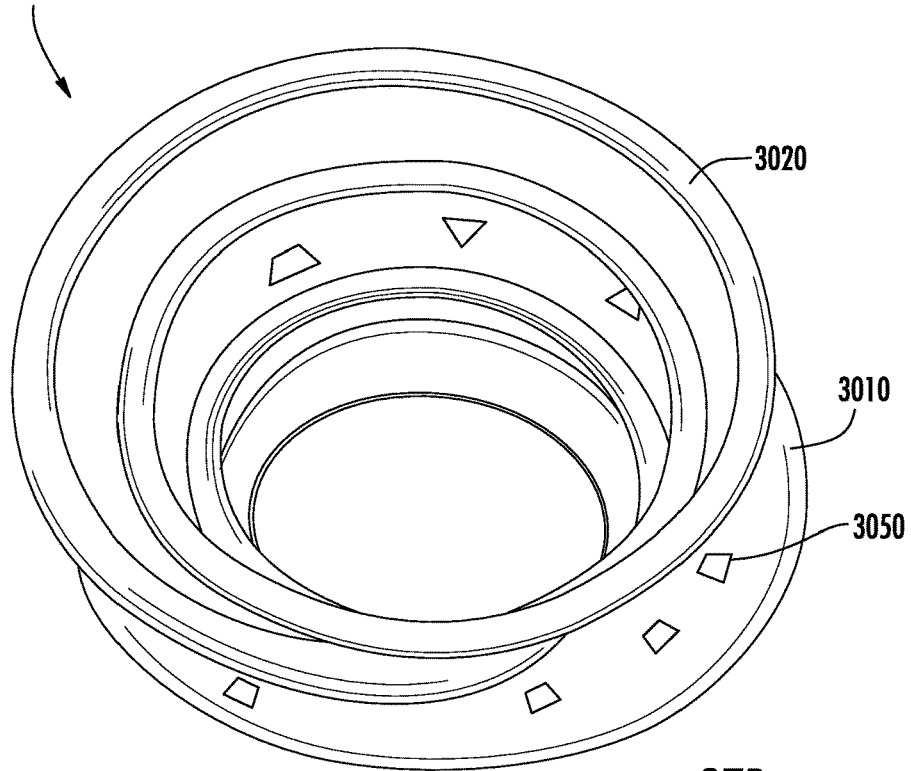

FIGS. 37A-37B show non-limiting perspective and cross-sectional views of an exemplary attaching device including an inward facing flange for use with conduit systems described herein, according to one embodiment of the present invention.

Figure 38:
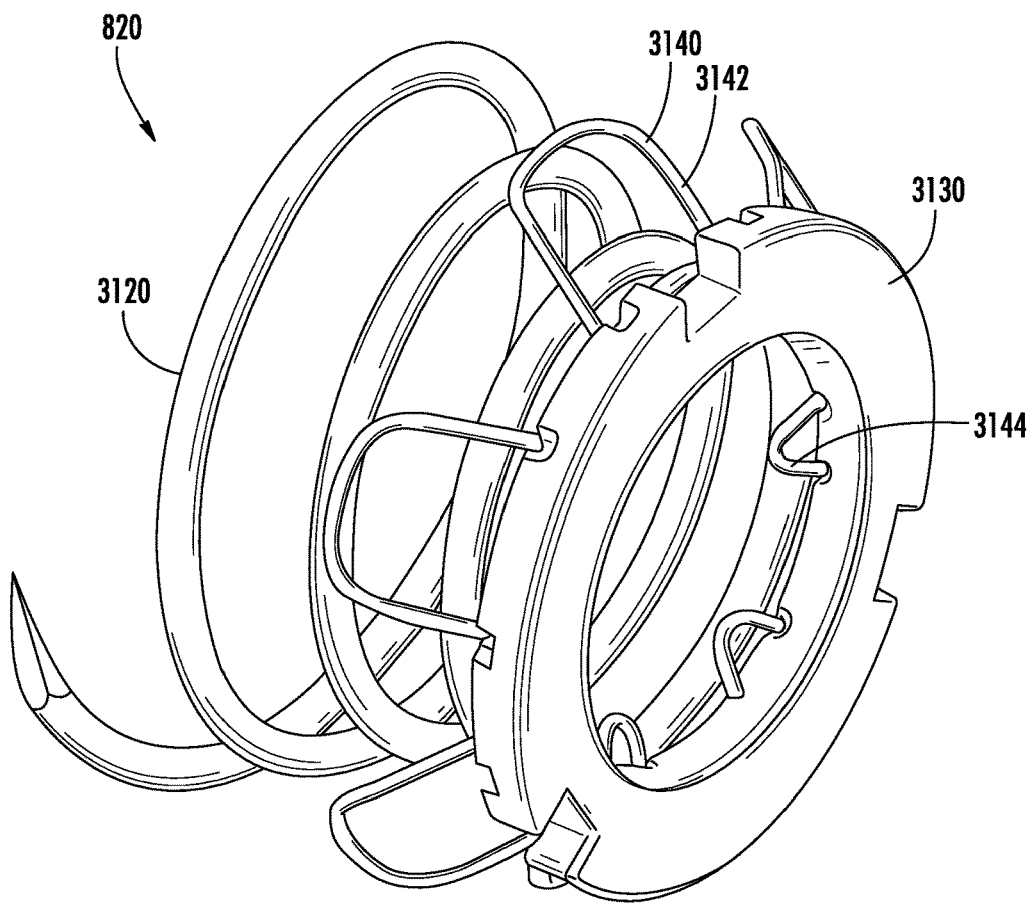

FIG. 38 shows a non-limiting perspective view of an exemplary attaching device including a wireframe for use with conduit systems described herein, according to one embodiment of the present invention.

Figure 39:
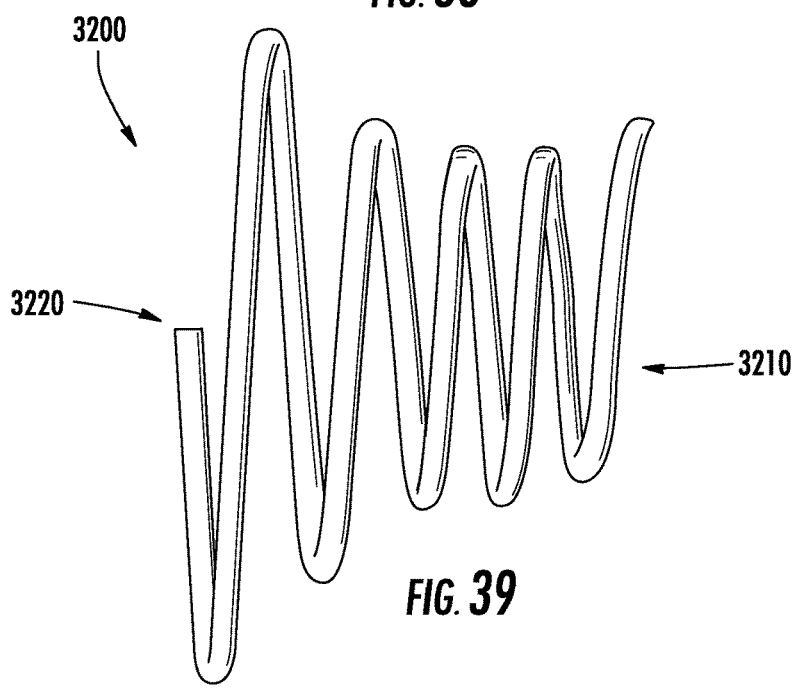

FIG. 39 shows a non-limiting side view of an exemplary coil of attaching device for use with conduit systems described herein, according to one embodiment of the present invention.

Figure 40:
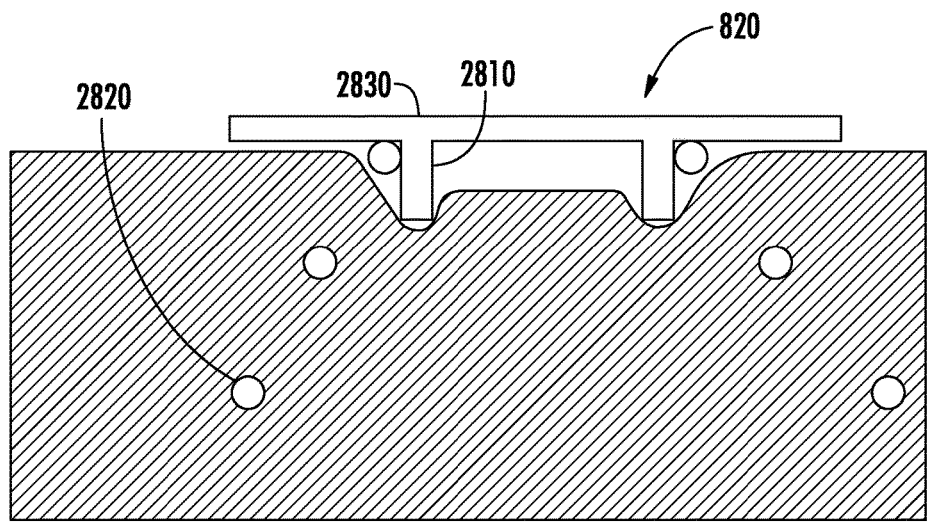

FIG. 40 shows a non-limiting section view of an exemplary attaching device including a skirt for use with conduit systems described herein, according to one embodiment of the present invention.

Figure 41A:
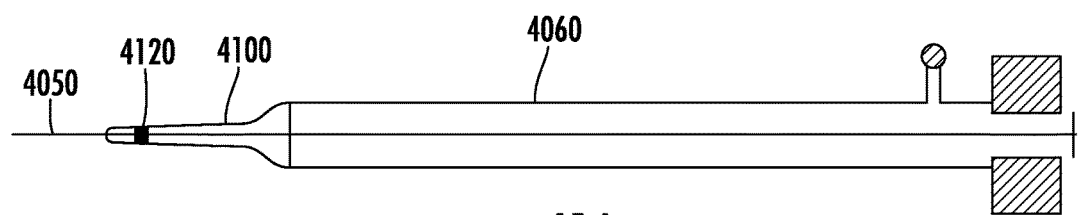
Figure 41B:
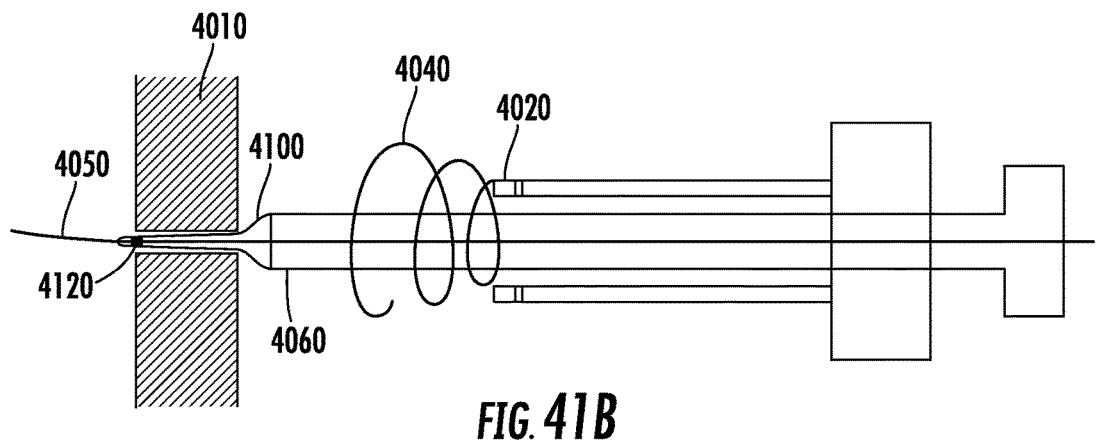
Figure 41C:
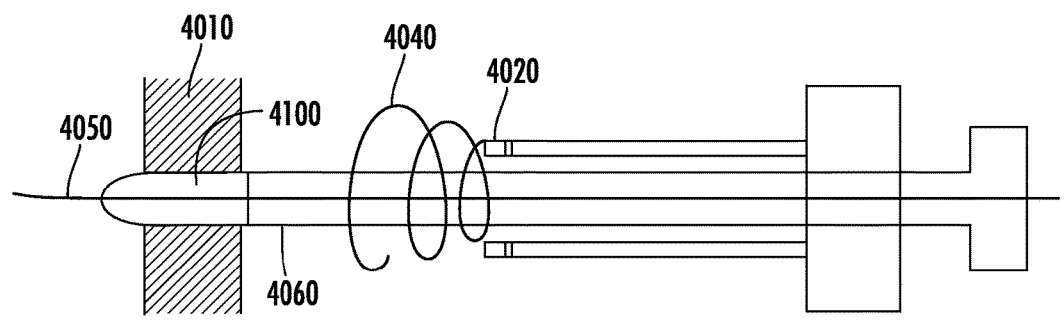

FIGS. 41A-41C show non-limiting cross-sectional views of an exemplary balloon dilator for use with conduit systems described herein, according to one embodiment of the present invention.

Figure 42:
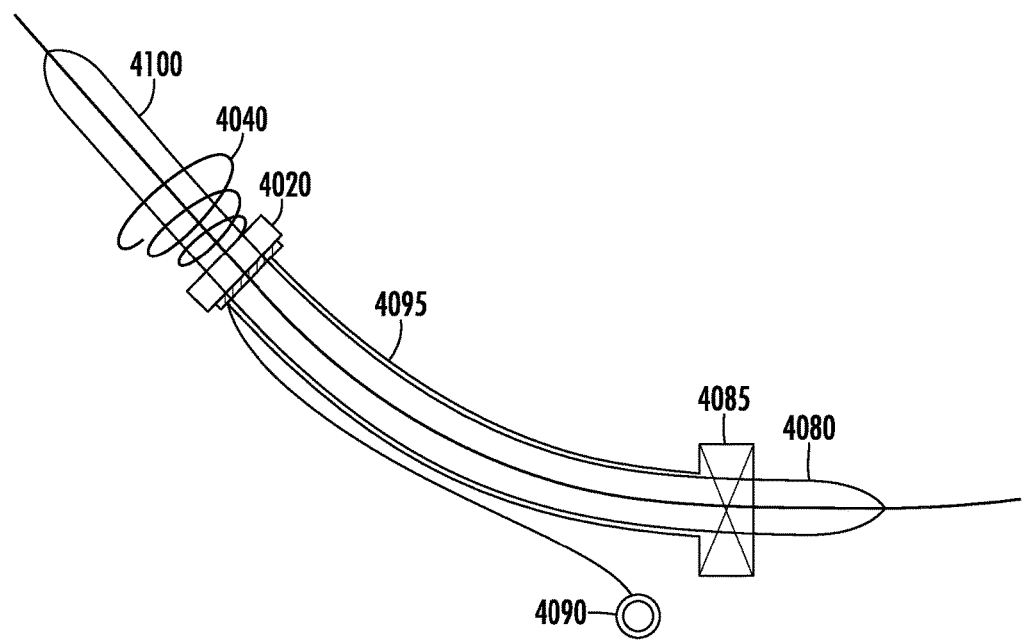

FIG. 42 shows a non-limiting side view of an exemplary balloon dilator for percutaneous use with conduit systems described herein, according to one embodiment of the present invention.

Figure 43A:
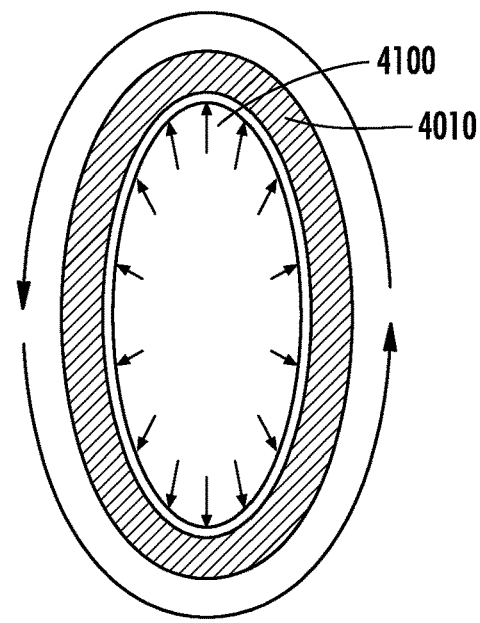
Figure 43B:
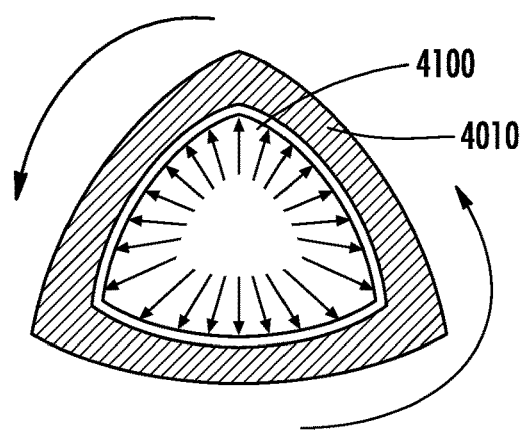

FIGS. 43A-43B show non-limiting cross-sectional views of exemplary attaching devices for use with conduit systems described herein, according to embodiments of the present invention.

Figure 44A:
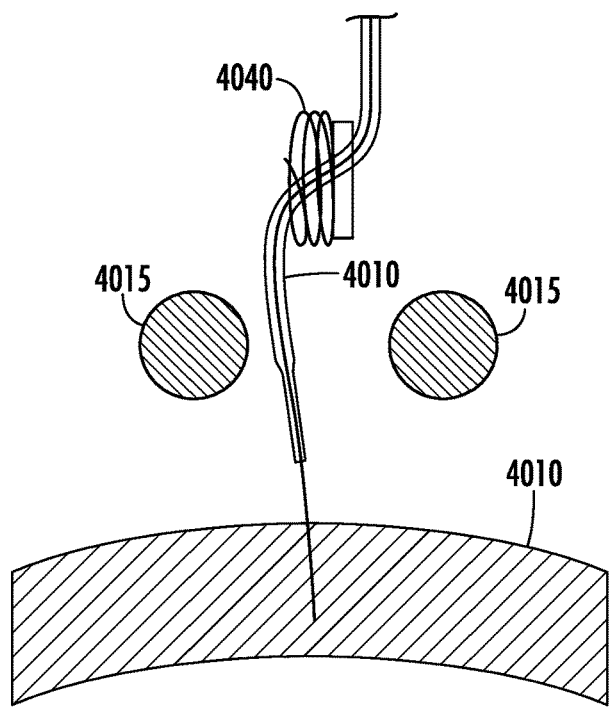
Figure 44B:
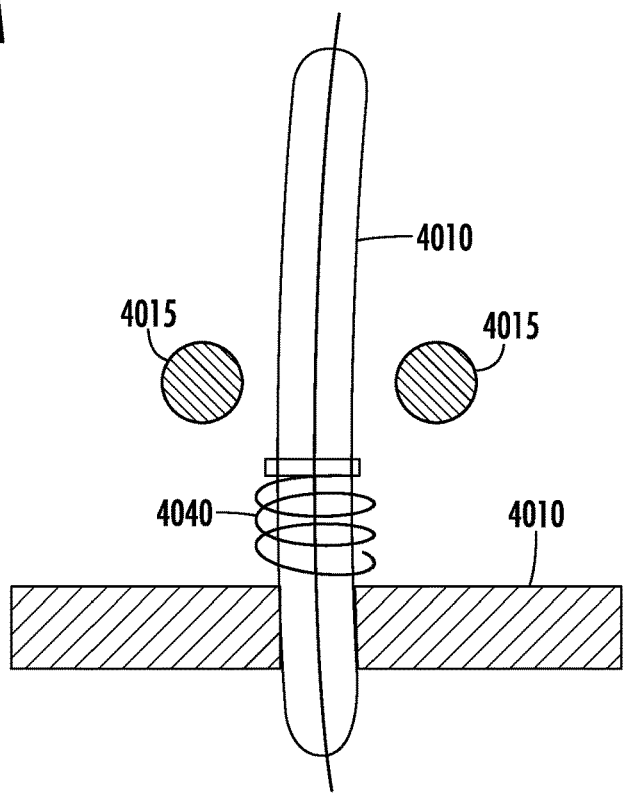

FIGS. 44A-44B show non-limiting cross-sectional views of an exemplary method of delivering an attaching device, according to one embodiment of the present invention.

Figure 45A:
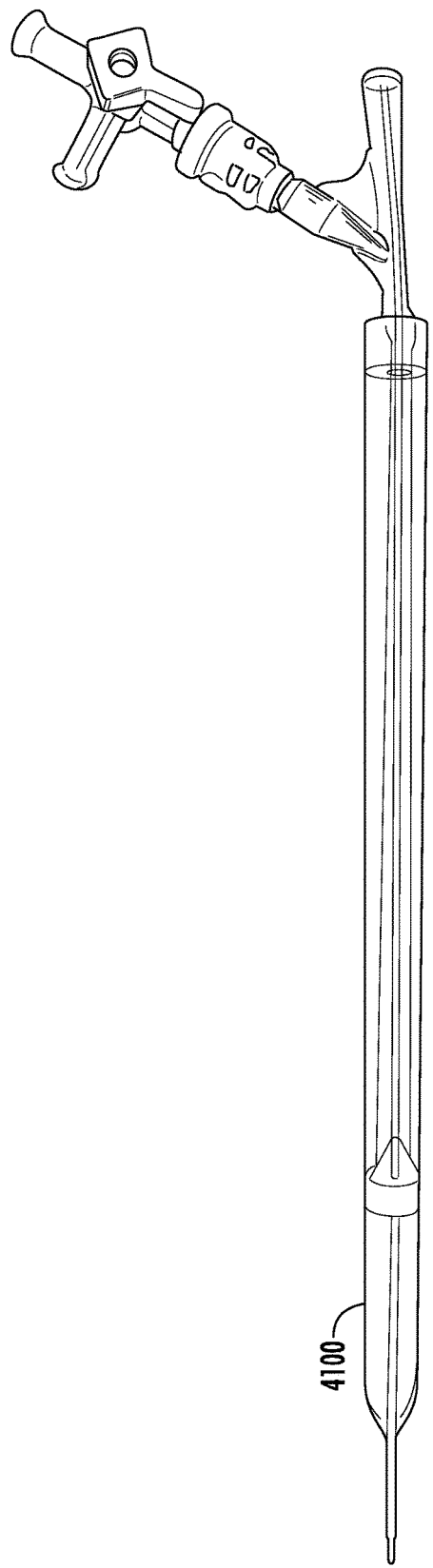
Figure 45B:
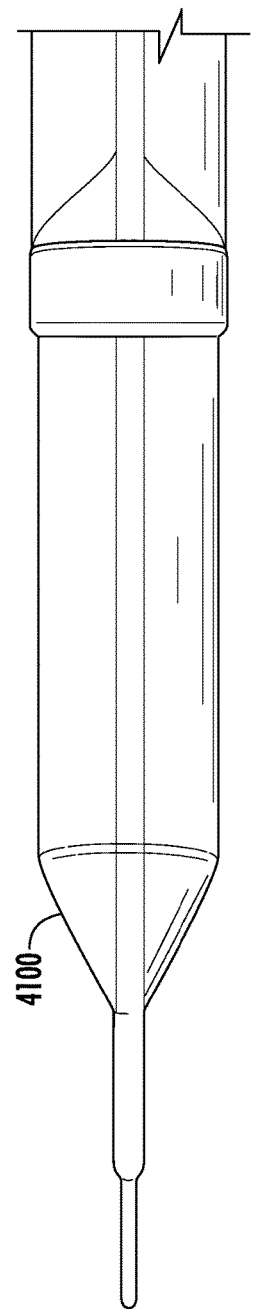

FIGS. 45A-45B show non-limiting side views of an exemplary balloon dilator for use with conduit systems described herein, according to one embodiment of the present invention.

Figure 46A:
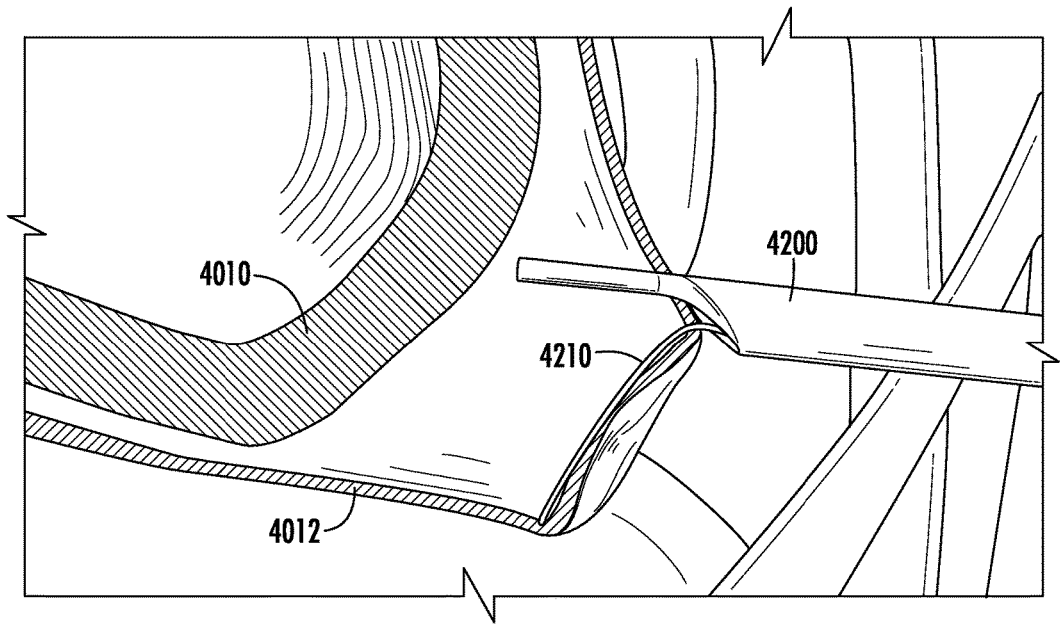
Figure 46B:
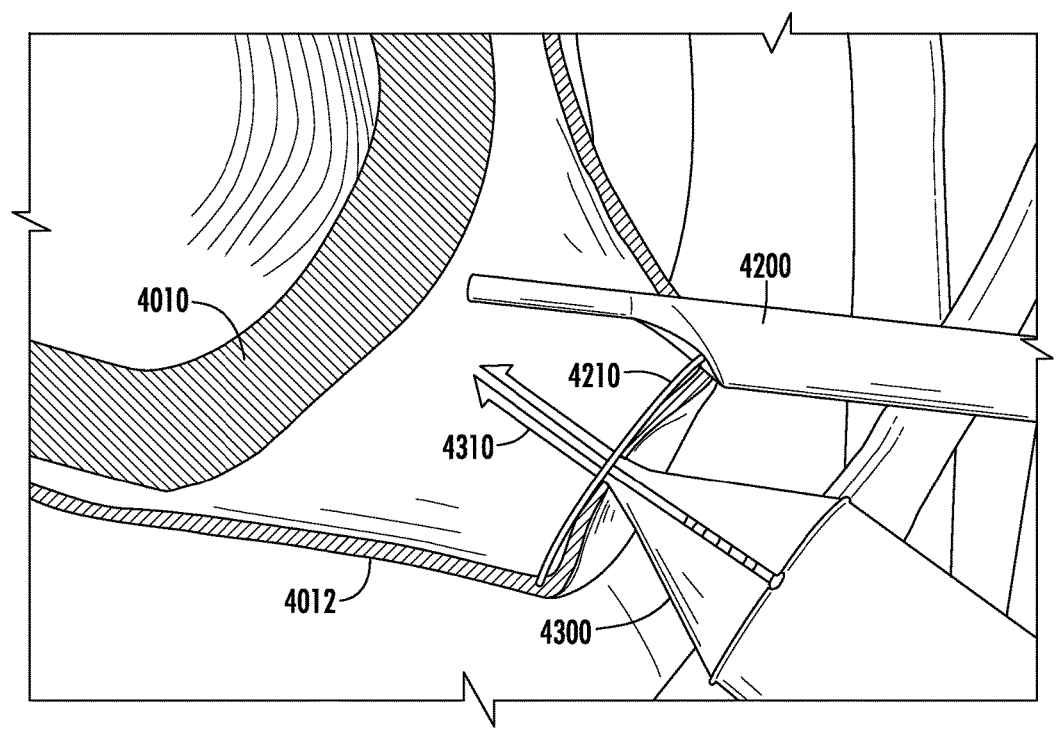
Figure 46C:
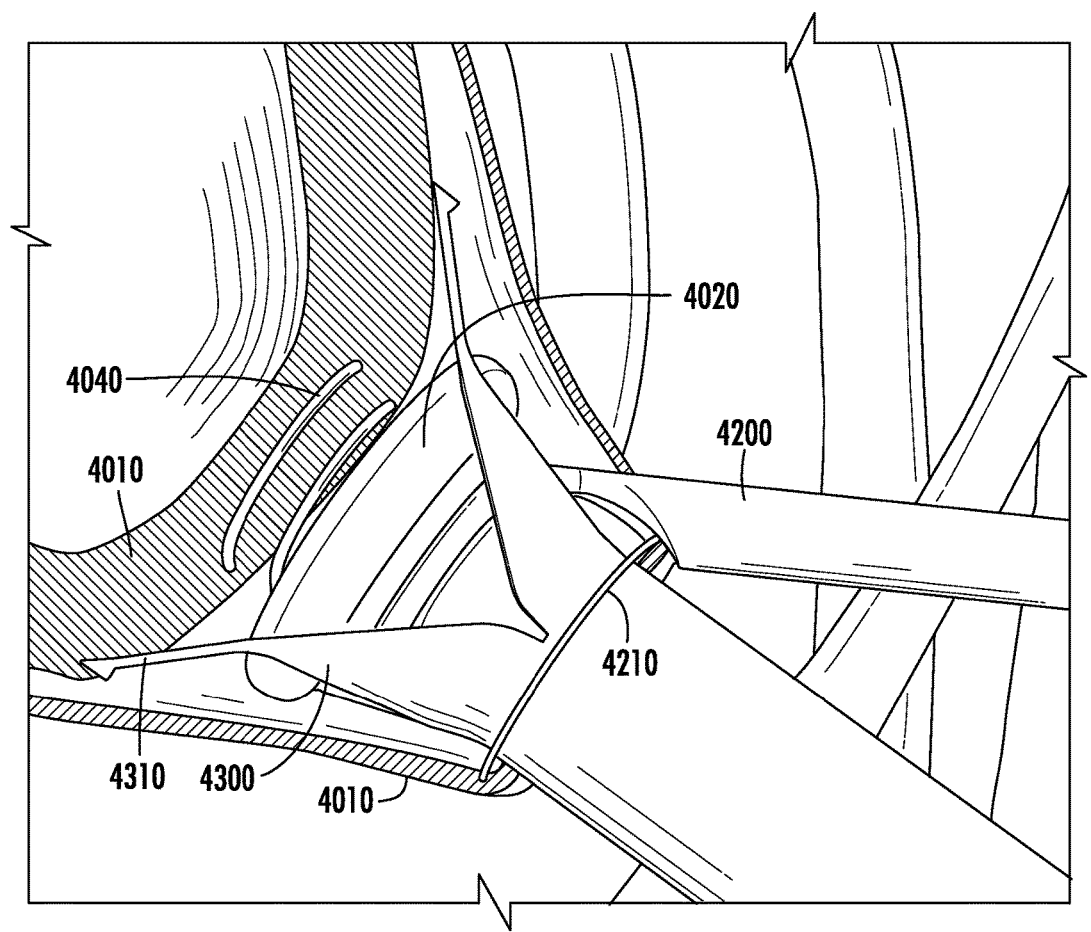

FIGS. 46A-46C show non-limiting schematic views of an exemplary procedure conducted with an embodiment of the present invention.

FIGS. 47A-47J show non-limiting schematic views of an exemplary procedure conducted with an embodiment of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. The singular forms "a," "an," and "the" include plural referents unless the context clearly dictates otherwise.

Certain embodiments of the invention provide devices, methods and systems for using a conduit device through a tissue wall of a patient, comprising: an outer conduit lumen; an inner conduit lumen adapted for insertion at least partially through the outer lumen; an attaching device in communication with a distal end of one of the outer lumen or the inner lumen, wherein the attaching device is adapted for securing to or inserting at least partially through a tissue wall, and a flow control mechanism configured to permit the passage of medical instruments therethrough. In certain embodiments, the outer lumen comprises one or more flow control mechanisms. In certain embodiments, the inner lumen comprises one or more flow control mechanisms.

The invention provides further embodiments, wherein the attaching device is adapted for releasably attaching to the outer lumen. In certain embodiments, a multiple access port device is provided in communication with at least one of the outer lumen or the inner lumen, wherein the multiple access port device includes a plurality of individual ports in fluid communication with the outer lumen or the inner lumen.

In certain embodiments, the invention provides a system for fluid sealed passage of a medical instrument through a conduit comprising: a medical instrument; a flow control diaphragm valve sized and shaped for receiving the medical instrument therethrough, comprising a first rigid conduit having proximal and distal ends, a flexible conduit attached in fluid communication at a distal end of the first rigid conduit, and a second rigid conduit attached in fluid communication at a distal end of the flexible conduit; wherein twisting rotation of the first rigid conduit relative to the second rigid conduit causes the flexible conduit to collapse inward and selectively move from an open configuration to a closed configuration forming a fluid-tight seal around the medical instrument when inserted therein or forming a fluid-tight closing when the medical instrument is not inserted therein. In certain embodiments, the valve further comprises a locking element to maintain the valve in the closed configuration. In certain embodiments, the system further comprises an insertion sheath connected to the flow control diaphragm valve.

In certain embodiments, the invention provides a system wherein the outer lumen comprises a selectively extendible section to lengthen or shorten the outer lumen. In certain embodiments, the outer lumen comprises telescopically extendible segments. In certain embodiments, the inner lumen is radially expandable in longitudinal cross-section. In certain embodiments, the inner lumen is collapsible and comprises an expanding member and a membrane over an outer surface of the expanding member. In certain embodiments, the inner lumen comprises a medical inserter sheath mounted on a dilator. In certain embodiments, the expandable member is expanded using at least one of: (a) mechanical force; (b) material modification; (c) structure modification; (d) electrical energy; or (e) thermal energy. In certain embodiments, the collapsible inner lumen comprises a flexible tip configured to allow selective sealing of the inner lumen.

The invention also provides a system for using a conduit device through a tissue wall of a patient, comprising: an outer lumen; an inner lumen adapted for insertion at least partially through the outer lumen; an attaching device in communication with a distal end of one of the outer lumen or the inner lumen, wherein the attaching device is adapted for securing to or inserting at least partially through a tissue wall, and in particular a cardiovascular apical cavity.

In certain embodiments, the invention provides a system for using a conduit device through a tissue wall of a patient, particularly a cardiovascular apical cavity, comprising: an outer lumen; an inner lumen adapted for insertion at least partially through the outer lumen; an attaching device in communication with a distal end of one of the outer lumen or the inner lumen, wherein the attaching device is adapted for securing to or inserting at least partially through a tissue wall, wherein the inner lumen further comprises a steerable tip comprising a guiding tip movably mounted on a distal end of the inner lumen, wherein the tip can be guided by the user in at least two dimensions.

In certain embodiments, the guiding tip comprises a ring guide mounted on a curved deflector element, and wherein said curved deflector element is movable over a range between a proximal straightened position and a distal increasingly deflected position, such that movement to the distal deflected position causes a guide wire extending through the inner lumen and through the ring guide to be directed toward the deflected position. In using such a device, the operator can achieve two or three-dimensional steering by distally and proximally manipulating the deflector element, in combination with rotating the inner lumen and/or axially moving the inner lumen distally or proximally.

The present invention further provides a system for using a conduit device through a tissue wall of a patient, comprising: an outer lumen; an inner lumen adapted for insertion at least partially through the outer lumen; an attaching device in communication with a distal end of one of the outer lumen or the inner lumen, wherein the attaching device is adapted for securing to or inserting at least partially through a tissue wall, wherein the attaching device further comprises a plug adapted for insertion through the attaching device to substantially seal the attaching device and prevent fluid flow through the attaching device, wherein the plug further comprises an extended surface extending distally from the plug, wherein the extended surface is adapted for insertion through a puncture in the tissue wall.

In certain embodiments, the plug has a flexibly sealable distal tip for selective access to the tissue from within the inner lumen. In certain embodiments, the attaching device further comprises means for exerting an inward radial force against the tissue, wherein, when the attaching device is implanted, the inward radial force urges the tissue inward toward the extended surface of the plug. In certain embodiments, the means for exerting an inward radial force comprises at least one of: (a) a radially expanding coil; (b) a conical flange: (c) one or more arm or barb members. In certain embodiments, the plug further comprises radial threads that engage corresponding radial threads on the attaching device to seal the tissue wall.

In certain embodiments of the invention, the attaching device further comprises a variable radius coiled member adapted to exist in a relaxed state having a narrow section with an inner diameter less than other sections of the variable radius coiled member, wherein when changing from an expanded state to a relaxed state, the narrow section diameter decreases, and wherein, when the attaching device is implanted, decreasing the narrow section diameter urges the tissue in an inward radial direction. In certain embodiments, changing from the expanded state to the relaxed state results from removing a plug from the attaching device, wherein prior to removal the plug exerts an outward radial force on the narrow section expanding the diameter of the narrow section.

In certain embodiments, the invention provides a system for providing access to a cardiovascular apical cavity comprising an attaching device adapted for securing to or inserting at least partially through a cardiovascular apical tissue wall, and at least one suture disposed on the device, wherein upon release of the attaching device from the tissue wall, the at least one suture is utilized to facilitate closing of the tissue wall. In certain embodiments, the attaching device uses a helical path when attaching to the securing tissue. In certain embodiments, the attaching device further comprises at least one pledget in communication with the at least one suture, wherein, during removal of the attaching device from the tissue wall, the at least one pledget and the at least one suture are utilized to facilitate closing of the tissue wall.

In certain embodiments, the invention provides a system for using a conduit device through a tissue wall of a cardiovascular apical cavity of a patient, comprising: an inner lumen adapted for at least partial insertion through the tissue wall of the patient and providing fluid communication therebetween, wherein the inner lumen is a collapsible inner lumen. In certain embodiments, the system comprises a flow control mechanism configured to permit the passage of medical instruments therethrough, and does not require the use of a haemostatic device. In certain embodiments, the collapsible inner lumen comprises an expanding member and a membrane over the outer surface of the expanding member. In certain embodiments, the collapsible inner lumen is adapted for insertion through a trans-cutaneous or endovascular access system when in a collapsed state. In certain embodiments, the collapsible inner lumen is adapted for receiving at least one medical instrument therethrough when in an expanded state.

In certain embodiments the invention provides a device for closing a conduit system, comprising: an attaching device adapted for securing to or inserting at least partially through a tissue wall, wherein the attaching device has a passage defined therethrough to allow fluid communication through the attaching device; and a plug adapted for insertion into the passage of the attaching device to substantially seal the attaching device and prevent fluid flow through the attaching device.

In certain embodiments, the invention provides systems and methods for delivering a medical instrument through a cardiovascular apical cavity tissue wall of a patient comprising: a) securing an attaching device to the cardiovascular apical cavity tissue wall, wherein the attaching device is adapted for securing a blood flow control mechanism configured to sealably permit the passage of medical instruments therethrough; b) puncturing the tissue wall; and c) dilating the punctured tissue for delivery of the medical instrument therethrough; wherein steps a) and b) may be performed in any order.

These and many other embodiments of the invention will be readily apparent to one of skill in the art in view of the present disclosure. Although some embodiments of the invention described herein are directed to a conduit device (see FIGS. 1 and 7, for example) and a system for implanting such a device to form an apicoaortic connector (AAC) between the cardiac apex and the aorta, for example, it will be appreciated by one skilled in the art that the invention is not so limited. For example, aspects of the conduit device and systems of the present invention can also be used to establish and/or maintain conduits in a variety of tissue structures using minimally-invasive and/or invasive delivery techniques. Furthermore, while certain embodiments of the invention described herein are directed to the thoracoscopic implantation of the conduit device to form at least one port for establishing an AAC, it should be understood that the system and/or vascular conduit device embodiments of the present invention may be used to establish valved and/or open conduits (including bypass conduits) to augment native blood vessels in order to treat a variety of vascular conditions including, but not limited to: aortic valvular disease, congestive heart failure, left ventricle outflow tract obstructions (LVOTO), peripheral arterial obstructions, small vessel obstructions, electrical abnormalities within the heart, congenital defects within the heart, failure or aneurisms in surrounding vessels, occlusion or thrombosis in coronaries or other arteries, and/or other conditions. Furthermore, the vascular conduit device and system of the present invention may also be used to establish a port for inter-ventricular repairs such as, for example, valve repair and/or replacement or ablation procedures. Thus, the conduit device described in further detail below may also comprise a threaded fluid-tight cap, and/or a cap having at least one pawl member (for engaging corresponding ridges defined on an outer surface of the conduit device) for selectively sealing a proximal end of the conduit device such that the inner tube thereof may serve as a re-usable port for repairing and/or treating diseased portions of the cardiac anatomy. Furthermore, the conduit device and system embodiments of the present invention may also be used to implant a conduit and/or port for left ventricular assist devices.

It should be further understood that various embodiments of the conduit device described herein may also be utilized to establish fluid communication between opposing surfaces of a variety of tissue walls and/or anatomical structures. For example, in some embodiments, the conduit device and system for implanting described herein may be used to establish a conduit (and consequently fluid communication) between opposing surfaces of a wall of an anatomical structure that may include, but is not limited to: a urinary bladder; a gall bladder; a diaphragm; a thoracic cavity; an abdominal cavity; an intestinal structure; a cecal cavity; and other tissue wall structures.

It should be understood that the various conduit device components described herein (see, for example, the components shown generally throughout FIGS. 1-5) may comprise a variety of biocompatible materials including, but not limited to: stainless steel; titanium substantially rigid biocompatible polymers; elastomeric biocompatible polymers; and combinations of such materials. For example, in some embodiments, the outer tube 10, ring 30, nut 20, and inner tube 40 may comprise substantially rigid biocompatible polymers. In some embodiments, the attaching device 15 may comprise a biocompatible metal and/or metal alloy that may be embedded substantially within and/or operably engaged with an injection-molded polymer used to form the outer tube 10. Furthermore, as described further herein, some embodiments of the present invention may further comprise a sealing member 35 operably engaged with a distal end of the ring 30. In such embodiments, the sealing member 35 may comprise a substantially compliant biocompatible polymer (such as an elastomeric polymer) that may be suitable for establishing a substantially fluid tight seal between the ring 30 a surface of the tissue wall 850. Similarly, the various components of the coring device 2 described herein may also comprise a combination of biocompatible materials suitable for removing and retaining the tissue core 850a in order to define an aperture in the tissue wall 850 such that the inner tube 40 may be installed to establish fluid communication between the opposing first and second surfaces 855, 853 of the tissue wall 850 (as shown in FIG. 5A, for example).

As shown generally in FIGS. 1-3, one embodiment of a system for implanting a conduit device 1 in a tissue wall 850 having a first surface 855 and an opposing second surface 853 may comprise an outer tube 10 defining a guide aperture extending axially therethrough and an attaching device 15 extending from a distal end of the outer tube 10. The attaching device 15 may be configured for advancing along a helical path at least partially through the tissue wall 850 such that at least a portion of the attaching device 15 becomes disposed substantially between the first surface 855 and the opposing second surface 853 of the tissue wall 850 when the outer tube 10 is rotated relative to the first surface 855 of the tissue wall 850. As shown generally in FIG. 2, the attaching device 15 may be integrally formed within the outer tube 10. For example, the attaching device 15 may, in some embodiments, be placed at least partially in a mold such that the polymeric or other components of the outer tube 10 may be molded substantially around at least a portion of the attaching device 15 (which may comprise a static coil and/or elastic spring, as described further herein). In other embodiments, the attaching device 15 may be operably engaged with at least a portion of the outer tube 10 via adhesive, RF welding, and/or other attachment methods that may be suitable for securely operably engaging the attaching device 15 to the outer tube 10.

The attaching device 15 may comprise, in some embodiments, a helical static coil having a sharpened distal end adapted for piercing the tissue wall 850 as the outer tube 10 is rotated relative to the first surface 855 of the tissue wall 850. In other embodiments, the attaching device 15 may comprise a helical elastic spring having a sharpened end adapted for piercing the tissue wall 850 as the outer tube 10 is rotated relative to the first surface 855 of the tissue wall 850. In some embodiments, as shown in FIG. 4, wherein the attaching device 15 comprises a helical spring and/or coil, the spring and/or coil may device a radially-expanding helix as the attaching device 15 extends away from the distal end of the outer tube 10. In some embodiments, wherein the attaching device comprises a conical and/or "radially-expanding" helix, the attaching device 15 may act to compress at least a portion of the tissue wall 850 radially inward and towards an outer surface of the inner tube 40 so as to establish a substantially fluid-tight seal between the outer surface of the inner tube 40 and the portion of the tissue wall 850 that has been urged radially inward. Furthermore, in some such embodiments, the radially-expanding helix of the attaching device 15 may correspond, for example, to a ring 30 comprising a frusto-conical assembly configured for receiving at least a portion of a substantially curved tissue wall 850 (see, for example, FIG. 5B) so as to form a substantially fluid-tight seal between the frusto-conical assembly of the ring 30 and the tissue wall 850.

In other embodiments, as shown generally in FIG. 7, the attaching device 15 may comprise a helical spring and/or coil having a substantially constant helical diameter as the attaching device 15 extends away from the distal end of the outer tube 10. The substantially consistent helical diameter of the attaching device 15 shown generally in FIG. 7 may be useful for operably engaging the outer tube 10 with a substantially flat tissue wall. Furthermore, as shown generally in FIG. 7, in some embodiments, the corresponding ring 30 (and the corresponding sealing member 35 that may be operably engaged therewith) may also be configured to provide a substantially flat and/or disc-shaped sealing surface that may be suitable for seating on and/or establishing a substantially fluid-tight seal with a substantially flat first tissue surface that may surround an aperture defined in a correspondingly flat tissue wall.

As described herein, the system may further comprise a ring 30 operably engaged about an outer surface of the outer tube 10. As shown generally in FIGS. 3 and 5B, the ring 30 may be configured for cooperating with the attaching device 15 such that at least a portion of the tissue wall 850 is secured between the attaching device 15 and the ring 30 so as to operably engage the outer tube 10 with the tissue wall 850. Some embodiments may further comprise a plurality of ridges 11 and/or threads disposed on the outer surface of the outer tube 10. According to such embodiments, the ring 30 may comprise at least one deformable pawl member configured for releasably engaging the plurality of ridges 11 disposed on the outer surface of the outer tube 10. Other embodiments (as shown generally in FIG. 2, for example), may also further comprise threading 11 on at least a portion of the outside surface of the outer tube 10 and corresponding threading on at least a portion of an inside surface of the ring 30. The threading 11 (and corresponding threading on the inner surface of the ring 30) may be being configured to cooperate for axially securing the ring 30 relative to the outer tube 10.

As shown generally in FIGS. 5A-5B, some embodiments may further comprise a nut 20 operably engaged about an outer surface of the outer tube 10 and proximal to the ring 30. According to such embodiments, the nut 20 may comprise threading on at least a portion on an inside surface of the nut 20. The threading disposed on the inside surface of the nut 20 may be configured for cooperating with the threading 11 on at least a portion of the outside surface of the outer tube 11 for axially securing the nut 20 relative to the outer tube 10 and the adjacent ring 20. As shown in FIGS. 5A-5B, the nut 20 may be configured for cooperating with the ring 30 to advance the ring 30 towards the distal end of the outer tube 10. As shown generally in FIGS. 5A-5B, the attaching device 15 may provide counter-traction so as to allow for the rotation (and resulting advancement) of the nut 20 (and the ring 30 disposed distally thereto) such that rotation of the nut 20 (and the corresponding movement of the ring 30 toward the first tissue surface 855) may draw at least a portion of the tissue wall 850 into engagement with an inner surface of the ring 30 such that the conduit device 1 (and particularly the outer tube 10 thereof) is stabilized, engaged in a substantially fluid tight seal, and/or operably engaged with respect to the tissue wall 850 prior to the use of a coring device 2 for removing a tissue core 850a via the guide aperture defined axially through the outer tube 10, as shown in FIGS. 5C and 5D.

In order to ensure that the ring 30 forms a substantially fluid-tight seal with the first surface 855 of the tissue wall 850 about the aperture defined therein, some embodiments (as shown in FIG. 1, for example) may further comprise a sealing member 35 operably engaged with a distal end of the ring 30. The sealing member 35 may comprise, for example, a gasket or other elastomeric component configured for establishing a substantially fluid tight seal between the ring 30 and the first surface 855 of the tissue wall 855. As described herein, some embodiments of the present invention may be configured for establishing fluid communication between the opposing sides of the walls of a mammalian heart (such as the ventricular apex, for example). In such embodiments, the conduit device 1 may be required to be operably engaged with a substantially curved tissue wall 850 (see FIG. 5A, for example). In such embodiments, the ring 30 may comprise a frusto-conical assembly configured for receiving at least a portion of the substantially curved tissue wall 850 so as to form a substantially fluid-tight seal between the frusto-conical assembly of the ring 30 and the tissue wall 850.

As shown, for example, in FIG. 5B, in some embodiments, the ring 30 may be urged towards a distal end of the outer tube 10 by the rotation of a nut 20 about threading 11 disposed on an outer surface of the outer tube 10. Thus, according to some such embodiments, the cooperation of the attaching device 15 (which may comprise a piercing helical spring and/or coil, for example) with the ring 30 may act to draw at least a portion of the curved tissue wall 850 into the frusto-conical assembly of the ring 30 such that a substantially fluid-tight seal may be formed and maintained between the frusto-conical assembly of the ring 30 and the tissue wall 850.

In some conduit device 1 embodiments, as shown generally in FIG. 2, the ring 30 may comprise a seal testing aperture 36 that may allow a clinician to selectively test whether or not a substantially fluid-tight seal has been established between the ring 30 and the first surface 855 of the tissue wall 850 when the ring 30 is moved towards the distal end of the outer tube 10 and into engagement with the tissue wall 850. For example, a clinician may operably engage a fluid source (such as a saline solution bag) with the seal testing aperture 36 (which may comprises a luer lock connector or other connector for operably engaging the fluid source) and introducing a fluid via seal testing aperture 36 and observing the interface between the ring 30 and the first surface 855 of the tissue wall 850 to see if any substantial amount of fluid emerges. If no fluid is readily visible, a clinician may be reasonably assured that the seal formed between the ring 30 and the tissue wall 850 is substantially fluid-tight. By assessing the seal formed between the ring 30 and the tissue wall 850, a clinician may determine if it is medically safe to introduce the coring device 2 via the guide conduit defined in the outer tube 10 (i.e. determine if blood loss is likely to occur between the ring 30 and the first surface 855 of the tissue wall 850 when the coring device 2 (and the coring cylinder 65 thereof) is advanced through the tissue wall 850 as shown in FIG. 5C).

In some embodiments, the seal testing aperture 36 may also serve an alternative function for rotationally securing the ring 30 relative to and the first surface 855 of the tissue wall 850. For example, a clinician may insert a needle and/or other elongate spike through the seal testing aperture 36 defined in the ring 30 and substantially into the tissue wall 850. The interaction of the needle and/or spike with the ring 30 (via the seal testing aperture 36) and the tissue wall 850 may thus reduce a chance that the ring 30 (and the helical attaching device 15 extending from the outer tube 10) are rotatable relative to the tissue wall 850 such that the ring 30 and the helical attaching device 15 may be less prone to "backing out" of the tissue wall 850 once the seal is established between the ring 30 and the first surface 855 of the tissue wall 850.

In some additional embodiments, as shown generally in FIG. 7, the ring 30 (and/or the sealing member 35 that may be operably engaged therewith) may define a substantially flat and/or disc-shaped annular sealing surface that may be configured for establishing a substantially fluid-tight seal between the ring 30 and a substantially flat first tissue surface 855 about an aperture defined in the tissue wall 850.

Referring to FIG. 5C, for example, some embodiments may further comprise an inner tube 40 defining a conduit aperture extending axially therethrough. The inner tube 40 may be configured for insertion into the guide aperture defined by the outer tube 10. In some embodiments, as shown in FIG. 6, the inner tube 40 may be carried by a coring device 2 that may be advanced through the guide aperture defined by the outer tube 10 and configured for substantially simultaneously removing a tissue core 850a to define an aperture in the tissue wall 850 and operably engaging the inner tube 40 with the outer tube 10 so as to establish and/or maintain a reliable and engageable pathway for fluid communication between the first and second surfaces 855, 853 of the tissue wall 850. In order to facilitate the secure engagement of the outer tube 10 with the inner tube 40, some conduit device 1 embodiments may comprise a first securing device 13 operably engaged with a proximal end of the outer tube 10 and a complementary second securing device 43 operably engaged with a proximal end of the inner tube 40. According to such embodiments, as shown generally in FIG. 2, the second securing device 43 may be configured for selectively operably engaging the first securing device 13 so as to operably engage the inner tube 40 with the outer tube 10. As shown generally in FIG. 6, the second securing device 43 may comprise one or more deformable pawls configured for selectively operably engaging the first securing device 13 as shown in FIG. 2 (wherein the first securing device 13 comprises one or more ridges disposed on a proximal portion of the outer surface of the outer tube 10).

It is appreciated that the conduit device embodiments described herein are only example conduit device configurations and that many other device configurations may be utilized with various system components described. For example, a conduit device may not necessarily require an attaching device, an inner tube, an outer tube, and/or a coring member, as described, but may simply include a tube body and an attaching device, or may be delivered utilizing other delivery instruments and/or other techniques. Thus, additional aspects of the system and device components may be utilized with any number of conduit device configurations, as generally described below.

Delivery Techniques

As shown generally in FIG. 6, some system embodiments for installing a conduit device 1 may further comprise a coring device 2 configured for advancing through the conduit aperture defined by the inner tube 40 and through the tissue wall 850 to define an aperture therein by removing a tissue core 850a (see FIG. 5D, for example, showing the coring device 2 removing a tissue core 850a and collecting the tissue core 850a in a coring bore defined by a coring cylinder 65. As shown generally in FIGS. 5C and 6, the coring device 2 may be further configured for carrying the inner tube 40 through the aperture such that the inner tube 40 extends at least partially through the aperture (see FIG. 5F, for example) so as to establish fluid communication between the first 855 and second 853 surfaces of the tissue wall 850. In some embodiments, as shown in the cross-sectional side view of FIG. 5D, the coring device 2 (and/or the coring cylinder 65 thereof) defines a coring bore extending axially therethrough configured for receiving the tissue core 850a removed by the coring cylinder 65.

As shown in FIGS. 5C-5E, the coring device 2 may also comprise a piercing rod 60 slidably advancable and retractable within the coring bore defined by the coring device 2. The piercing rod 60 may further comprise a retrieval device 61 operably engaged with a distal end thereof and configured for axially retaining the tissue core 850a removed by the coring cylinder 65. In various embodiments, the retrieval device 61 may include, but is not limited to: a barb; a hook; corkscrew; expandable balloon; a self-expanding structure; and/or other device configured for initially piercing the tissue wall 850 so as to be capable of retrieving the tissue core 850a removed by the coring device 2 as described further herein. As shown generally in FIG. 5C, the piercing rod 60 may be configured for advancing so as to pierce the tissue wall 850 prior to removal of the tissue core 850a (i.e. prior to the advancement of the coring cylinder 65 through the tissue wall 850). Furthermore, as shown generally in FIG. 5E, the piercing rod 60 may be further configured for retracting after removal of the tissue core 850a such that the tissue core 850a is retrievable via a proximal end of the coring device 2. In some system embodiments for installing a conduit device 1, the coring device 2 may further comprise a handle 63 operably engaged with a proximal end of the coring device 2 (and/or a proximal end of the coring cylinder 65). According to such embodiments, as shown generally in FIG. 6, the handle 63 may define a tissue core chamber 62 in communication with the coring bore defined by the coring cylinder 65. As shown in FIG. 5E, the tissue core chamber 62 may thus be configured for receiving the tissue core 850a retrieved by retraction of the piercing rod 60 (and the retrieval device 61 operably engaged with a distal end thereof). In order to allow a clinician to positively identify and/or confirm the removal and retraction of the tissue core 850a, in some system embodiments at least a portion of the handle 65 may be provided with a substantially transparent material (such as a transparent polycarbonate polymer, for example) such that the tissue core 850a received by the tissue core chamber 62 may be visible (to a clinician or an endoscopic imaging device, for example) from a position substantially outside the handle 63.

FIGS. 5A-5G illustrate the various steps involved in the utilization of one embodiment of the system of the present invention for installing a conduit device 1 in a tissue wall 850 (such as the ventricular apex). It should be understood that various embodiments of the present invention may be utilized for installing the conduit device 1 for use in medical procedures that may include, but are not limited to: bypass; cardiac valve repair or replacement; attachment of a ventricular assist device; and combinations of such procedures. As shown in FIG. 5A, an exemplary process for installing a conduit device 1 may begin with the implantation of the attaching device 15 in the tissue wall 850. As described herein, the attaching device 15 may comprise a helical spring and/or coil configured for advancing along a helical path at least partially through the tissue wall 850 such that at least a portion of the attaching device 850 becomes disposed substantially between the first surface 855 and the opposing second surface 853 of the tissue wall 850 when the outer tube 10 is rotated relative to the first surface 855 of the tissue wall 850. In some embodiments, the attaching device 15 may be sized such that the axial length of the attaching device 15 does not extend substantially distal to the second surface 853 of the tissue wall 850.

In some embodiments, wherein the attaching device comprises a conical and/or "radially-expanding" helix, the attaching device 15 may act to compress at least a portion of the tissue wall 850 radially inward and towards an outer surface of the inner tube 40 so as to establish a substantially fluid-tight seal between the outer surface of the inner tube 40 and the portion of the tissue wall 850 that has been urged radially inward by the conical and/or radially-expanding helix of the attaching device 15. Furthermore, in embodiments wherein the attaching device 15 comprises a conical and/or "radially-expanding" helix, the attaching device 15 may act to compress at least a portion of the tissue wall 850 radially inward such that the portion of the tissue wall 850 may be more readily received by ring 30 (which may comprise a frusto-conical structure configured for receiving the compressed portion of the tissue wall 850). As shown in FIG. 5B, the conduit device 1 installation process may continue with the advancement and/or tightening of the ring 30 towards a distal end of the outer tube 10. As described herein, some conduit device 1 embodiments of the present invention may comprise a nut 20 operably engaged about an outer surface of the outer tube 10 proximal to the ring 30. In some such embodiments, the nut 20 may comprise threading on at least a portion on an inside surface thereof, wherein the threading is configured for cooperating with the threading 11 on at least a portion of the outside surface of the outer tube 10. The nut 20 may thus be configured to cooperate with the ring 30 to advance the ring 30 towards the distal end of the outer tube 10, and therefore into contact with the first surface 855 of the tissue wall 850. As shown generally in FIG. 5B, once the nut 20 and ring 30 are advanced distally (which may be accomplished by hand-tightening the nut 20), the ring 30 may cooperate with the attaching device 15 such that at least a portion of the tissue wall 850 is secured between the attaching device 15 and the ring 30 so as to securely operably engage the outer tube 10 with the tissue wall 850.

As shown in FIG. 5C, once the outer tube 10 is stabilized relative to the tissue wall 850, a coring device 2 (which, in some embodiments, as shown in FIG. 6, may be configured for carrying an inner tube 40), may be inserted into the guide aperture defined axially within the outer tube 10. As described herein with respect to FIG. 6, the coring device 2 may comprise a coring cylinder 65 configured for advancing through the conduit aperture defined by the inner tube 40 and through the tissue wall 850 to define an aperture therein by removing a tissue core 850a (see FIG. 5D, for example). Referring again to FIG. 5C, some embodiments may further comprise a piercing rod 60 slidably advancable and retractable within the coring bore defined by the coring cylinder 65. The piercing rod 60 may comprise, in some embodiments, an elongate proximal end that may be manipulated (i.e. extended and/or retracted) by a clinician in order to initially pierce the tissue wall 850 and/or retract the tissue core 850a removed therefrom (as described further herein). As shown in FIGS. 5D and 5E, the piercing rod 60 may further comprise a retrieval device 61 operably engaged with a distal end thereof and configured for axially retaining the tissue core 850a removed by the coring cylinder 65. The piercing rod 60 may be configured for advancing so as to pierce the tissue wall 850 prior to removal of the tissue core 850a (i.e. prior to advancement of the coring cylinder 65). Furthermore, as shown in FIG. 5E, the piercing rod 60 may be further configured for retracting after removal of the tissue core 850a such that the tissue core 850a is retrievable via a proximal end of the coring device 2.

As shown in FIGS. 5D and 6, the coring device 2 may be further configured for carrying the inner tube 40 through the aperture such that the inner tube 40 extends at least partially through the aperture so as to establish fluid communication between the first and second surfaces 855, 853 of the tissue wall 850 (see also, FIG. 3, for example). As described herein, with respect to various conduit device 1 embodiments of the present invention the outer tube 10 may comprise a first securing device 13 operably engaged with a proximal end thereof and the inner tube 40 (carried, for example, by the coring device 2 into position relative to the outer tube 10) may comprise a complementary second securing device 43 operably engaged with a proximal end thereof. As shown generally in FIG. 3, the second securing device 43 (which may comprise a deformable pawl, for example) may be configured for selectively operably engaging the first securing device 13 (which may comprise a complementary at least one ridge disposed on an outer surface of the outer tube 10) so as to positively and securely operably engage the inner tube 40 with the outer tube 10.

Referring again to FIG. 5E, the coring device 2 may, in some embodiments, comprise a handle 63 operably engaged with a proximal end of the coring device 2. As described herein, the handle 63 may define a tissue core chamber 62 in communication with the coring bore defined, for example, by the coring cylinder 65. The tissue core chamber 62 may thus be configured for receiving the tissue core 850a retrieved by retraction of the piercing rod 60 (and the retrieval device 61 operably engaged with a distal end thereof). In some embodiments, the coring device 2 may also define a fill aperture configured for operably engaging a source of saline solution or other fluid that may be used to substantially flood the coring bore defined by the coring cylinder 65 and the tissue core chamber 62 so as to reduce the chance of introducing gas bubbles (i.e. air bubbles) into an interior chamber defined by the tissue wall 850 when the coring device 2 is introduced via the outer tube 10.

As described generally herein with regard to the various system embodiments of the present invention, the conduit device 1 installation process may advantageously allow a clinician to visually confirm that the tissue core 850a removed by the coring cylinder 65 has been completely and cleanly removed from the aperture defined in the tissue wall 850. For example, in some embodiments, at least a portion of the handle 63 may comprise a transparent material such that the tissue core 850a received within the tissue core chamber 62 may be directly visible by a clinician and/or an endoscopic imaging device from a position substantially outside the handle 63. As shown in FIGS. 5F and 5G, after the coring device 2 (and the tissue core 850a retained in the handle 63 thereof) is retracted and removed from the inner tube 40, a clamp C may be applied to a proximal end of a graft portion that may be operably engaged with the inner tube 40 of the conduit device 1. In other embodiments, the inner tube 40 may comprise one or more ridges defined on an outer surface of the proximal end thereof that may be configured for receiving a deformable cap or other cover for temporarily and/or semi-permanently closing the aperture defined by the installed conduit device 1. As described herein, the conduit device 1 may be utilized as a portion of a two-part bypass system that may comprise another corresponding conduit device 1 installed in a tissue wall 850 defining a wall of the mammalian aorta, for example. The two corresponding conduit devices 1 may then be operably engaged with one another via a valve device so as to form an apicoaortic connection (AAC) in order to bypass, for example, a faulty valve or other mechanical defect present in a subject's cardiac anatomy.

FIGS. 8-11 illustrate various perspective and cross-sectional views of an example conduit delivery instrument, which includes an inner lumen 805 and an outer lumen 810 which is adapted to carry the inner lumen 805 therethrough. FIG. 8 illustrates a cross-sectional view of an inner lumen 805, FIG. 9 illustrates a cross sectional view of an outer lumen 810, while FIGS. 10 and 11 illustrate cross-sectional and perspective views of the inner lumen 805 inserted into the outer lumen 810, according to one embodiment.

With reference to FIG. 8, the inner lumen 805 may generally be an elongated tube member having a passage defined therethrough that allows instruments or other therapy to be delivered through the inner lumen 805 and into the cavity or other side of a tissue wall. The inner lumen 805 may serve to provide access at least partially through a tissue wall, such as may be achieved by the inner tube 40 of the conduit device described with reference to FIGS. 1-5G. At or near the proximal end of the inner lumen 805, at least one flow control mechanism 807 may be provided to limit fluid flow when the inner lumen 805 is inserted into the outer lumen 810 and in fluid contact with bodily fluid during use. As shown in FIG. 8, one embodiment of a flow control mechanism 807 may be a clamp valve having a pliable material forming at least a portion of the conduit and adaptable to receive a clamping instrument (e.g., surgical clamp, hemostat, etc.), such as is shown with reference to FIG. 5F. In another embodiment, the clamp valve of the flow control mechanism 807 may be in operable communication with an integrated clamp that can be selectively actuated by an operator, and which does not require the use of an additional instrument to close the clamp valve.

Other flow control mechanisms may be utilized, such as, but not limited to, duck bill valves, globe valves, single or multiple leaflet valves, breast pump valves, diaphragm valves, and the like. For example, the delivery system with an inner lumen 100 is shown in FIG. 13 as including a one-way valve 130, such as a duck-bill valve, positioned intermediately along the length of the delivery system 100. This one-way valve 130 may allow passage of a lumen and/or instrument through the valve 130, but prevent fluid from flowing proximally from the valve 130. It is appreciated that one or more other valve mechanisms can be included, such as, but not limited to, globe valves, single or multiple leaflet valves, breast pump valves, diaphragm valves, and the like. These valves may be used by themselves or in combination. It is further appreciated that the placement of the one-way valve 130, or other valves included, may be at one or more different locations along the length of the delivery system 100.

According to one embodiment, an additional diaphragm valve may be included at or near the proximal end of the delivery system 100. FIGS. 14A-14C illustrate an example diaphragm valve 135, according to one embodiment. A diaphragm valve 135 may, alone or in combination with other valves, improve blood loss control and provide easy access with a lumen and/or instrument (or any other device) through the delivery system. An example diaphragm valve 135 may be a rotation collapsible diaphragm valve, diagrammatically represented in FIGS. 14A-14B, which consists of at least two aligned conduits 205, 210 connected by a flexible conduit 215. According to one embodiment, the two aligned conduits 205, 210 may further include alignment arms or collars 220 to maintain alignment and relative position and distance of the conduits 205, 210 with respect to each other. A flexible conduit 215 may be formed from any suitable pliable material having elastic or viscoelastic properties and allowing deformation thereof.

In use, rotation of a first conduit 205 with respect the second conduit 210 causes the flexible conduit 215 to twist and collapse within itself, therefore reducing inner diameter of the passage therethrough. In one embodiment, complete closure of the passage may be achieved by increased turning of the conduits 205, 210 relative to each other. In another embodiment, if an instrument, lumen, or other medical instrument is inserted through the conduit, then the flexible conduit 215 may close onto the instrument, lumen, or other device and create a fluid seal therearound.

With reference to FIG. 15 and FIG. 16, an embodiment with an inner tube represented by a medical sheath 3100, which may be flexible, semi-flexible or rigid may be used to establish fluid communication between the tissue walls. The proximal end of the sheath may have one or multiple valves including but not limited to a duckbilled valve 3400 and/or a collapsible diaphragm valve 3500 of FIG. 15. In order to facilitate the insertion of a medical sheath 3200, it may be delivered mounted on a dilator 3210 with an axial orifice for a guidewire 3200 as shown in FIG. 16.

With reference to FIG. 9, an outer lumen 810 is also shown as a generally elongated tube member having a passage 812 defined therethrough. The passage 812 is shaped and sized having an inner radius large enough to accept at least a portion of the outer lumen 810. According to one embodiment, the distal end of the outer lumen 810 can be adapted to receive an attaching device 820, such as a coiled attaching device 15 having an outer flange 30, as shown in FIG. 12 and described above with reference to FIGS. 1-5G, or any other attaching means. In the embodiment shown by FIG. 9, the distal end of the outer lumen 810 includes threads 814 to threadably receive an attaching device 820. The threads 814 are shown here formed in an inner surface; though they may be formed on another portion of the lumen 810, as desired and depending upon the design and configuration of the attaching device 820. According to other embodiments, instead of threads, the distal end may include other attachment means for securing an attaching device 820 to the outer lumen 810, such as, but not limited to, mechanical means, such as tabs, pins, screws, clamps, threads, hooks, interference fit, friction fit, etc., magnetic means, chemically bonded, and the like. According to various embodiments, the attaching device 820 may be releasably or permanently secured. At the proximate end of the multi-valve port threads 815 or other releasable locking mechanism may be used to attach a cap or a multiple access port device to the outer lumen 81

According to one embodiment shown in FIG. 13A, a dual action mechanism 125 may be provided at or near the distal end of the conduit delivery system 100 to release the attaching device after the procedure is completed. In this embodiment, two simple but distinct motions allow releasing the delivery system 100 from the attaching device 120 after being capped. This dual action system may be conformed from one or multiple of the means described above or one or multiple of this means and using an actuator such as a button, lever or lock. Therefore, initial action on the actuator will then allow for secondary action which will release the attaching device from the delivery system. Such a dual action system will increase the security when using the device in medical procedures.

As shown in FIG. 9, the outer lumen 810 also may optionally include at least one flow control mechanism 816. According to the embodiment, the flow control mechanism 816 is provided at or near the proximal end of the outer lumen 810 for controlling fluid flow therethrough, such as prior to insertion of the inner lumen 805 and/or after removal of the inner lumen 805. According to the embodiment shown, the flow control mechanism 816 is a clamp valve, such as described with reference to the inner lumen 805. However, it is appreciated that, according to other embodiments, other flow control mechanisms may be utilized, such as, but not limited to, duck bill valves, globe valves, single or multiple leaflet valves, breast pump valves, diaphragm valves, and the like. Moreover, in some embodiments, the outer lumen 810 may be referred to as a multi-valved port, indicating that an outer lumen 810 may have multiple valves for controlling fluid flow therethrough, which may be the same or different types of valves.

FIGS. 10-11 show the inner lumen 805 inserted within the outer lumen 810, and an attaching device 820. It is appreciated, however, that according to other embodiments the outer lumen 810 can be utilized with a different attaching device, such as one including hooks, barbs, wires, pins, arms, sutures, suction forces, a flange, any combination thereof, and the like. Multiple of these attaching devices may be used in conjunctions in the system in order to improve anchoring to the tissue. In some preferred embodiments multiple coils may be used in conjunction, these coils may be or may not be centered on the same rotational axis. In other embodiments both suction and a coil may be used to attach the system to the tissue surface. As shown by FIG. 10, when the inner lumen 805 is inserted through the outer lumen 810, at least a portion of the distal end of the inner lumen 805 may extend distally from the outer lumen 810, providing access at least partially through a tissue wall to which the attaching device will be secured. The interaction between the different components of the system, such as the fit of the inner lumen 805 within the outer lumen 810 and the various flow control mechanisms 807, 816, provide beneficial sealing of the system to prevent blood or other fluid loss during use. Although not shown, one or more de-airing orifices, as are known, may be included with the inner lumen 805 and/or the outer lumen 810 to prevent introducing air into the patient's vasculature during use.

According to one embodiment shown in FIG. 13A, a motion absorption element 115 may be utilized to allow for movement of the distal end (e.g., the attaching device 120) of the delivery system 100 in all directions, or universally, such as radially and laterally. Thus, the motion absorption element 115 compensates for the movement of the tissue, such as a beating heart or other organ, while holding the outer lumen statically in place, reducing the risk of tearing the tissue. According to one embodiment, as shown in FIG. 13A, the motion absorption element 115 may be configured as an expandable tube, such as tube having an accordion-type shape, allowing for movement at the motion absorption element 115. In other embodiments, the motion absorption element 115 may be constructed from a pliable material having elastic or viscoelastic properties that compensate for the motion of the tissue.

In yet another embodiment, such as shown in FIG. 13C, a jointed element, such as a universal-type joint or a socket-type joint 116, can be utilized to be a motion absorption element to compensate for motion or rotation of the distal end of the delivery system 100 when anchored onto the tissue. The universal joint 116 may also be accompanied but a flexible section 117 is some cases where the joint is considered to be rigid axially. The motion absorption element, however, should allow for the transfer of torque and/or other rotational or translational force applied to the proximal end of the delivery system 100, such as when inserting an attaching device 120 through the tissue, or removing an attaching device 120.

According to the embodiment such as shown in FIGS. 13A and 13B, the delivery system may include an outer lumen with an extendable body section that allows for increasing or decreasing the overall length of the outer lumen. An extendable body section 110 thus allows adjusting the overall length of the delivery system 100 and controlling the distance from the tissue surface to the proximal end of the delivery system 100. Adjusting the length advantageously allows treating patients having different weights, body sizes, and anatomies. According to various embodiments, the extendable body section 110 may be, but is not limited to, an extendible tube 112 as shown in FIG. 13B, a series of telescopic conduits as shown in FIG. 13A, threaded conduits, and the like. For example, according to one embodiment, the extendable body section 110 may include multiple telescoping tubular members in cooperative communication and adapted for selective extension and retraction. The telescoping tubular members may be in sliding communication, wherein a translational force applied to at least one of the tubular members cause extension or retraction of the extendable body section 110.

According to another embodiment, the extendable body section may include multiple tubular members in threaded communication. For example, an outer tubular member may have threads formed on an inner surface and an inner tubular member may have complementary threads formed on an outer surface. Turning one of the outer or inner tubular member in a first direction with respect to the other tubular member will thus cause the extendable body section to expand in length and turning one of the outer or inner tubular member in a second direction opposite the first direction with respect to the other tubular member will thus cause the extendable body section to retract in length. In a further example, the extendable body can be constructed from an accordian-like corrugated or extendible tube that may change its axial length by changing the angular relations between the different segments of the tube.

It is appreciated that, according to various embodiments, the extendable body section 110 may only comprise a portion of the outer lumen 105, whereas another portion of the outer lumen 105 may have a fixed length or is not otherwise adjustable. Moreover, it is appreciated that other aspects of the delivery system 100 may likewise include adjustable members to adjust relative lengths, such as an inner lumen, conduit, or instrument insertable through the outer lumen 105.

FIGS. 17A-17F show various detailed views of an example use providing access through a tissue wall, according to one embodiment. At FIG. 17A, an attaching device 820 secured to an outer lumen 810 is delivered to the surface of the tissue wall (not shown) through a small incision. The attaching device 820 can use an anchoring mechanism, such as, but not limited to, a coil to releasably attach to the tissue wall According to one embodiment, a flange of the attaching device 820 may also facilitate urging tissue radially inwards to improve attachment of the attaching device 820 and sealing of the tissue around the inner lumen 805 to be delivered. In some embodiment this flange may have internal fluid communications or channels which could allow for suction therethrough and aid in the attachment of the device to the tissue surface.

Figure 17A:
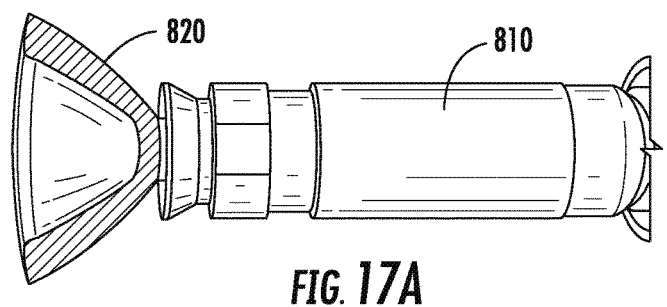
Figure 17B:
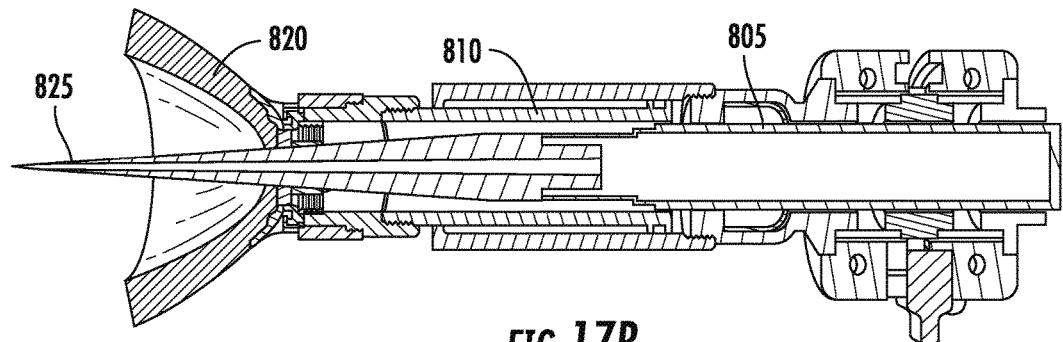

At FIG. 17B, a piercing or cutting instrument 825 can optionally be utilized to perforate the tissue wall through the approximate center of the attaching device 820, in a manner similar to that described with reference to FIG. 5C. According to one embodiment, the piercing element 825 is attached to the distal end of the inner lumen 805 (e.g., releasably attached) and thus can be delivered through the passage of the outer lumen 810. According to one embodiment, the piercing element 825 may have a sharp tine or other member utilized to perforate the tissue. The piercing element 825 may optionally include an inner passage or bore to allow passing the piercing element 825 over a guide wire. In one embodiment, a sharpened boring element can be used to perforate the tissue wall and create a tissue plug, which defines the approximate size of the puncture or access site through the tissue wall. Additionally, to retrain any loose tissue, an attaching element can be utilized to grasp the tissue which is being cut and/or released by the cutting tool. This attaching element may be a coil, a clamp, jaws, a series of hooks, barbs, pins, expanding/collapsing surfaces, and the like.

Figure 17C:
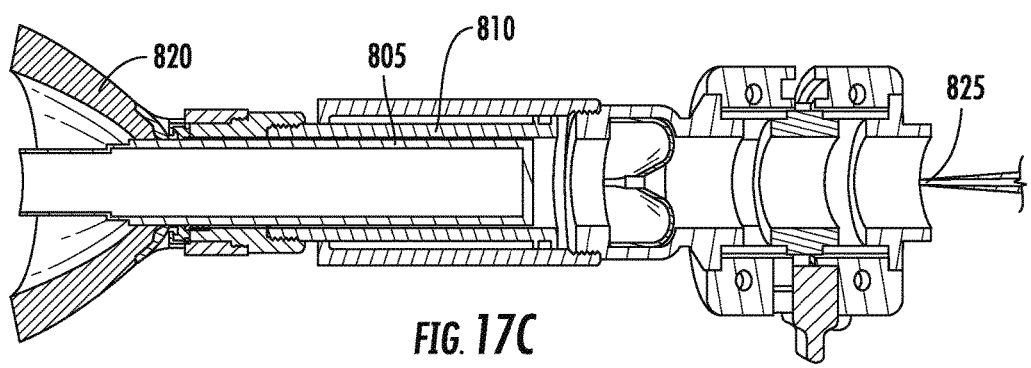
Figure 17D:
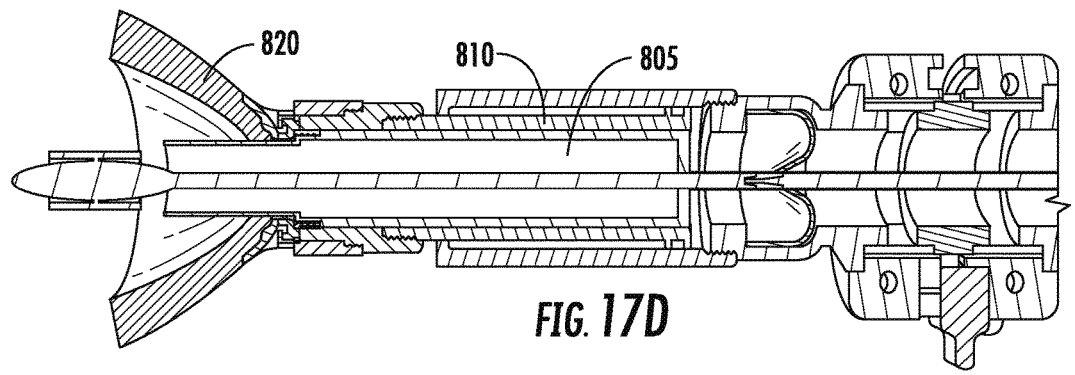
Figure 17E:
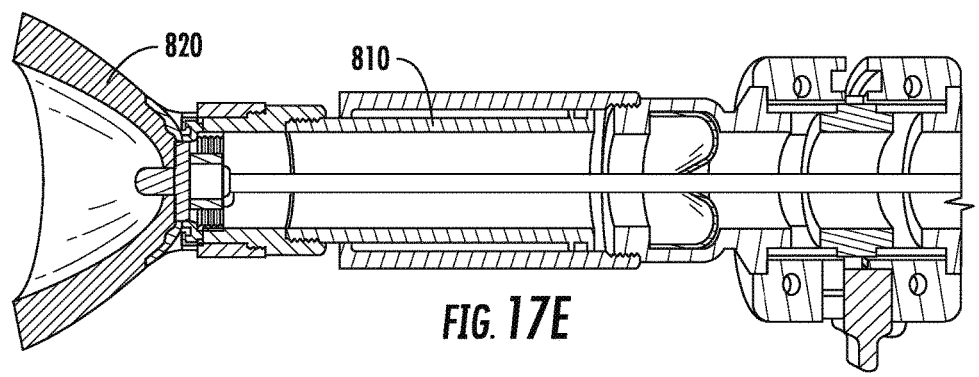
Figure 17F:
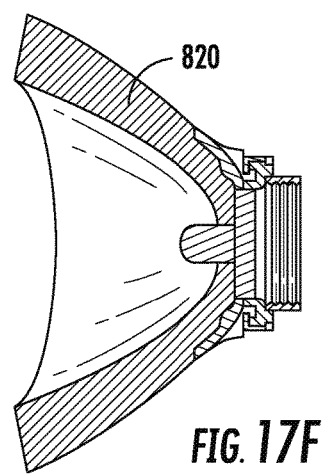

At FIG. 17C, after the piercing element 825 is removed from the proximal end of the outer lumen 810 and detached from the distal end of the inner lumen 805, the inner lumen 805 is re-inserted through the passage of the outer lumen 810, to provide communication through the tissue wall. While maintaining control of blood flow, such as by utilizing the flow control mechanisms described above, different medical instruments or devices may be used through the inner lumen 805 to treat, provide therapy, and/or diagnose conditions within the anatomical structure, as shown in FIG. 17D. After providing the desired procedure, therapy or diagnosis, the inner lumen 805 may be retrieved and a plug or other closure means is provided to the attaching device 820, as shown in FIG. 17E. At FIG. 17F, after having closed the attaching device 820 (or otherwise sealed the tissue), the outer lumen is removed from the attaching device 820 and the patient, leaving the attaching device 820 secured to the tissue wall. It is appreciated that, according to various embodiments, the attaching device 820 may be left implanted for a period of time or may be removed upon permanently sealing the tissue wall.

FIGS. 18A-18B illustrate schematic and cross-sectional views of a delivery system 100 that may be utilized with a guide wire, in accordance with one embodiment of the invention. Therefore, according to this embodiment, the delivery system 100 may be utilized as an over-the-wire system, which includes a guide wire (not shown), a dilator 510, in addition to the other delivery system 100 components, such as are described below.

In use, a guide wire is initially inserted into the ventricle, followed by a dilator 510 that carries the inner lumen 515. Thus, the dilator 510 includes an inner passage 505 that is adapted to pass over the guide wire. According to this embodiment, which may differ from various other embodiments, the inner lumen 515 can be delivered over the dilator 510 and inserted into the tissue wall prior to securing the attaching device 120 thereto. Upon positioning the inner lumen 515 through the tissue wall as desired, the outer lumen 520 carrying the attaching device 120 is advanced over the inner lumen 515 and secured to the tissue wall via the attaching device 120 (such as according to any means described herein or in the referenced patents or applications). According to one embodiment, a flow control mechanism, such as a collapsible diaphragm 135, as described with reference to FIGS. 14A-14C, may be actuated to seal the inner lumen 515 within the outer lumen 520. After positioning the outer lumen 520, the dilator 510 is retrieved allowing fluid communication through the tissue wall (e.g., into a ventricle, etc.). The guide wire may be retrieved at this stage, or at a previous stage such as after positioning the dilator 510.

Blood or other fluid flow through the inner lumen 515 may be controlled by a flow control mechanism, such as a duck bill valve 525 (or other valve mechanism, as described herein) at or near the proximal end of the inner lumen 515. The duck bill valve 525, or other valve mechanism, may therefore allow selective delivery of instruments or other therapeutic means through the inner lumen 515, while still limiting fluid loss through the proximal end of the inner lumen 515. Upon completion of the procedure, the inner lumen 515 may be retrieved and either the attaching device 120 or the tissue wall may be closed. For example, a small coil or other device for urging the tissue in an inward radial direction may be utilized to seal the tissue wall or a plug, cap, or other closure device may be secured to the attaching device 120 if the attaching device is left implanted. After removal of the inner lumen 515, the collapsible diaphragm 135 (or other flow control mechanism) may be utilized to limit or prevent fluid flow proximally through the outer lumen 510. Thus, a coil or other closure device delivery instrument may be inserted through the outer lumen 510 while the collapsible diaphragm 135 still serves to limit blood or other fluid flow through the outer lumen 510 while sealing the tissue wall or cap. It is appreciated that the delivery system 100 illustrated and described with reference to FIGS. 18A-18B may also include any other features, such as additional flow control mechanisms (e.g., globe valves, single or multiple leaflet valves, breast pump valves, diaphragm valves, rubber membranes, etc.), a steerable lumen tip, an extendable body section, a motion absorption element, a de-airing orifice, different attaching device configurations, or other features described herein or in the referenced patents and applications.

Figure 19A:
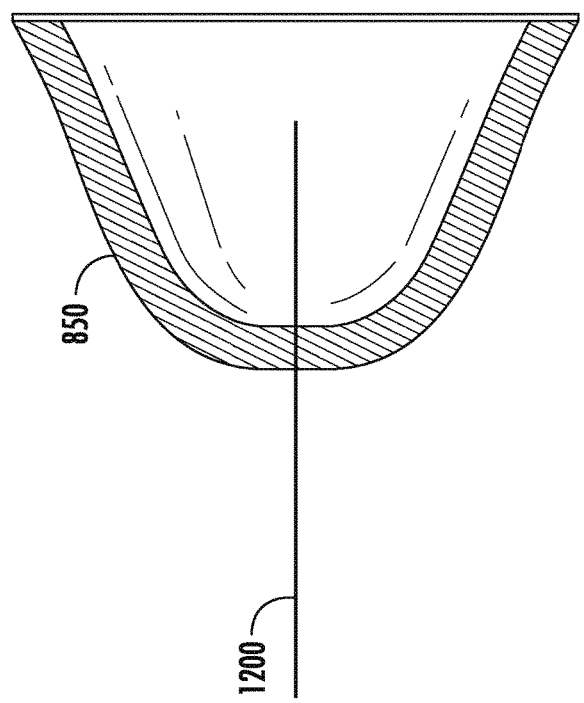
Figure 19B:
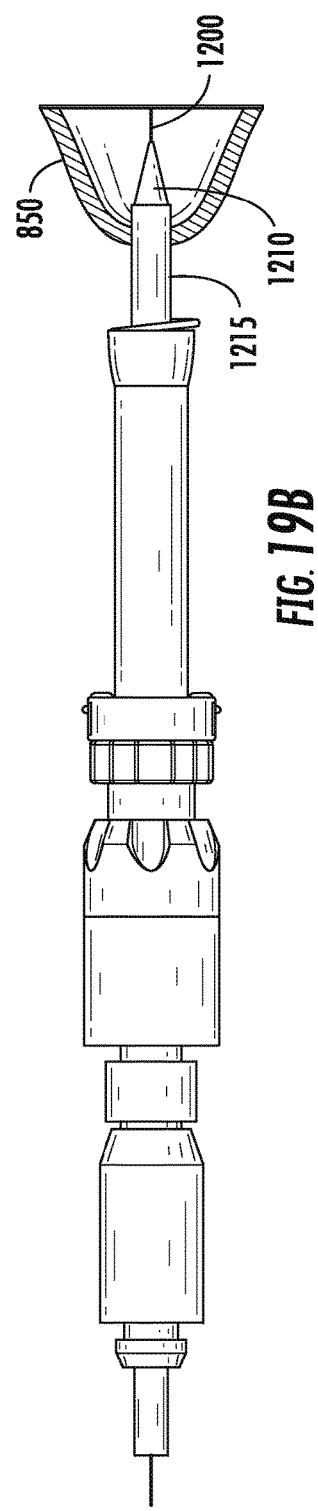
Figure 19J:
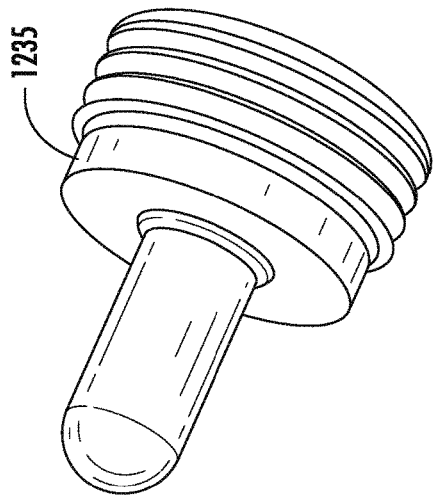
Figure 19I:
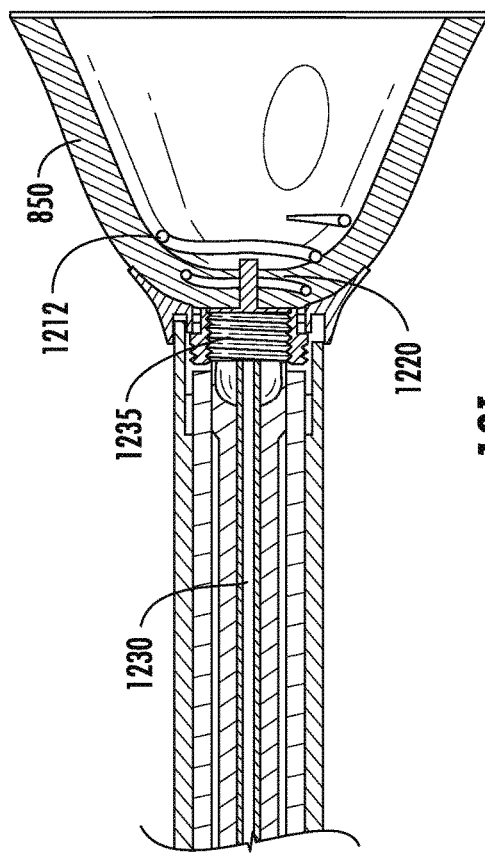
Figure 19K:
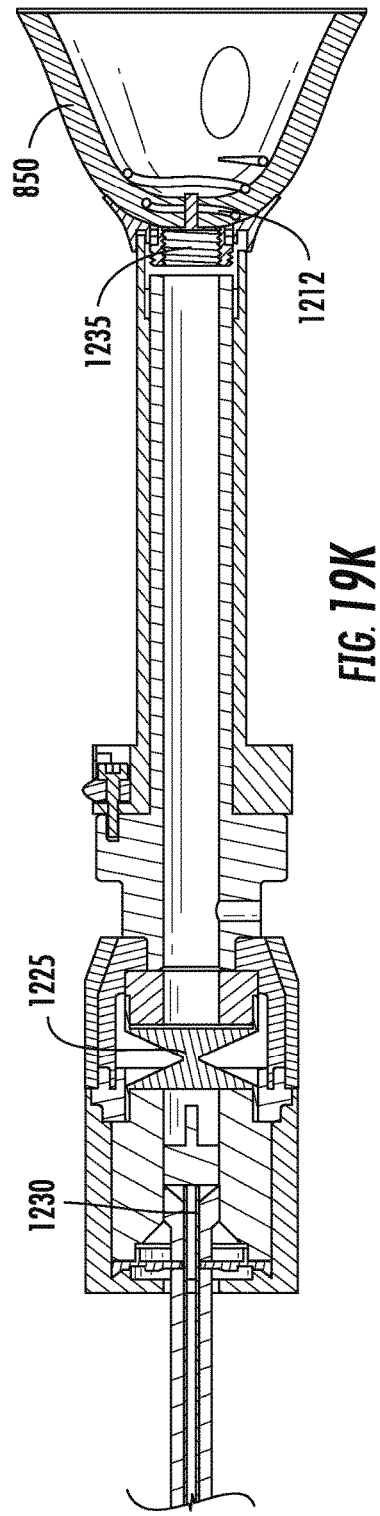
Figure 19L:
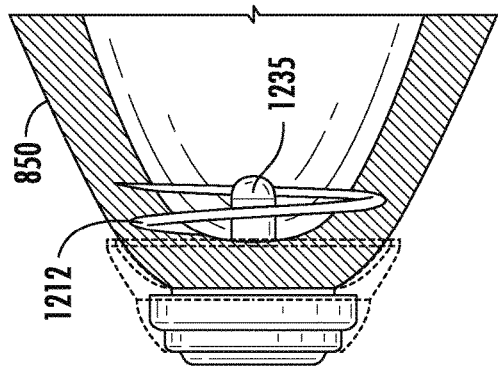

FIGS. 19A-19L show the main steps of a preferred "over the wire" procedure using the different components of the system described above. FIG. 19A illustrates a guide wire 1200 inserted in the access site of the tissue wall 850. FIG. 19B illustrates using the guide wire 1200 where the sheath 1215 is inserted riding on a dialator 1210. FIG. 19C illustrates a port 1220 anchored onto the ventricle by rotationally inserting the primary/anchoring coil 1212. FIG. 19D illustrates closure of the iris diaphragm valve 1225 stabilizing the sheath 1215 with respect to the conduit. FIG. 19E illustrates a dilator and guide wire removed. FIG. 19F illustrates the clinical procedure (introduction of an angioplasty balloon) performed through the port system. FIG. 19G illustrates the retraction of the sheath 1215 and closing of the iris diaphragm valve 1225 to prevent blood loss. FIG. 19H introduces the plug delivery tool 1230 into the system through sealing diaphragm before opening the iris diaphragm valve 1225. FIGS. 19I-19J illustrate the sealing of the orifice using the plug 1235. FIG. 19K illustrates detaching the plug delivery device 1230 from the plug 1235 and retracting. Closing the iris diaphragm is optional. FIG. 19L illustrates that the large coil 1212 is left in place after the plug 1235 is delivered. Many modifications to the steps of the procedure are possible as enabled by the various additional features described herein and depend on the specific clinical treatment desired.

FIG. 20 illustrates an example multiple access port device 1400 adapted for securing to the proximal end of an outer lumen. The multiple access port device 1400 may include multiple individual ports 1405a-1405n which are each in fluid communication with an attachment end 1410, and which allow using multiple different instruments to enter in communication with the outer lumen. All or a portion of the multiple access port device 1400 may be configured from a biocompatible pliable material, such as from a natural or synthetic rubber, or other polymer material, allowing flexible use of the individual ports 1405a-1405n. The attachment end 1410 can releasably (or permanently) secure to the proximal end of the outer lumen, providing fluid communication from each of the individual ports 1405a-1405n to the inner passage of the outer lumen.

The multiple access port device 1400 may further include one or more flow control mechanisms, which may be in operable communication with one or more of the individual ports 1405a-1405n and/or with the converging portion of the device 1400. The flow control mechanisms may be any mechanism allowing selective flow through the respective passage, such as, but not limited to, clamp valves, duck bill valves, globe valves, single or multiple leaflet valves, breast pump valves, diaphragm valves, and the like. In addition, one or more de-airing orifices 1415, as are known, may be included with the multiple access port device 1400 to prevent introducing air into the patient's vasculature during use. In other embodiments, however, the de-airing orifice may be associated with the outer lumen 810 or another portion of the system. Although the multiple access port device 1400 is shown and described as being attached to the outer lumen, in other embodiments, a multiple access port device 1400 may be attached directly to the attaching device or attached to the inner lumen.

FIGS. 21A-21B illustrate various embodiments of a delivery system having an inner lumen with a steerable tip. For example, as shown in FIG. 21A, the inner lumen 300 may be directed in two or three dimensions in order to direct the therapeutic devices passing through the lumen 300 in the desired direction. According to the embodiment, as shown in FIG. 21A, the steerable tip 305 may be guided utilizing a distal section that is flexible and a system of wires, rods, or other members extending proximally for use by the operator to exert forces at different sections of the steerable tip 305, deforming the lumen 300 in a controlled direction. The steerable tip 305 may be achieved according to techniques similar to those utilized for steerable catheters, as are known.

FIG. 21B illustrates another embodiment of a steerable inner lumen 400. According to this embodiment, a guide wire 405 is provided over which the inner lumen 400 is passed and a guiding tip 410 is provided, extending from the distal end of the inner lumen 400. The guiding tip 410 may have a curved shape (or other preformed shape) such that the guiding tip 410 causes the guide wire 405 to approximately follow the curve of the guiding tip 410. As the guide wire curves, so will the inner lumen 400. To provide additional degrees of freedom or movement, the inner lumen 400 may be rotated about its longitudinal axis to achieve improved steering of the distal end of the inner lumen. According to one embodiment, the guiding tip 410 includes a guide 415, such as a ring, an eye, a channel, etc., which maintains the relationship of the guide wire 405 and the guiding tip 410. Furthermore, a control mechanism 420, such as a handle, a trigger, or other suitable means, may be in operable control with the guiding tip 410 to allow extending or retracting the guiding tip 410 and/or to rotate the guiding tip 410 and/or the inner lumen 400. In further embodiments the inner tube with steerable tip, may be a medical catheter or sheath with an steerable distal end. This sheath or catheter may be steered by tension on a single or multiple wires which run axially within the wall of the device.

FIGS. 22-23C illustrate perspective views of yet additional embodiments of an inner lumen, in which the inner lumen is configured as a collapsible inner lumen. Accordingly, a collapsible inner lumen may be expandable and/or collapsible in order to allow delivery of the lumen endovascularly or trans-cutaneously, such as within a catheter or insertion sleeve. Therefore, a collapsible inner lumen can collapse to a compressed state, having a smaller diameter, allowing inserting through a smaller orifice, such as may be utilized during endovascular or trans-cutaneous procedures. After insertion and placement, the collapsible inner lumen can be expanded to provide a passage having an increased diameter to allow inserting instruments and/or administering therapy therethrough.

Moreover, a collapsible lumen may further facilitate sealing a tissue puncture when inserted therethrough and expanded to its expanding state by creating an outward radial force against the tissue walls. It is thus possible that, in embodiments using a collapsible/expandable inner lumen, an attaching device need not be a radially expanding coiled device or other device that urges tissue in an inward radial direction because the collapsible/expandable inner lumen creates the pressure by urging itself in an outward radial direction when in an expanded state. It is appreciated that, in some embodiments, an attaching device, an outer lumen, and/or any other aspects of the system may likewise be collapsible to allow delivery by trans-cutaneous access.

Figure 22A:
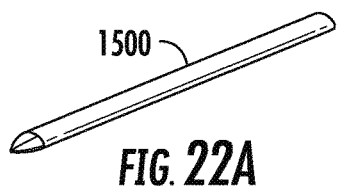
Figure 22B:
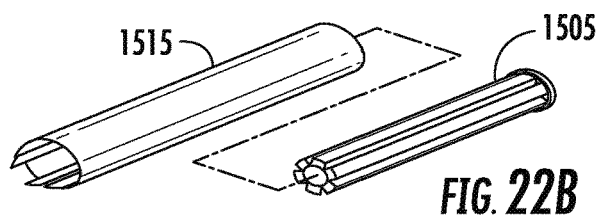
Figure 22C:
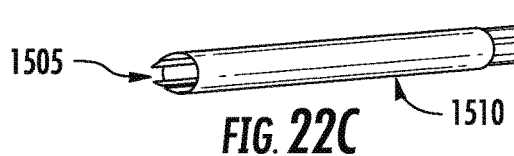
Figure 22D:

FIGS. 22A-D, thus, show a collapsible inner lumen 1500 in a collapsed (FIGS. 22A and 22D) and expanded (FIGS. 22B and 22D) state. A collapsible inner lumen 1500 may generally include an expanding member 1505 and an expandable membrane 1510 provided over the expanding member 1505. Also as shown in FIG. 22A, in one embodiment, a collapsed inner lumen 1500 may serve as a piercing device by forming a substantially sharpened tip when the expanding member 1505 is in a collapsed state. The piercing device may be utilized to puncture or otherwise open the tissue through which the lumen 1500 is to be inserted. The expanding member 1505 of FIGS. 22B and 22C is shown as a series of elongated members (e.g., expandable barbs, etc.) that may be mechanically operated to expand and/or collapse.

FIGS. 23A-23C illustrate other embodiments of a collapsible inner lumen. With reference to FIG. 23A, an expanding member 1520 may be configured as an expanding coil wire or helical ribbon selectively expandable within a tube-shaped membrane 1510. FIG. 23B illustrates a different expandable member 1525 configured in an expanding mesh configuration, such as is utilized for an expanding mesh stent. In one embodiment, a membrane 1510 is also provided for use with the expanding mesh member 1525. Though, in other embodiments, the expanding mesh member 1525 may be configured for use without a separate membrane, whereby the mesh arrangement provides a substantially closed surface in an expanded or collapsed state. FIG. 23C shows yet another embodiment of an expanding member 1530 configured as an expanding helix, which expands radially when removed from the membrane 1510 to unwind, in a manner similar to an unwinding ribbon. Any of the various expanding members 1505, 1520, 1525, 1530 described herein may be configured to expand and/or collapse using one or more of: mechanical actuation, inflation, material properties, structural properties, electrical excitation, thermal excitation, and/or any combination thereof.

FIGS. 24A-24B illustrate an example embodiment in which the distal end or tip 1705 of a collapsible inner lumen 1500 is flexible, allowing it to serve as a valve or port. For example, as shown in FIGS. 24A-24B, according to one embodiment, the flexible tip 1705 may generally be in a closed state until an instrument 1710 (or any other member) forces separable portions of the tip 1705 apart into an open state. A flexible tip 1705 may thus be utilized to control access through the inner lumen 1500 and/or to control fluid flow through the inner lumen 1500. Moreover, in some embodiments, the ability to selectively control fluid allows for leaving the inner lumen 1500 implanted within a tissue wall to enable multiple subsequent accesses therethrough. In some embodiments the distal tip of the closure plug may be flexible and serve as a valve or port as described below. This expandable and/or flexible tip of the closure plug may therefore allow for re-access after closure.

According to various embodiments, an attaching device may be closed and/or the tissue wall puncture may be substantially sealed to close the puncture, to prevent fluid flow therethrough, and/or to allow multiple subsequent accesses. FIGS. 25A-25B illustrate various example embodiments of an attaching device 820 which is adapted to receive a plug 1800 to substantially seal the attaching device 820. As shown in FIG. 25A, a plug 1800 may include a plug end 1805 and an opposite threaded end 1810. The plug 1800 is sized and shaped to releasably fit within the attaching device 820, being inserted from the proximal direction. According to this embodiment, the attaching device 820 has inner threads 1815 that are complementary to the threads 1810 of the plug 1800, as shown in FIG. 25B. It is appreciated, however, that any number of releasably attaching techniques can be utilized to secure the plug 1800 to the attaching device 820. Upon insertion, the distal plug end 1805 fits within a cavity 1820 of the attaching device 820, which would otherwise provide fluid access therethrough.

FIGS. 26A-26B illustrate an example embodiment of a plug 1800, which includes an extended surface 1905 extending from a plug end 1805. The extended surface 1905 is intended to fit within the puncture or perforation of the tissue wall so as to further improve the sealing abilities of the plug 1800 and the attaching device 820 generally by deforming the tissue and creating a seal between the plug end 1805 and the tissue and/or between the tissue and the attaching device 820 (e.g., a flange, ring, etc.). According to one example embodiment, the extended surface 1905 may have a smaller diameter than the plug end 1805. In one embodiment, as shown in FIG. 26B, a conical flange and/or conical coil of the attaching device 820 may further improve sealing by creating an inward radial force and urging the tissue against the extended surface 1905. As described above, the distal tip of the closure plug may have a flexible valve or port, or self-sealing membrane, to provide re-access to the tissue after closure. FIG. 26C illustrates another example embodiment of a plug 1800, which similarly includes an extended surface 1905 extending from a plug end 1805. In contrast to the above-described embodiments, the plug 1800 of FIG. 26C includes a non-threaded attachment mechanism for attaching the plug to the attaching device 820. The non-threaded attachment mechanism may include one or more clips 1830, as shown, for attaching the plug 1800 to the attaching device 820. According to this embodiment, the attaching device 820 may include a complementary feature, such as a ridge or protrusion, for releasably engaging the clips 1830. According to other embodiments, the non-threaded attachment mechanism may include hooks, tabs, pins, or other mechanical attachment mechanisms. Still other non-threaded attachment mechanisms, such as magnetism, glues or other chemical methods, may be used for attaching the plug 1800 to the attaching device 820.

FIGS. 27A-27B illustrate perspective views of alternative embodiments of plug and coil closure systems provided by the invention. FIG. 27A shows a plug 1800 (or cap) for occluding the attaching device orifice, similar to the plug of FIGS. 19J and 26A, having a threaded exterior surface for engaging corresponding threads on the interior orifice of the attaching device 820. The plug configuration permits closure of the conduit with a minimal protruding profile. The plug 1800 can be constructed of any suitable materials, including biocompatible rigid polymers or metal alloys, and biodegradable materials. In certain embodiments, the surfaces of the plug and/or orifice of the attachment device can be coated with a biocompatible swellable composition, such as a collagen gel, to facilitate sealing between the plug and the attachment device. The plug can also be coated or impregnated with bioactive agents, such as but not limited to thrombolytics, growth factors, angiogenic agents, and antibiotics. The surfaces of the plug and attaching device embodiments can also be made textured or porous, such as through casting and laser etching techniques, in order to facilitate tissue ingrowth for improved immunological acceptance of the implantation.

FIGS. 27A-27B also illustrate a delivery instrument 2005 configured for delivering a plug 1800 through an extended lumen and for insertion into an attaching device 820. The delivery instrument 2005 may be configured with an engagement element 2010 adapted to releasably attach to a plug 1800 and to allow rotating the plug 1800 during insertion into and removal from an attaching device 820. In one embodiment, the engagement element 2010 can be a substantially solid end piece that includes a receiving feature (e.g., the female or male element of a corresponding male/female element on the plug 1800), such as, but not limited to, a straight slot, cross-shaped slot (e.g., for use with a phillips head), a hexagonal shape (e.g., for use with an allen head), or any other geometry or assembly that allows secure selective insertion of the head of a delivery instrument 2005 into a complementary feature on the plug 1800. According to other embodiments, any other mechanical forces, suction forces, or magnetic forces, or any combination thereof, may be utilized as part of the engagement element 2010 to provide releasable engagement of the delivery instrument 2005 with the plug 1800.

FIGS. 28A-28B illustrate yet additional closure or sealing devices, which operate by compressing or collapsing the tissue at the puncture site in the tissue wall. According to this embodiment, the attaching device 820 includes a variable radius coiled member 2105 for inserting into the tissue wall and securing the attaching device 820 to the tissue wall. The variable radius coiled member 2105 may have a relaxed state 2105a, as shown in FIG. 28B and an expanded state 2105b, as shown in FIG. 28A. In its relaxed state 2105a, the coiled member 2105 includes a narrow section 2110 having a decreased radius relative to other portions of the coiled member 2105. In its expanded state 2015b, the narrow section 2110 is expanded such that the radius is greater than in its relaxed state. Thus, when the coiled member 2105 changes from its expanded state to its relaxed state, the tissue is compressed in an inward radial direction at or near the narrow section 2110, which in turn facilitates sealing the tissue puncture. This type of coil by itself or with other elements may serve to close a puncture or bore in tissue. An hour glass shaped coil may also have the closure effects described above.

According to certain embodiments, the coiled member 2105 may be made of a shape memory material (e.g., a shape memory alloy, such as Nitinol, etc.) that will change in shape after deployment into the tissue wall, causing the puncture or gap in the tissue wall to seal. For example, the coiled member 2105 made of shape memory material may be maintained in the expanded state 2015*b*, as shown in FIG. 28A, prior to and during deployment into the tissue wall. Then, after deployment into the tissue wall, the coiled member 2105 made of shape memory material may be acted on to cause the coiled member 2105 to change into the relaxed state 2015*a*, as shown in FIG. 28B. In this manner, when the coiled member 2105 changes from the expanded state 2015*b* to the relaxed state 2015*a*, the tissue is compressed in an inward direction at or near the narrow section 2110, which in turn facilitates sealing of the tissue puncture. According to one embodiment, the coiled member 2105 may have a generally straight shape (i.e., a coil having a constant radius along the length of the coil) when in the expanded state 2015*b* and a generally conical shape (i.e., a coil having an increasing radius along the length of the coil) when in the relaxed state 2015*a*. Other shapes may be used when the coiled member 2105 is in the expanded state 2015*b* and the relaxed state 2015*a* in order to achieve sealing of the puncture in the tissue wall. In some embodiments, the attaching device may include more than one coiled member 2105, at least one of which may be made of a shape memory alloy and configured to change from an expanded state to a relaxed state for sealing purposes. Further, other closing elements may be used instead of the coiled member 2105 of FIGS. 28A-28B, such as one or more hooks or pin structures. Such closing elements similarly may be made of a shape memory material that will change in shape after deployment into the tissue wall, causing the puncture or gap in the tissue wall to seal.

In the embodiment shown by FIG. 28A-28B, the variable radius coiled member 2105 may be forced into an expanded state 2105*b* when a plug 1800 (or a lumen or other member) is inserted through the approximate center of the coiled member 2105 and expanding the narrow section 2110, as shown in FIG. 28A. Thus, when the plug 1800 (or a lumen or other member) is removed, the coiled member 2105 reverts to its relaxed state 2105*a*, allowing the narrow section 2110 to compress the tissue inward and seal the tissue wall.

It is appreciated that, in other embodiments similar to that shown in FIGS. 28A-28B, instead of (or in addition to) a coiled member, one or more barbs, wires, or pins may be configured to generally extend from the attaching device inward, but allow expansion or displacement by a plug or other member. Thus, similar to that shown in FIGS. 28A-28B, removal of the plug or other member would cause the barbs, wires, or pins to compress inward and achieve tissue sealing in much the same manner. It is further appreciated that, in these and/or other embodiments, any of the members may be constructed from shape memory materials (e.g., a shape memory alloy, such as Nitinol, etc.) that may be acted on to induce reverting to its relaxed state, as known, and cause inward compression of the tissue wall.

FIGS. 29A-29B show another embodiment for achieving closure of the tissue wall. According to this embodiment, an attaching device 820 may include one or more pledgets 2205 associated therewith and one or more sutures 2210 to be releasably inserted through the pledgets 2205 and a portion of the attaching device 820. Thus, the sutures 2210 and/or pledgets 2205 may be used to initially close the tissue wall after removal of the inner tube but before removing the attaching device 820. According to one embodiment, the pledgets 2205 may be pre-mounted onto an inner surface of the attaching device 820 (or flange), such that they can be left behind on the surface of the tissue when the attaching device 820 is removed. In a further embodiment of the device the inner lumen or conduit may be withdrawn from the tissue by adjusting a multiple position lock before tightening the suture, so that the inner lumen does not interfere with the closure of the tissue. During a procedure, the U-sutures or mattress sutures 2210 may be passed through the pledgets 2205 to close the tissue wall. In other embodiments, the sutures 2210 may be pre-mounted onto the attaching device 820 and through the pledgets 2205. Tightening the sutures 2210 will cause them to pass through and separate from the attaching device 820 and close the tissue wall, as is known. It is appreciated that the sutures 2210 and/or pledgets 2205 may be utilized with any of the attaching device and/or conduit embodiments described herein.

FIGS. 30A-30B illustrate additional embodiments for achieving closure of a tissue wall. According to some embodiments, an attaching device may include an outer coil and an inner coil positioned within the outer coil, both coils being implanted into the tissue wall for closing the puncture. In this manner, the outer coil may provide initial inward compression of the tissue wall, and the inner coil may provide secondary inward compression of the tissue wall. According to other embodiments of an attaching device, other tissue attachment elements, such as pins, may be used instead of the inner coil and the outer coil. Further embodiments of an attaching device may include a combination of coils, pins, or other tissue attachment elements.

According to the embodiment of FIG. 30A, the attaching device 820 includes an outer coil 2350 and an inner coil 2355 for attaching to a tissue wall 2300. The tissue wall 2300 is illustrated has having a first surface 2305 (e.g., an outer surface), a second surface 2310 (e.g., an inner surface), and a puncture 2315 defined therein. The outer coil 2350 can be rotatably inserted into the tissue wall 2300, proving initial inward compression of the tissue wall 2300. The inner coil 2355 similarly can be rotatably inserted into the tissue wall 300, providing secondary inward compression of the tissue wall 2300. In this manner, the outer coil 2350 and the inner coil 2355 may cooperate to compress the tissue and close the puncture 2315.

According to one example embodiment of using the attaching device 820, the outer coil 2350 may be inserted into the tissue wall 2300 to initially secure a conduit device (not shown, such as if already removed) extending through the tissue wall 2300 by compressing the tissue wall 2300 inward against the conduit and creating a substantial seal therewith. For example, after inserting the outer coil 2350 at least partially through the tissue wall 2300 (inserting from the first surface 305), a coring device may be passed through the approximate center of the outer coil 2350 to puncture the tissue wall 2300 and optionally remove a portion thereof. After defining the puncture 2315 (already shown in FIG. 30A in a closed state) through the tissue wall 2300, a conduit may be inserted therethrough, providing fluid communication between the first surface 2305 and the second surface 2310 of the tissue wall 2300 (e.g., into a ventricle if the tissue wall 300 represents a cardiac apex, etc.).

As described above, the increasing radius of the outer coil 2350 will compress the tissue of the tissue wall 2300 inwardly to seal against the conduit. Upon removing the conduit, which may be performed during and/or after the corresponding surgical procedure, the inner coil 2355 may be rotatably inserted through the approximate center of the outer coil 2350 (through the opening 2365 of the flange 2360) and at least partially through the tissue wall 2300, surrounding the puncture 2315 created in the tissue wall 2300. The increasing radius of the inner coil 2355, in combination with its reduced coil diameters relative to the outer coil 2350, allow the inner coil 2355 to further compress the tissue wall 2300 to substantially close the puncture 2315, minimizing or eliminating fluid flow therethrough. In some circumstances, the outer coil 2350 may be removed, leaving the inner coil 2355 within the tissue wall 2300 and substantially sealing the puncture 2315. Therefore, the inner coil 2355 is shown in FIG. 30A having been inserted for closing a tissue wall 2300 with the accompanied use of the outer coil 2350. However, in other embodiments, the inner coil 2355 may be utilized separately without the prior use of the outer coil 2350 or after the outer coil 2350 (or other supporting element) has been removed.

FIG. 30B shows another embodiment of an attaching device 820 including an outer coil 2350 and an inner coil 2355 for attaching to a tissue wall 2300. According to this embodiment, the outer coil 2350 has a conical shape with an increasing radius along the length of the outer coil 2350, and the inner coil 2355 has a straight shape with a substantially constant radius along the length of the coil 2355. In use, the outer coil 2350 will provide greater inward compression of the tissue wall 2300 for closing the puncture 2315 as compared to the inner coil 2355. The inner coil 2355 will still provide a degree of inward compression toward the puncture 2315 due to displacement of a portion of the tissue, however the inner coil 2355 will function primarily to stabilize the tissue and prevent expansion or tearing of the tissue wall 2300 about the puncture 2315. The inner coils 2315, 2355 and/or the outer coils 2350 can be made of a shape-memory material, and function such as described with respect to FIGS. 28A-28B, to improve sealing.

FIGS. 31A-31C illustrate yet additional embodiments for achieving closure of a tissue wall. According to some embodiments, an attaching device may include supporting elements that support and/or urge tissue inward, which may not include outer coils. According to these embodiments, instead of a radially expanding coil, other apparatuses can be utilized to be inserted at least partially into the tissue wall and/or at secured to one or more surfaces of the tissue wall to prevent further expansion of the tissue wall. Such apparatus may be beneficial with tissues that are prone to tearing (e.g., cardiac tissue, etc.), that may otherwise result in an undesirable increase in puncture size either during the surgical procedure or during or after attempting to close the puncture.

According to the embodiment of FIG. 31A, an attaching device 820 includes a pinned supporting element 2405 including multiple straight pins or needle members 2410 extending from a flange 2415 and adapted for insertion at least partially through a tissue wall 2300 to prevent further tearing or expansion of a puncture 2315. In this embodiment, instead of a coil being rotatably inserted into a tissue wall 2300, the pins or needle members 2410 may be pushed straight into and at least partially through the tissue wall 2300, providing support to the tissue wall 2300. According to one embodiment, the pins or needle members 2410 may have a sharpened distal end. In one embodiment, the pins or needle members 2410 may extend from the flange 2415 in a radially spaced apart pattern, forming a circular or semicircular pattern that will encircle a tissue puncture 2315 site. However, in other embodiments, other configurations may be utilized. Similar to that described with reference to FIG. 30A, an inner coil 2420 may be inserted through the center opening of the flange 2415 and into the tissue wall 2300 to compress the tissue and substantially close the puncture 2315. It is appreciated that the pinned supporting element 2405 and flange 2415 may be formed from materials and in manners similar to that described herein with reference to the outer coil 2350 and/or the inner coil 2355.

In some embodiments, the pinned supporting element 2405 may be made of a shape memory material that will change in shape after deployment into the tissue wall, causing the puncture 2315 or gap in the tissue wall 2300 to seal. For example, the pinned supporting element 2405 made of shape memory material may be maintained in an expanded state, as shown in FIG. 31A, prior to and during deployment into the tissue wall. Then, after deployment into the tissue wall, the pinned supporting element 2405 made of shape memory material may be acted on to cause the pins or needle members 2410 to angle inward in a relaxed state. In this manner, when the pinned supporting element 2405 changes from the expanded state to the relaxed state, the tissue is compressed in an inward direction to facilitate sealing of the tissue puncture 2315.

FIGS. 31B-31C illustrate another example embodiment of a pinned supporting element 2455 as may be included in an attaching device 820, the pinned supporting element 2455 having multiple pins or needle members extending therefrom. The pinned supporting element 2455 may be used by itself or in conjunction with one of the various closing element embodiments, such as the inner coil 2420 described above. According to the embodiment of FIGS. 31B-31C, the pinned supporting element 2455 includes a flexible sleeve 2460 and a rigid guide 2465. The flexible sleeve 2460 includes flexible pins or needle members 2470 that angle outward from a base 2475 of the flexible sleeve 2460, while the rigid guide 2465 includes guide pins 2480 that angle outward from its base 2485. Thus, during delivery, the guide pins 2480 of the rigid guide 2465 are inserted into the pins or needle members 2470 of the flexible sleeve 2460, causing the flexible pins or needle members 2470 to compress the tissue wall 2300 inward toward the puncture 2315. During delivery, the flexible sleeve 2460 is first inserted through the tissue wall 2300 to support and stabilize the tissue, and the rigid guide 2465 is inserted into the flexible sleeve 2460 when an inward compressive force is desired, such as when closing the puncture site 2315.

FIGS. 32A-32B illustrate further embodiments for achieving closure of a tissue wall. According to these embodiments, an attaching device may include a series of pins or anchors and one or more elastic bands. For example, FIG. 32A shows an attaching device 820 including a series of pins 2505 or anchors that may be delivered into the tissue around the site of a puncture as a supporting element. The pins 2505 may then be selectively connected by one or more elastic bands 2510 as a closing element to facilitate closing of the puncture. According to the embodiment of FIG. 32A, five pins 2505 surrounding the puncture site extend from the tissue surface to coordinate with one band 250 of the closing element. FIG. 32B illustrates another embodiment of an attaching device 820 including six pins 2505 surrounding the puncture site and extending from the tissue surface to coordinate with two bands 2510. It is appreciated that any number of pins and bands may be used to coordinate inward compression of the tissue for sealing the tissue puncture. During delivery of the pins 2505, the elastic bands 2510 are maintained in an extended state. When the pins 2505 are in place, partially or completely in the tissue encompassing the puncture site, delivery tools which maintain the elastic bands 2510 in an extended position can be released, therefore allowing the elastic bands 2510 to recoil to their normal geometry around the pins 2505. The mechanical recoil of the bands 2510 and the pattern of the pins 2505 around the site of the puncture will then generate an inward compression toward the puncture site through the tissue, closing the puncture orifice and preventing fluid or blood loss therethrough.

FIG. 33 illustrates another embodiment for achieving closure of a tissue wall with a suture 2600. The suture 2600 may be deployed helically within the tissue wall 2300 by a hollow coil member or guided needle. In some embodiments, the suture 2600 may be deployed by a hollow coil member having an increasing radius or a substantially constant radius. After deploying the suture 2600, a distal end of the suture 2600 may be anchored to the tissue wall 2300 by a securing member 2610 as shown. The securing member 2610 may be adapted to engage the inner surface 2310 (or other portion) of the tissue wall 2300. According to various embodiments, the securing member 2610 may include one or more pins, hooks, flat tabs, plugs, prongs, barbs, expanding members, jointed members, or other interfering members and the like. FIG. 33 shows the suture 2600 deployed in the tissue wall 2300 in a loose state prior to tightening within the tissue wall 2300 and prior to substantially sealing the puncture 2315. The suture 2600 then may be tightened to substantially close the puncture 2315. The suture 2600 may be retained within the tissue wall 2300 by the resistance applied by the securing member 2610. In the embodiment shown, the securing element 2610 is urged against the inner surface 2310 of the tissue wall 2300. However, in other embodiments, the securing element 2610 may be lodged at an intermediate position within the tissue wall 2300 or at an intermediate position within the puncture 2315 (e.g., such as if configured as a hook, barb, or plug). Pulling the proximal end of the suture 2600 will tighten the suture within the tissue wall 2300 and close the puncture 2315.

Figure 34A:
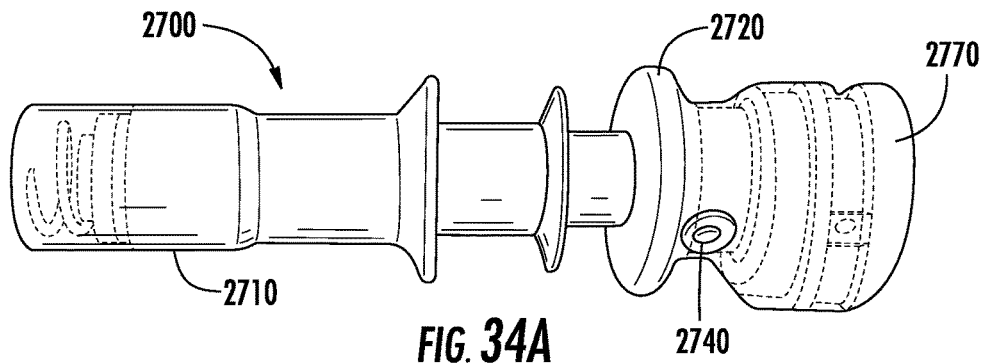
Figure 34B:
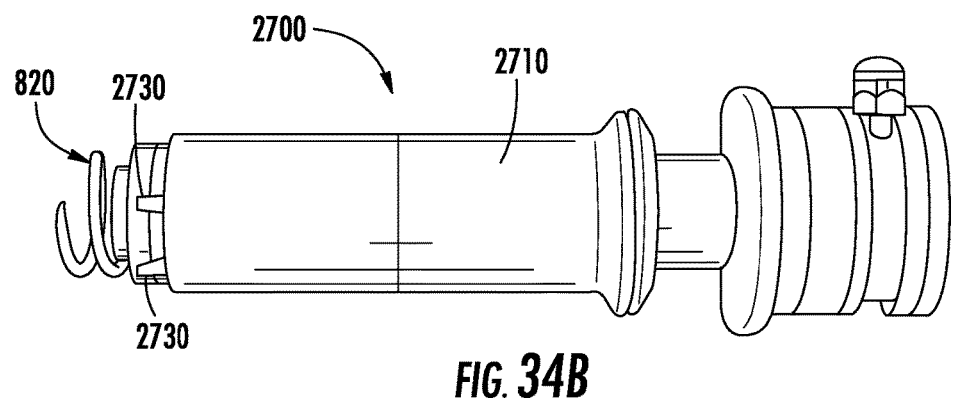
Figure 34C:
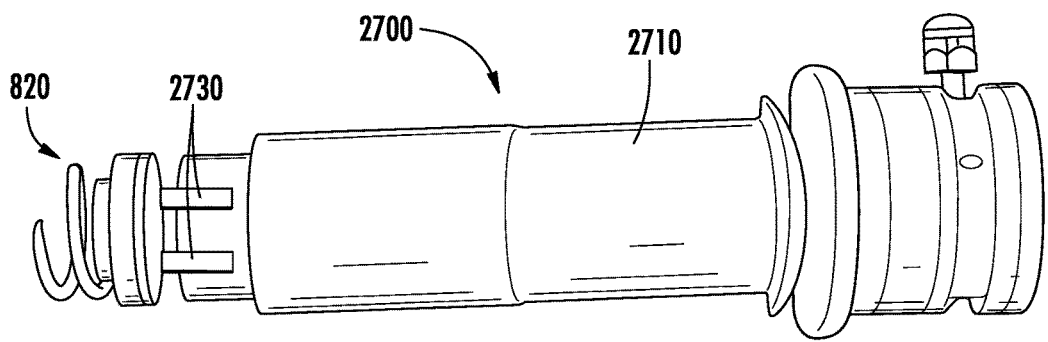
Figures 34D, 34E:
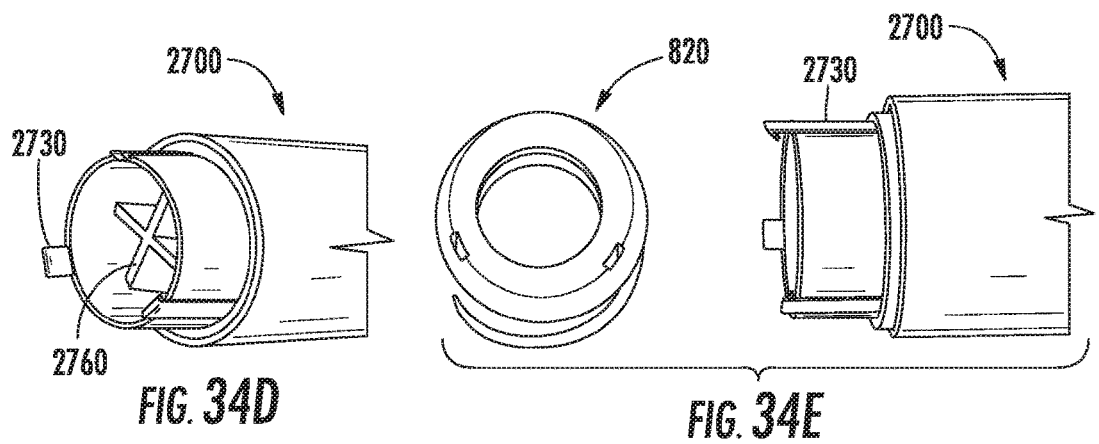
Figure 34F:
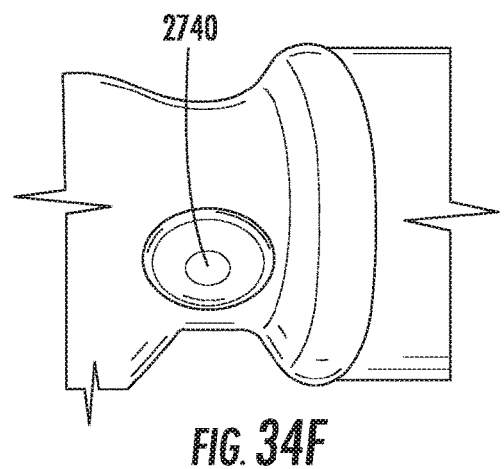
Figure 34G:
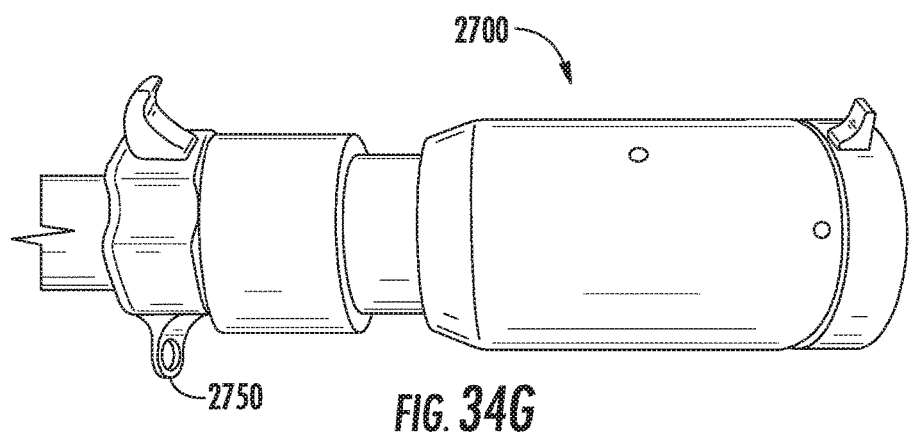

FIGS. 34A-34F illustrate another embodiment of a delivery system 2700 for delivering an attaching device 820 into a tissue wall. According to this embodiment, the delivery system 2700 includes a protective sheath 2710 for removably covering the attaching device. As is shown, the protective sheath 2710 may be slidably connected to a handle portion 2720 of the delivery system 2700. In this manner, the protective sheath 2710 may be moved between a deployed position (FIG. 34A), a partially retracted position (FIG. 34B), and a fully retracted position (FIG. 34C). When in the deployed position, the protective sheath 2710 covers the attaching device 820, including any sharp elements on the distal end of the attaching device 820 such as a sharpened coil, pin, or needle. In this manner, the protective sheath 2710 prevents the attaching device 820 from catching or becoming entangled with any structures when being moved towards the anchoring location. The delivery system 2700 also includes a threadless connection mechanism for connecting the delivery system 2700 to the attaching device 820. According to some embodiments, the threadless connection mechanism may include one or more clips 2730, as shown, for releasably connecting to the attaching device 820. When the protective sheath 2710 is in the deployed position, the protective sheath 2710 prevents the clips 2730 from releasing the attaching device 820. In contrast, when the protective sheath 2710 is in the fully retracted position, the protective sheath 2710 allows the clips 2730 to disengage from the attaching device 820, permitting the attaching device 820 to release from the delivery system 2700. According to other embodiments, the threadless connection mechanism may include one or more prongs, hooks, wires, magnetics, interference mechanical elements, or combinations thereof.

According to certain embodiments, the delivery system 2700 also may include a push-button air bleed 2740. The air-bleed 2740 may be constructed of a soft material such that when depressed or pulled, the air-bleed opens one or multiple channels and allows air to escape from a selected site in the delivery system 2700. In other embodiments, air-bleed 2740 may include spring-actuated buttons or other movable rigid or partially rigid elements that open the air-bleed channels when activated. In some embodiments, the delivery system 2700 may include a pacing lead bridge 2750 configured to transmit electrical current to the heart through the attaching device 820, such as through a coil thereof, in order to control beating of the heart. In some embodiments, the delivery system 2700 may include a distal valve 2760, such as a multi-leaflet valve, positioned near a distal tip of the delivery system 2700. In this manner, the distal valve 2760 may be configured to minimize blood loss through the cavities of the delivery system 2700. In some embodiments, the delivery system 2700 may include a proximal valve 2770, such as a collapsing diaphragm valve, positioned near a proximal end of the delivery system 2700, such as within the handle 2720. In this manner, the proximal valve 2770 may be configured to allow for different aperture levels for the shaft of the delivery system 2700.

FIGS. 35A-35C illustrate another embodiment of an attaching device 820 including a secondary sealing element, as may be beneficial in certain applications to complement or supplement the inward compression provided by a coil. Specifically, the attaching device 820 may include an inner skirt 2810 or ring positioned within a coil 2820. In some embodiments, the inner skirt 2810 may be attached to a distal end of an outer ring 2830 of the attaching device 820. As shown in FIG. 35B, the inner skirt 2810 may press or compress against the outer surface of the tissue wall when the coil 2820 is inserted into the tissue wall. In this manner, the inner skirt 2810 may form a secondary seal against the tissue wall. In some embodiments, the inner skirt 2810 may be configured to enter into the puncture in the tissue wall, thereby opposing the inward compression of the tissue generated by the coil 2820.

In other words, the above embodiment of the invention provides a system for sealing a device having an outer base ring defining an opening therethrough and a distally projecting tissue attachment element; and an annular sealing flange distally attached to the outer base ring inside the tissue attachment element defining a first circumference and distally projecting for interfacing with the tissue surface to create a fluid tight seal. In certain embodiments, the tissue attachment element is a coil, and the tissue is a heart.

FIGS. 36A-36B illustrate another embodiment of an attaching device 820 including a secondary sealing element, as may be beneficial in certain applications to complement or supplement the inward compression provided by a coil. Specifically, the attaching device 820 may include an inward facing flange 2910 positioned outside of a coil 2920. In some embodiments, the inward facing flange 2910 may be attached to a distal end of an outer ring 2930 of the attaching device 820. In use, the inward facing flange 2910 may press or compress against the outer surface of the tissue wall when the coil 2920 in inserted into the tissue wall. In this manner, the inward facing flange 2910 may form a secondary seal against the tissue wall. Due to its inward facing configuration, the flange 2910 will seal against the outer surface of the tissue wall without the need for full deployment or penetration of the coil 2920. Specifically, as the distal portion of the flange 2910 contacts the tissue wall, the pressure of the fluid trying to escape outward through the tissue wall will bias the flange 2910 outward, as if it were a leaflet, enhancing the seal of the flange 2910 against the tissue wall.

In other words, in the above embodiment the invention provides a system for sealing attached to a tissue surface comprising: a tissue attaching device attached to a tissue surface comprising: a tissue attaching device having an outer base ring defining an opening therethrough and a distally projecting tissue attachment element; and an annular sealing flange distally attached to the outer base ring outside the tissue attachment element defining a first circumference and distally projecting at an inward angle to define a second circumference for interfacing with the tissue surface surrounding the attachment element, wherein the second circumference is smaller than the first circumference to create a fluid tight seal that is strengthened when fluid pressure is increased inside the base ring. In certain embodiments, the tissue attachment element is a coil, and the tissue is a heart.

FIGS. 37A-37B illustrate another embodiment of an attaching device 820 including a secondary sealing element, as may be beneficial in certain applications to complement or supplement the inward compression provided by a coil. Specifically, the attaching device 820 may include an outward facing flange 3010 positioned outside of a coil 3020. In some embodiments, the outward facing flange 3010 may be attached to a distal end of an outer ring 3030 of the attaching device 820. In use, the outward facing flange 3010 may press or compress against the outer surface of the tissue wall when the coil 3020 in inserted into the tissue wall. In this manner, the outward facing flange 3010 may form a secondary seal against the tissue wall. The embodiment of FIGS. 37A-37B may be of particular benefit in applications where additional fixation of the attaching device 820 to the tissue wall is required, as may be accomplished by a suture-based "bailout" procedure. In this embodiment, the flange 3010 may be made of a soft material, such as a textile or polymer, configured to be sutured onto the outer surface of the tissue wall. When a soft polymer or other material is used, the flange 3010 may be reinforced with an internal wireframe 3040 or other support structure, as shown in FIG. 37A, to prevent the suture from tearing out of the flange 3010 when tightened. In another embodiment, the flange 3010 may be made of a rigid material and may include apertures 3050 defined therein, as shown in FIG. 37B, for receiving the suture therethrough. The apertures 3050 may be covered with a soft material that will allow the sutures to pass therethrough and through the apertures 3050.

FIG. 38 illustrates another embodiment of an attaching device 820 including a secondary sealing element, as may be beneficial in certain applications to complement or supplement the inward compression provided by a coil. Specifically, the attaching device 820 may include an outward facing flange (not shown) positioned outside of a coil 3120, similar to the flange 3010 described above. The attaching device 820 also may include a wireframe 3140 or other support structure positioned within the flange and at least partially outside of the coil 3120. In some embodiments, the wireframe 3140 may be attached to a distal end of an outer ring 3130 of the attaching device 820. In certain embodiments, the wireframe 3140 may be configured to pivot on the outer ring 3130 when an element is passed through the aperture of the attaching device. Specifically, the wireframe 3140 may include outer portions 3142 extending outward from the outer ring 3130 and connected to inner portions 3144 extending inward from the outer ring 3130 into the aperture, as shown. In this manner when an element is passed through the aperture, the flange would pivot or flip backwards (proximally), becoming flatter, less curved against the outer surface of the tissue wall and reducing friction between the flange and the tissue wall, which will simplify the attachment process.

FIG. 39 illustrates an example embodiment of a coil that may be used in any one of the attaching devices described herein to enhance sealing of the tissue wall about the puncture. Specifically, the coil 3200 may be used where a secondary seal is required between the ring, flange, skirt or other element of the attaching device and the outer surface of the tissue wall. As shown in FIG. 39, the coil 3200 has a proximal end 3210 and a distal end 3220, and the coil 3200 has a different pitch (distance between successive coils) at the proximal end 3210 as compared to the distal end 3220. In this manner, insertion of the coil 3200 into the tissue wall will generate additional pressure between the outer surface and the inner surface of the tissue wall, thereby facilitating fixation of the coil in the tissue wall and sealing of the attaching device 820 thereabout. In the embodiment of FIG. 39, the pitch of the coil 3200 at the distal end 3220 is greater than the pitch of the coil at the proximal end 3210. Accordingly, as the coil 3200 is inserted into the tissue wall, the layer of tissue into which the distal end 3220 is inserted is relatively thick, and as the coil 3200 advances through the tissue wall, this layer is compressed axially because of the smaller pitch of the coil 3200 toward the proximal end 3210. As the attaching device 820 is further inserted into the tissue wall and the portion of the coil 3200 near the proximal end 3210 enters the tissue, the proximal features of the attaching device 820 (outer ring, flange, skirt) are subjected to additional pressure from this compressed layer, which tightens the seal between the surfaces in contact with the tissue wall.

FIG. 40 illustrates a cross sectional view of an embodiment similar to that shown in FIG. 35A-35C, wherein an attaching device 820 includes a secondary sealing element, as may be beneficial in certain applications to complement or supplement the inward compression provided by a coil. Specifically, the attaching device 820 may include an inner skirt 2810 or ring positioned within a coil 2820. In some embodiments, the inner skirt 2810 may be attached to a distal end of an outer ring 2830 of the attaching device 820. As shown in FIG. 40, the inner skirt 2810 may press or compress against the outer surface of the tissue wall when the coil 2820 is inserted into the tissue wall. In this manner, the inner skirt 2810 forms a secondary seal against the tissue wall. An advantage is for the indentation to provide a seal around the circumference of the device and prevent the occurrence of blood loss during exchange of TAVI tools.

Other embodiments of the inventions described herein provide for atraumatic access to the left ventricle to minimize blood loss around the periphery of the transapical port during a TAVI or other procedure. As shown in FIGS. 41A-41C, the invention provides an embodiment wherein an inflatable balloon 4100 travels over a guide wire 4050 to the tissue site where the attaching device will be installed to gently expand the target tissue. Initially, a needle, such as a Seldinger needle, can be used to pierce the myocardium, and then reversed out. The combination balloon 4100 and attachment device 4020 with coil 4040 travels over the guide wire 4050. The wrapped balloon 4100 has a sufficiently low profile to smoothly travel through the myocardium. An increase in diameter between the wrapped balloon and the rest of the body of the sheath can act as a natural stop and signal to the operator to now inflate the balloon. Additionally, or alternatively, a radiopaque marker 4120 may be incorporated into the balloon 4100 for verification of location within the tissue. When the balloon 4100 is at the intended location within the target the wall of the myocardium as shown in FIG. 41B, it is inflated with gas or fluid to approximately the same diameter as the body of the tube (or sheath) 4060 to be inserted thereover, as shown in FIG. 41C. The sheath 4060 can then be advanced and in doing so, brings the coil 4040 into contact with the myocardium. Once the large coil implant has been delivered, the balloon is then deflated and removed, leaving the thin-walled outer sleeve attached as a sealed (yet completely flexible) conduit through which the TAVI system can pass.

The embodiment provides an atraumatic way of gaining access to the left ventricle, because the dilation of the hole in the myocardium is done gradually, consistently, and without a stabbing action used with existing devices. Furthermore, when the shape of the hole in the coil implant is designed in the proper way, then inflation of the non-compliant balloon will allow the implant to be gripped to allow a torque to be applied to the myocardium. In an embodiment shown in FIG. 42, the proximal end 4080 of the balloon 4100 is also shown as expanded, allowing it to be grasped by the surgeon and turned with substantial torque.

Once the TAVI procedure has been completed, closure can be completed as described previously, however, the cap will travel over the guide wire and into position, thereby requiring a hemostatic valve 4085. A seal can be attained with a plug-like extension on the distal side of the cap. In the embodiment shown, to detach the flexible conduit 4095 from the attachment device 4020, an external ring 4090 in communication with a perforation on the conduit 4095 can be pulled proximally by the operator at the end of the procedure to detach and remove the flexible conduit 4095 from the attaching device 4020.

FIGS. 43A-43B are cross sectional views of the balloon 4100 within the myocardium 4010 to illustrate non-limiting, exemplary non-circular shapes for the device, to allow the implant to be gripped by the inflated balloon and then torqued into place (arrows show one direction of torque). An added benefit of the oval shape is that it allows easier transition through the ribs when advanced along the minor axis.

Alternatively, as is shown in FIGS. 44A-44B, the coil 4040 can be delivered minimally invasively through the ribs 4015 when compressed and turned at an angle, like a coin through a slot. FIG. 44A shows the coil positioned outside of the ribs 4015. FIG. 44B shows the coil positioned inside of the ribs 4015. The inflating balloon 4010 provides a method for correcting the orientation of the coil 4040 once a port is made through the ribs 4015. In this embodiment, the coil 4040 is compressed axially in order to minimize its lateral profile, thereby taking the shape of a disc or coin. In this case, a thin incision in the tissue may be enough to pass the device through the ribs. The coil 4040 can then be rotated with or without the aid of the balloon 4010. After rotation, the coil 4040 is released and allowed to become uncompressed, and then torqued into the tissue. In order to compress the coil 4040 axially, a sheath or other restrictive element may be used. FIGS. 45A and 45B show additional views of the inflatable dilator balloon 4100 described above.

In some embodiments of the invention, the attaching device and coil may be delivered through the pericardium onto the heart, compressing the pericardium against the epicardium and accessing and sealing through both surfaces. However, for patients where it is difficult to deliver the anchoring and closure systems over the pericardium, the invention provides an additional pericardial control tool as illustrated in FIGS. 46A-46C. The pericardial control tool 4200 may be guided using a guide wire or other means to the pericardium 4102. Once the pericardium 4102 is captured or penetrated by the tool 4200, an extension 4210 can be used to control the distance between the pericardial sack and the epicardial surface of the myocardium 4010. Control may be maintained by mechanical means including interference or penetration, vacuum suction and magnetic or chemical means, such as temporary biocompatible glues, such as are known in the art. The pericardial tool 4200 may also be radio opaque and its shape configured to guide transapical delivery devices into the correct location in the heart. The tools may also contain one or multiple lumens that may serve as drains of the fluid in the pericardial space and adjacent areas of the thorax.

As shown in FIGS. 46B and 46C, after attaining control of the pericardial space, a delivery system 4300 may be used to deploy an attachment device 4020 and anchoring element or coil 4040 onto the epicardial surface of the myocardium 4010 without interference of the pericardium 4012. In some embodiments the anchoring coil 4040 (or other type of anchor) may be collapsed into a tube or differently shaped sheath within the delivery system 4300. As shown in FIG. 46C, the flexible distal ends 4310 of the delivery system 4300 may open while exposing the collapsed coil 4040, and thereby also serve to stabilize the pericardium 4012. The embodiments described immediately above are of particular importance when using percutaneous transapical approaches where the pericardium may not be fully retrieved from the access site.

In another embodiment of the invention as shown in FIGS. 47A-47J, a percutaneous transapical port and closure system is provided. The system is delivered over a guide wire 5050, or using other orientation means to a target site in the heart myocardium 5010. The heart may be accessed using a dilator 5060 and sheath 5070. The dilator 5060 may be a tapered solid rod or a balloon expandable element as shown and described previously.

After accessing the heart (or other soft tissue organ), the system may be stabilized in place using vacuum suction, articulating wires or other mechanical means on the portion of the port 5062 disposed within the tissue 5010. In the embodiment shown, epicardial vacuum suction orifices 5080 are present and configured to selectively attach the tissue port 5062 to the epicardial surface of the heart myocardium 5010. Alternatively, or additionally as shown, the sheath 5060 and port 5062 can be stabilized within the tissue 5010 with circumferential lateral surface vacuum suction orifices 5085 in order to selectively attach to the tissue side walls of the puncture site in the myocardium (or other tissue). Such systems not only stabilize the port 5062 and device but allow for para-sheath sealing. FIGS. 47D-47H show vacuum suction orifices 5080, 5085 which are configured to attach the system to the tissue at both the epicardial surface and within the sidewalls of the puncture site. This also insures two different sections of sealing which act independently to improve security of the device.

Figure 47A:
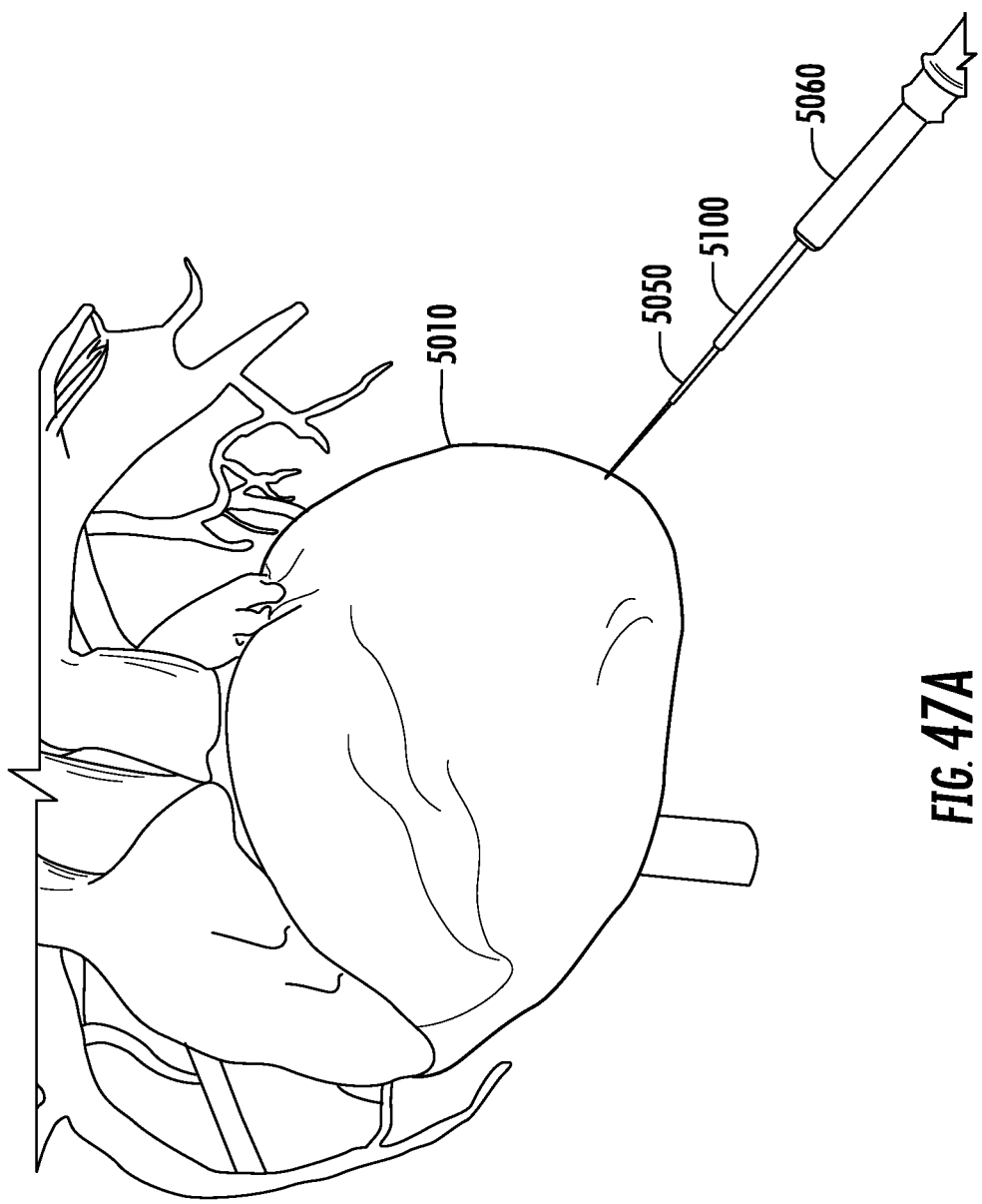
Figure 47B:
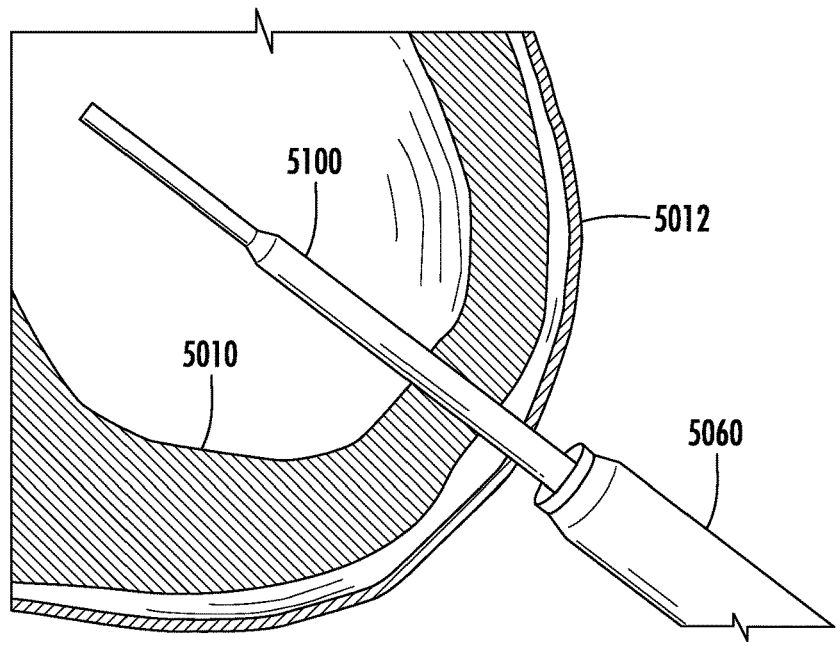
Figure 47C:
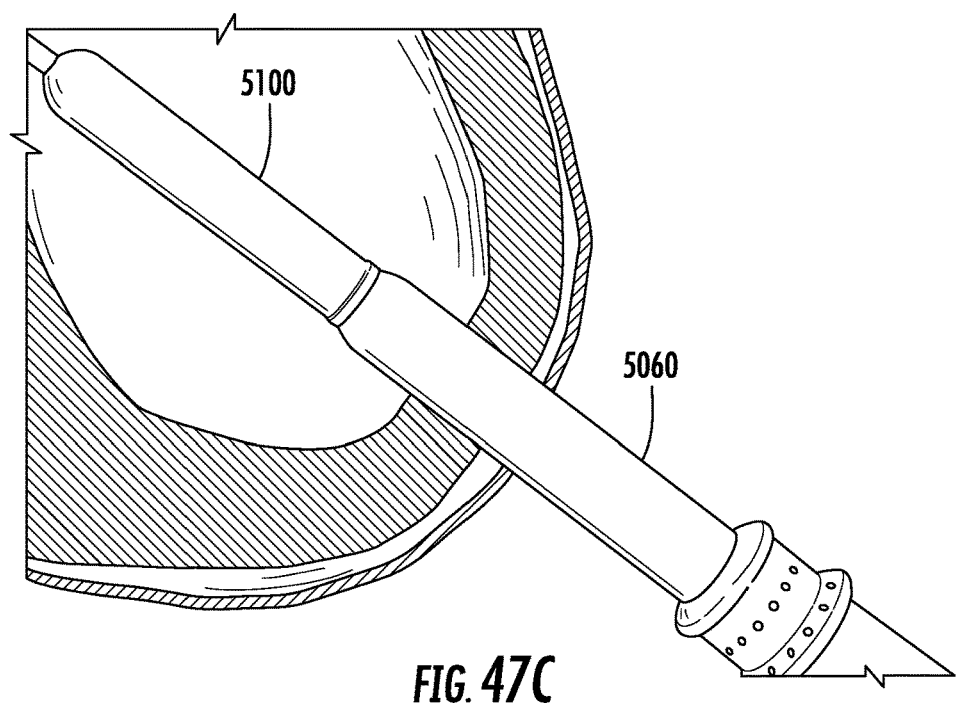
Figure 47D:
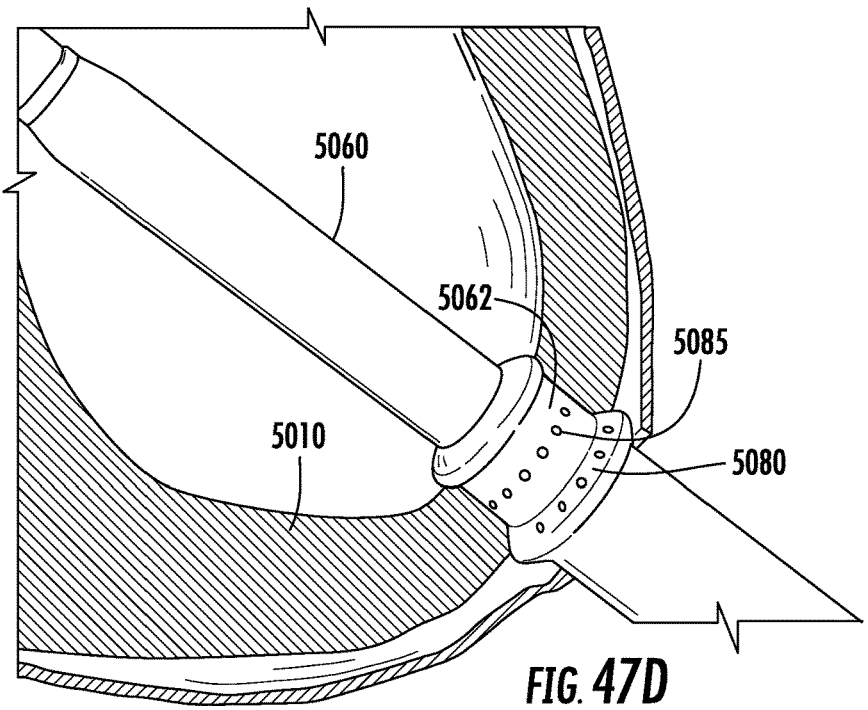
Figure 47E:
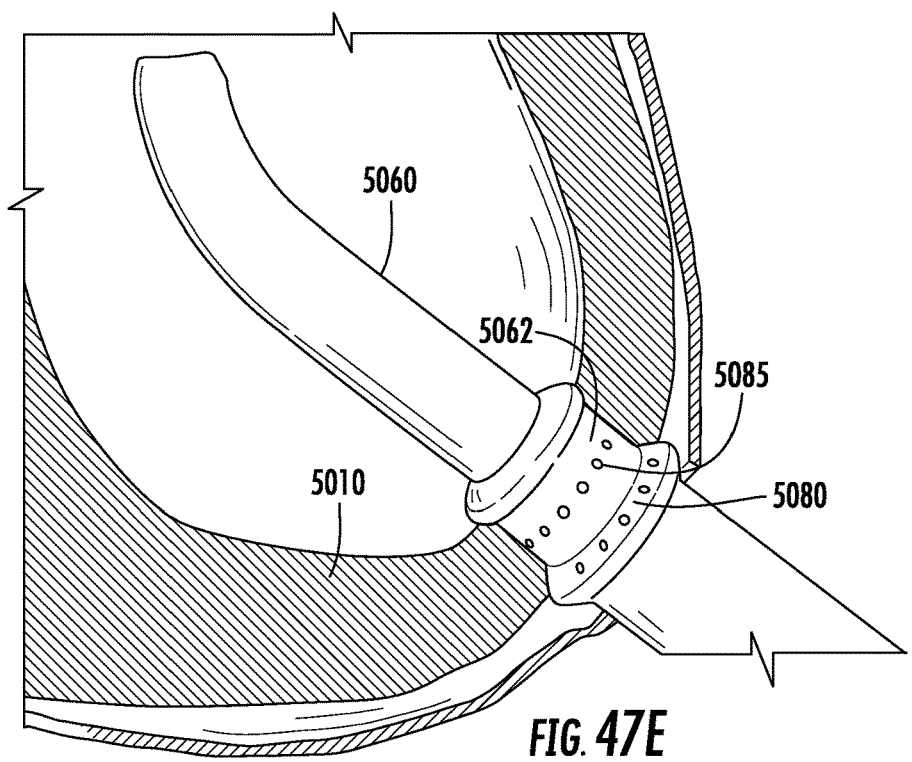
Figure 47F:
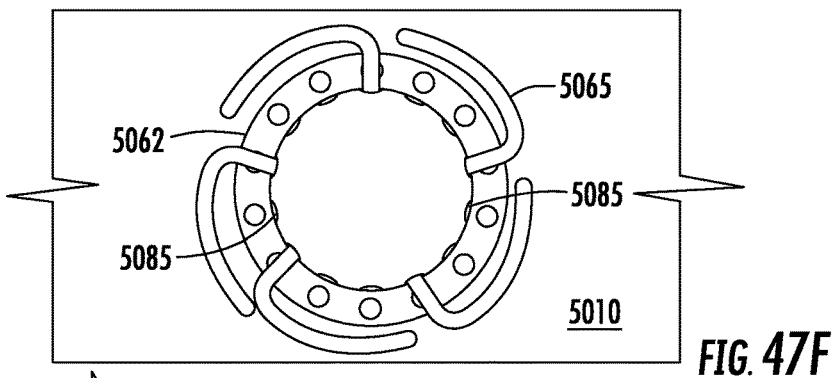

In alternative embodiments shown in the cross sectional view of FIG. 47F, the invention contemplates that actuating tissue grasping appendages 5065, such as wires, may be extended through some of the orifices in the portion 5062 of the device located within the sidewalls of the punctured tissue 5010 by turning an actuator (counterclockwise as illustrated) on the proximal end of the delivery device (not shown) for stabilizing the device in position within the tissue 5010. The appendages create a pinwheel-like pattern for stabilizing the surgical device. When the procedure is completed, reverse rotation of the actuator (clockwise as illustrated) will release and retract the grasping appendages 5065 from the tissue, and optionally back within the orifices of the port 5062, for removal of the instrument.

The sheath 5060 may also be configured to freely move axially or rotate within the vacuum suction element so as not to break the seal when maneuvering the system. As shown in FIG. 47E, after removal of the dilation system, a steerable sheath 5060 configuration may be used to guide the element being introduced into the organ through the trans-apical port into a desired location. This sheath 5060 may also be collapsible and/or free to bend in three dimensions to facilitate the performance of various surgical procedures through the port.

Figure 47G:
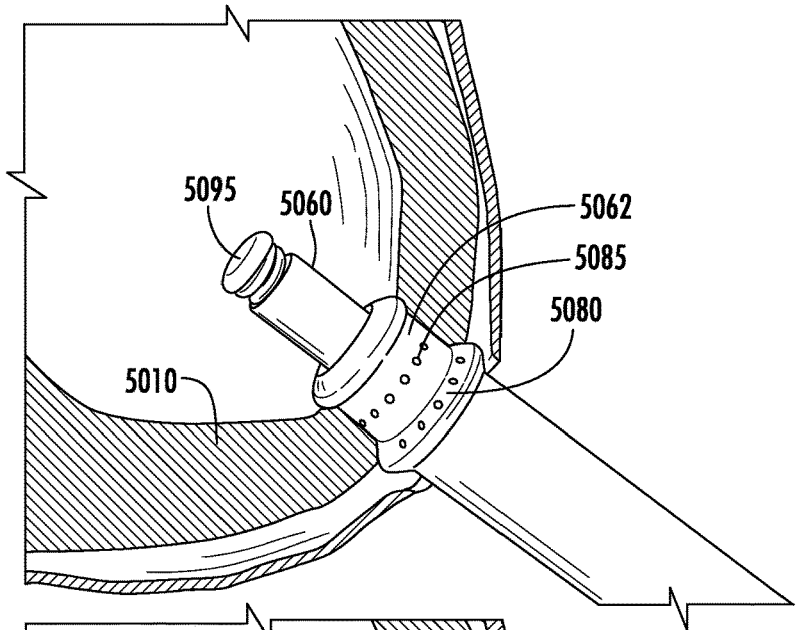
Figure 47H:
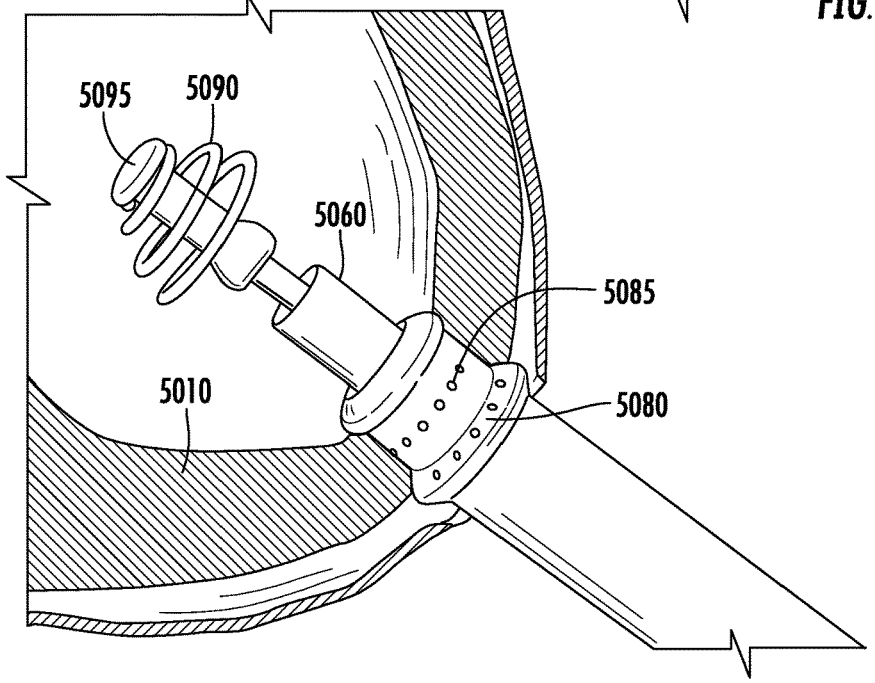
Figure 47I:
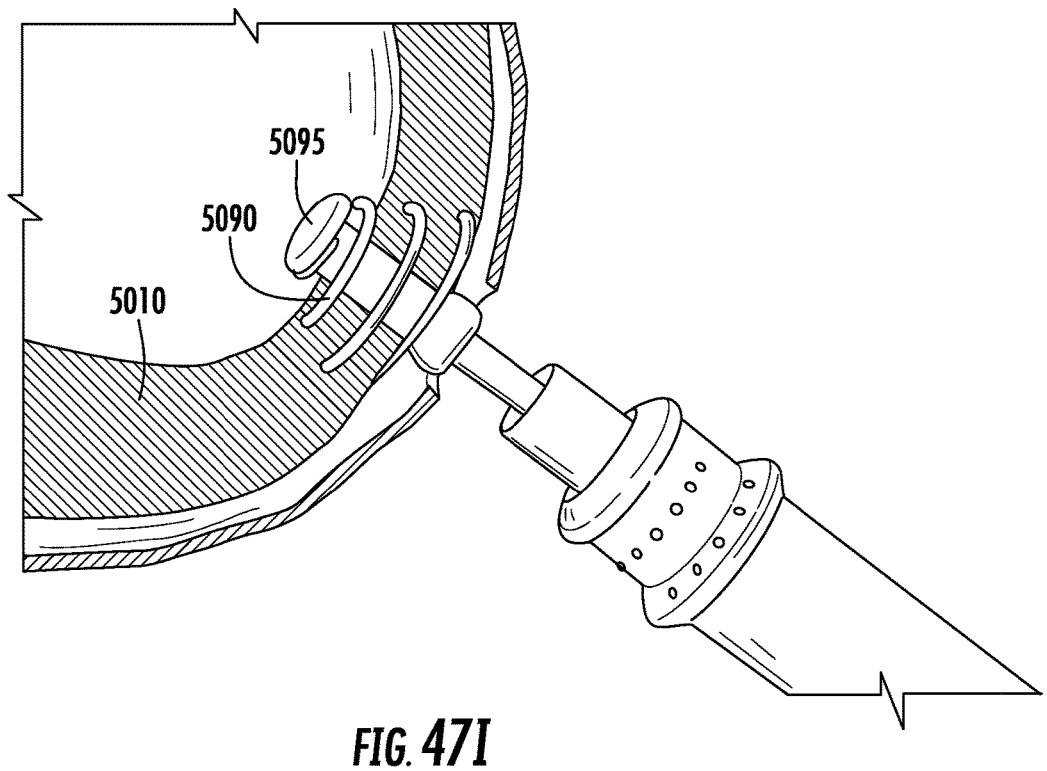
Figure 47J:
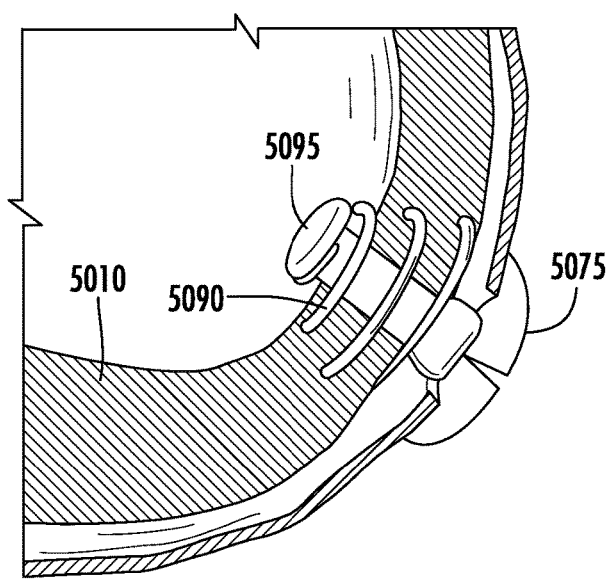

In a configuration for closure of the access site as shown in FIGS. 47G-47J, an inverted conical sealing coil 5090 may be delivered through the tissue port onto the internal surface. The coil 5090 may be delivered through the port 5062 in a collapsed state as shown in FIG. 47G, which can expand into an operable configuration when extended distally past the port 5062 as shown in FIG. 47H. Although the exemplified embodiment is a conical sealing coil, a straight sealing coil may also be used or other barbed or non-coiled closure elements as described in the text and figures above. The coil 5090 may or may not have a central sealing plug 5095 to aid in sealing by operation of rotating the coil within the tissue to create inward pressure of the tissue around the plug 5095. After the sealing closure coil 5090 or other sealing element is delivered into the internal surface of the tissue 5010 as shown in FIG. 47J, all delivery tools may then be disengaged and removed as hemostasis is achieved. An external hemostatic device 5075, similar to an umbrella or cap, can optionally be deployed and attached to the sealing plug 5095 to cover the puncture site and assist in sealing the exterior of the tissue, including the pericardium in the case of transapical procedures.

The collapsible closure element or coil may be made of any biocompatible material including metals, polymers or ceramics. The closure coil or other closure means may be partially or fully biodegradable. The plug which may be part of the closure coil may be expandable. In expandable embodiments materials such a polyethylene glycol (PEG) may be used.

In the embodiments described, the tissue wall is penetrated by elements that apply forces to it. The feasibility and success of such procedures is directly tied to the quality and integrity of the tissue. Traditionally, tissue integrity is evaluated by the clinician upon direct visualization and contact. This method is highly subjective and is often largely unknown until the tissue is pierced. Tissue quality and integrity as related to the technologies described above is associated with the capacity of the tissue to be pierced and deformed under forces without cracking or tearing. These attributes are directly associated to the penetrability and ductility of the tissue as a function of the elasticity of the tissue. The primary engineering variables involved are the modulus of elasticity and the shear modulus of the tissue. Because it would typically be too complex to calculate these variables directly for each live patient, one aspect of the invention provides method for determining an Index of Tissue Elasticity (ITE) of the cardiac tissue of a patient to assess viability for successfully placing an attachment device thereto. The ITE is of particular importance when dealing with procedures in the heart because large variability in heart tissue quality from patient to patient is observed. However, the ITE may also be used for other organs with internal fluid.

To determine the ITE, the method comprises, obtaining a strain field value of the tissue of interest, e.g., the apex of a heart. Strain field value ($\epsilon_o$) can be determined for example with a speckle tracking tool or by ultrasound using techniques well-known in the art. The method also comprises (in no particular order) obtaining local tissue curvature (r) and tissue thickness (t), such as with an echocardiogram image. The method further comprises then using the local curvature radius (r), tissue thickness (t) and ventricular pressure (p) to calculate local stress (σ) using pressurized cylinder equations, as shown below for thin walled (I) or thick walled (II) theory.

Local Stress Equations:
Thin walled $$\sigma_\theta = \frac{pr}{t} \tag{I}$$

Thick-walled $$\sigma_\gamma = \frac{p_i r_i \left(1 - \frac{r_0^2}{r^2}\right)}{r_0^2 - r_i^2} \tag{II}$$

The method then comprises using the strain field value ($\epsilon_o$) and local stress (σ) to calculate the elasticity (E), as shown below in formula (III) to derive an ITE of the apex of the patient's heart. The ITE of the patient can be compared with a database of apical elasticities of more than one other individual. Based on the comparative ITEs, prior observed clinical outcomes and sound medical judgment, the surgeon can proceed with installing the trans-apical port in the patient when the ITE is found to be within a clinically acceptable deviation from the average ITE observed in a healthy population.

$$\epsilon_\sigma = \frac{1}{E}\left(\left(r\frac{d\sigma_\gamma}{dr} + \sigma_\gamma\right) - \nu\sigma_\gamma\right) \tag{III}$$

wherein,
$\epsilon_o$ Strain field from speckle tracking
E Unknown Elasticity; calculated Index of Tissue Elasticity $$\frac{d\sigma_\gamma}{dr}$$

May assume linear or parabolic
ν Use Young's modulus/Poisson's ratio for myocardial muscle
$\sigma_\gamma$ Stress from ventricular pressure and wall curvature In summary, the above method uses strain, thickness, curvature and pressure to calculate the ITE. The ITE calculated does not equate to an exact modulus of elasticity, but provides a normalized index for comparison between patients. Specifically, the ITE may be compared to historical data on tissue quality of patients and procedure outcomes in order to identify a range of ITE values for which it is safe and effective to conduct such procedures. The strain field and local geometry generally can be obtained as described above from echo images and speckle tracking technologies. According to other embodiments, various well-known imaging technologies and methods may be used for this purpose, including ultrasonography, MRI elastomery, MRI myocardial tagging, ultrasound speckle tracking, and other techniques developed in the future. The steps in the above method for the calculation of the ITE may be implemented through an algorithm and code into a software package for the imaging machine. In this manner, the method may be automated for ease of implementation during clinical practice. The patient's ITE can be routinely compared to ITEs calculated from other patients to routinely develop a comparative standard of values within acceptable ranges for conducting transapical procedures with the devices of the present invention.

Another more direct, but invasive, method of calculating the elasticity of the tissue is to use an indentation tester or durometer in contact with the tissue in order to calculate its durometer level, a well-established engineering variable which may then be used to calculate the elasticity through mathematical formulas or computational finite element models. Various types of durometers are commercially available and simple to use. However, a durometer of the present invention is preferably made of biocompatible materials and designed to be sterilized. The invention also contemplates methods of assessing patient tissue competency for receiving an attachment device as described herein by using a durometer as an intermediate step to standardized measurement of ITE, correlating the values to clinical practice, and then comparing the direct results with those from the image based method described above as a form of calibration or validation. This aspect of the invention provides methods to more accurately characterize the tissue and standardize an evaluation against a database of other patients' tissues before initiating clinical procedures with the devices described herein.

We claim:

1. A tissue attaching device comprising:
   an outer base ring defining an opening therethrough and a central axis of the tissue attaching device;
   a tissue attachment element fixedly attached to the outer base ring and projecting distally therefrom in the direction of the central axis, wherein the tissue attachment element comprises a sharpened distal end configured for piercing a tissue surface of a tissue wall; and
   an annular sealing flange attached to the outer base ring outside of the tissue attachment element and projecting distally therefrom in the direction of the central axis, wherein the annular sealing flange comprises a proximal portion projecting away from the central axis at an outward angle to define a first circumference and a distal portion projecting toward the central axis at an inward angle to define a second circumference for interfacing with the tissue surface surrounding the tissue attachment element, and wherein the second circumference is smaller than the first circumference to create a fluid tight seal that is strengthened when fluid pressure is increased inside the annular sealing flange.

2. The tissue attaching device of claim 1, wherein the tissue attachment element is a coil.

3. The tissue attaching device of claim 2, wherein the coil has a radially-expanding helical shape projecting away from the central axis.

4. A tissue attaching device comprising:
   an outer base ring defining an opening therethrough and a central axis of the tissue attaching device;
   a tissue attachment element fixedly attached to the outer base ring and projecting distally therefrom in the direction of the central axis, wherein the tissue attachment element comprises a sharpened distal end configured for piercing a tissue surface of a tissue wall; and
   an annular sealing flange attached to the outer base ring inside of the tissue attachment element and projecting distally therefrom in the direction of the central axis.

5. The tissue attaching device of claim 4, wherein the tissue attachment element is a coil.

6. The tissue attaching device of claim 4, wherein the tissue attachment element projects distally beyond the annular sealing flange in the direction of the central axis.

7. The tissue attaching device of claim 1, wherein the tissue attachment element is configured for compressing the tissue wall inward toward the central axis.

8. The tissue attaching device of claim 1, wherein the tissue attachment element projects distally beyond the annular sealing flange in the direction of the central axis.

9. The tissue attaching device of claim 1, wherein the annular sealing flange is attached to a distal end of the outer base ring.

10. The tissue attaching device of claim 1, wherein the annular sealing flange has a V-shaped profile defined by the proximal portion and the distal portion.

11. The tissue attaching device of claim 1, wherein the tissue attachment element is configured for inserting into the tissue wall, and wherein the annular sealing flange is configured for pressing against the tissue surface when the tissue attachment element is inserted into the tissue wall.

12. The tissue attaching device of claim 1, wherein the tissue attachment element is configured for inserting into the tissue wall, and wherein the annular sealing flange is configured for compressing against the tissue surface when the tissue attachment element is inserted into the tissue wall.

13. The tissue attaching device of claim 1, wherein the distal portion of the annular sealing flange is configured to be biased away from the central axis when fluid pressure is increased inside the annular sealing flange.

14. The tissue attaching device of claim 1, wherein the annular sealing flange is spaced apart from a proximal end of the outer base ring in the direction of the central axis.

15. The tissue attaching device of claim 1, wherein the outer base ring defines a third circumference that is larger than the second circumference.

16. The tissue attaching device of claim 15, wherein the first circumference is larger than the third circumference.

17. The tissue attaching device of claim 1, wherein the outer base ring has a circular shape, and wherein the opening has a circular shape.

18. The tissue attaching device of claim 1, wherein the outer base ring defines a plurality of apertures therethrough spaced apart from the central axis, and wherein the annular sealing flange covers the apertures.

* * * * *